(12) United States Patent
Andreas et al.

(10) Patent No.: US 8,353,945 B2
(45) Date of Patent: *Jan. 15, 2013

(54) DELIVERY CATHETER HAVING ACTIVE ENGAGEMENT MECHANISM FOR PROSTHESIS

(75) Inventors: Bernard H. Andreas, Redwood City, CA (US); Matthew McDonald, Santa Cruz, CA (US); Jay S. Daulton, Gilroy, CA (US); Andrew Leopold, Hawthorn Woods, IL (US); Philip Leopold, North Barrington, IL (US); Matt Maulding, Bellemont, AZ (US); Andrew Black, Round Lake, IL (US)

(73) Assignee: J.W. Medical System Ltd., Los Altos, CA (US)

( * ) Notice: Subject to any disclaimer, the term of this patent is extended or adjusted under 35 U.S.C. 154(b) by 903 days.

This patent is subject to a terminal disclaimer.

(21) Appl. No.: 11/735,400

(22) Filed: Apr. 13, 2007

(65) Prior Publication Data

US 2007/0276461 A1 Nov. 29, 2007

Related U.S. Application Data

(60) Continuation-in-part of application No. 11/538,904, filed on Oct. 5, 2006, now Pat. No. 7,922,755, which is a division of application No. 10/412,714, filed on Apr. 10, 2003, now Pat. No. 7,137,993, which is a continuation-in-part of application No. 10/306,813, filed on Nov. 27, 2002, now abandoned.

(60) Provisional application No. 60/747,774, filed on May 19, 2006, provisional application No. 60/336,967, filed on Dec. 3, 2001, provisional application No. 60/364,389, filed on Mar. 13, 2002.

(51) Int. Cl.
*A61F 2/06* (2006.01)
(52) U.S. Cl. ..................................... 623/1.11
(58) Field of Classification Search ............... 623/1.11, 623/1.12, 1.16; 606/108, 191–198, 113, 606/114, 127, 200
See application file for complete search history.

(56) References Cited

U.S. PATENT DOCUMENTS

| 5,312,415 | A | * | 5/1994 | Palermo | 606/108 |
| 5,593,412 | A | * | 1/1997 | Martinez et al. | 623/1.11 |
| 6,287,291 | B1 | * | 9/2001 | Bigus et al. | 604/523 |
| 7,137,993 | B2 | * | 11/2006 | Acosta et al. | 623/1.11 |
| 7,294,146 | B2 | * | 11/2007 | Chew et al. | 623/1.12 |
| 7,300,456 | B2 | * | 11/2007 | Andreas et al. | 623/1.12 |

* cited by examiner

*Primary Examiner* — Gary Jackson
*Assistant Examiner* — Eric Blatt
(74) *Attorney, Agent, or Firm* — Levine Bagade Han LLP

(57) ABSTRACT

Delivery catheters and systems are adapted for delivering multiple discreet prostheses in body lumens. An exemplary delivery catheter comprises a sheath, a pusher for moving the prostheses relative to the sheath, and a valve member for selectively retaining the prostheses in the sheath. For balloon expandable stents, an elongated shaft and an expandable member are slidably disposed in the sheath, and the prostheses are positionable on the expandable member for deployment in the body lumen. The valve member allows a selected number of prostheses to be deployed from the sheath while retaining other prostheses within the sheath.

17 Claims, 38 Drawing Sheets

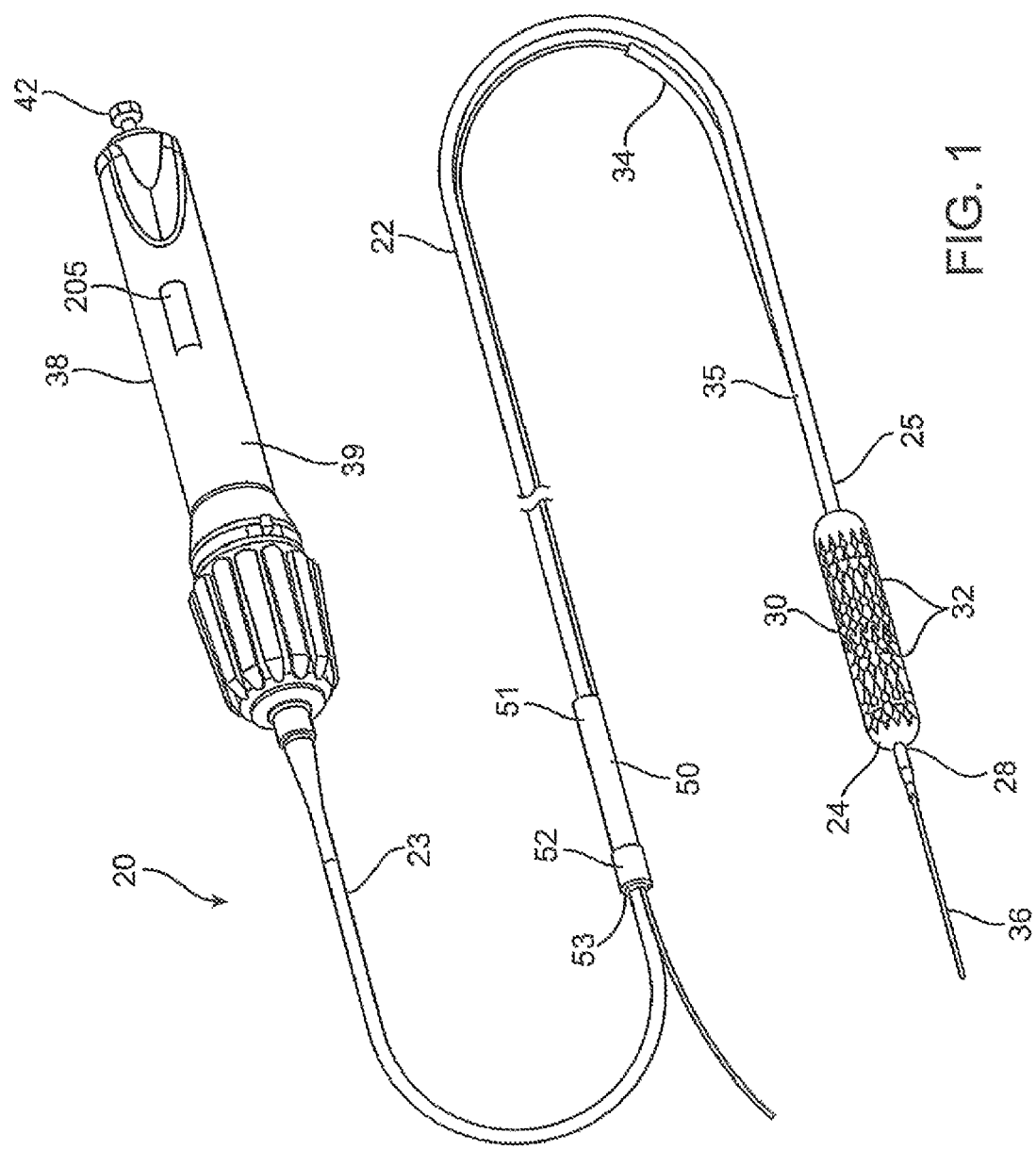

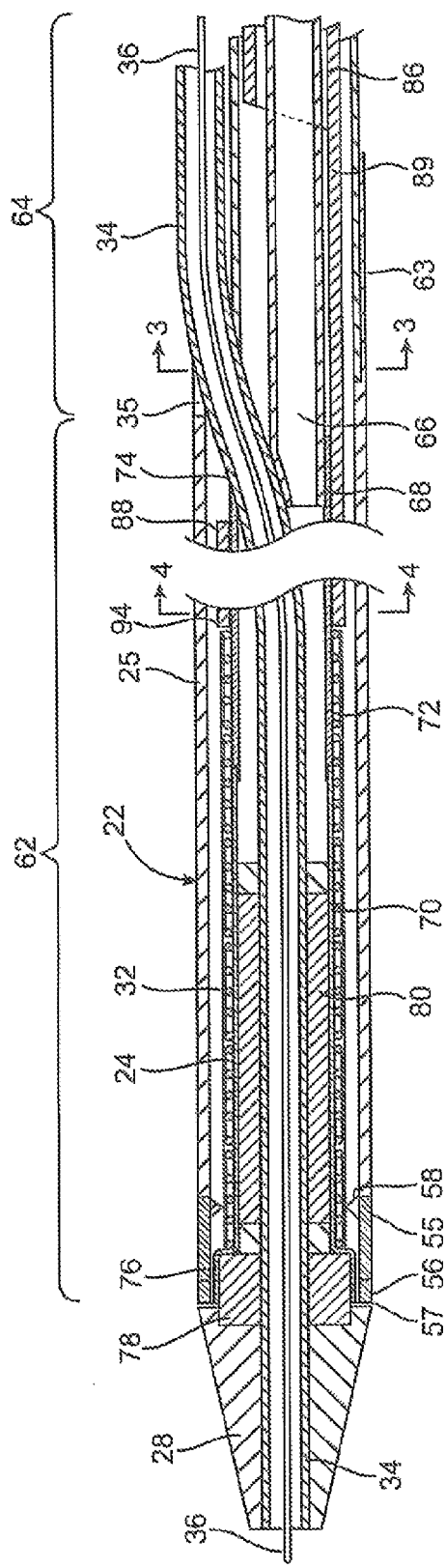
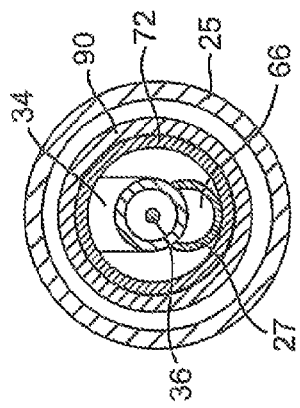
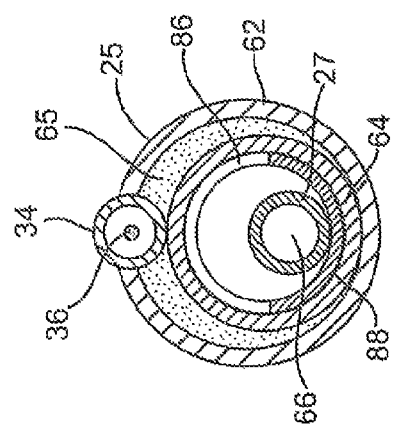
FIG. 2A
FIG. 4
FIG. 3

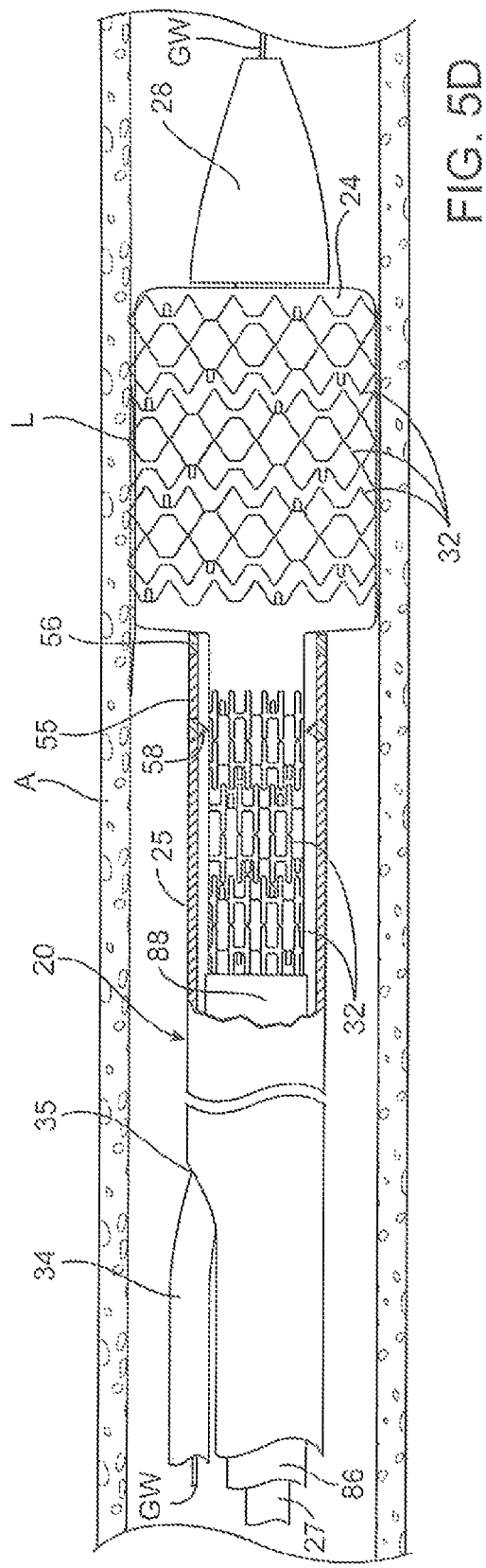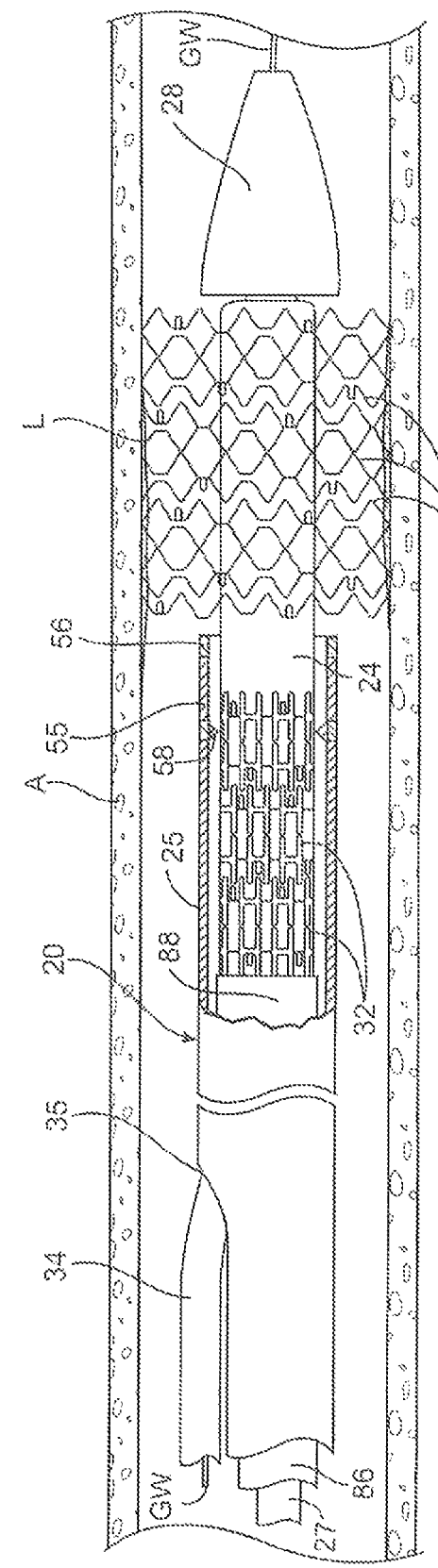

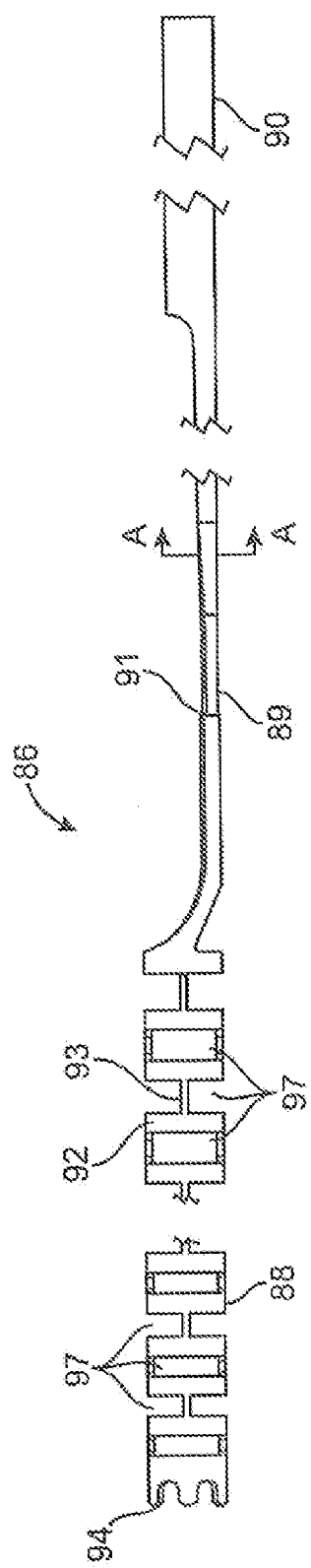
FIG. 6
FIG. 6A

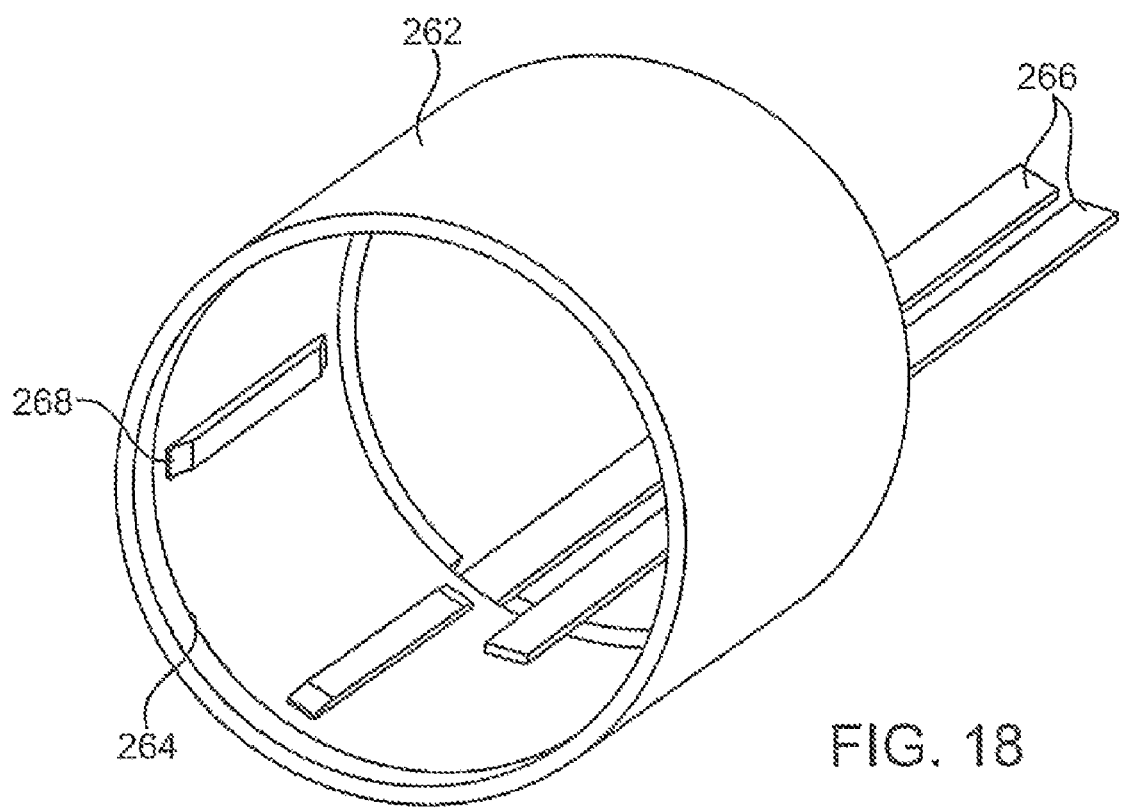

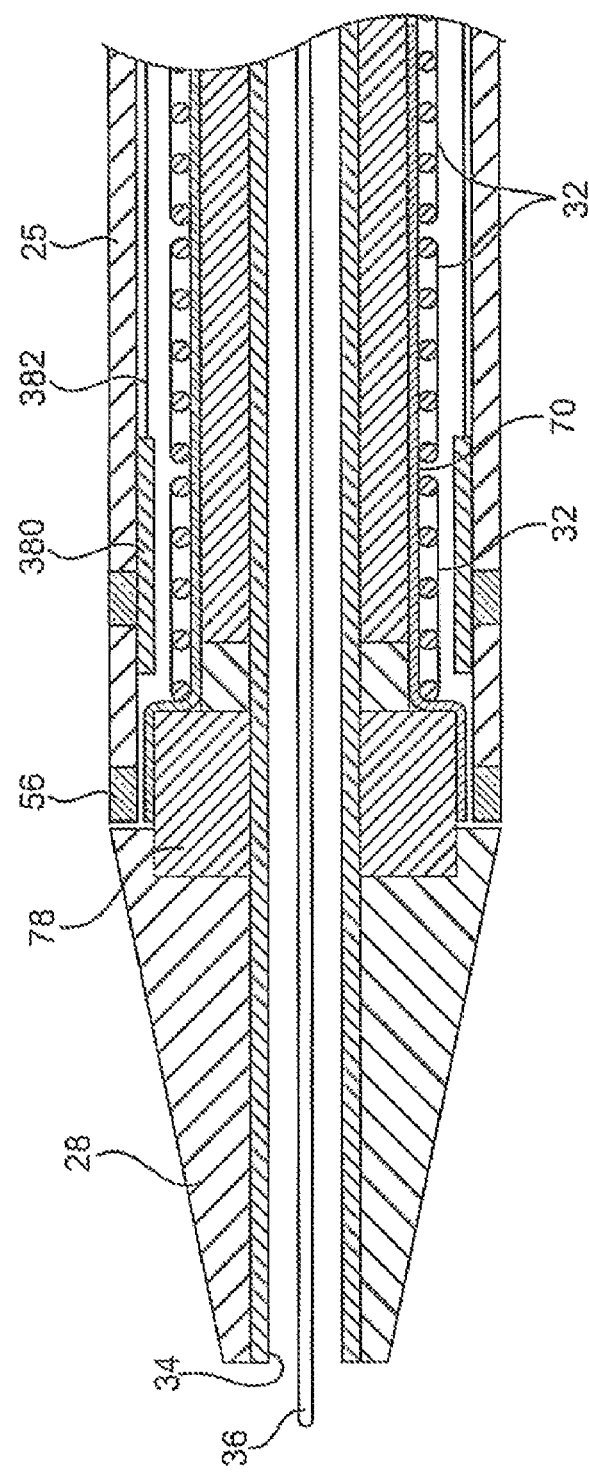

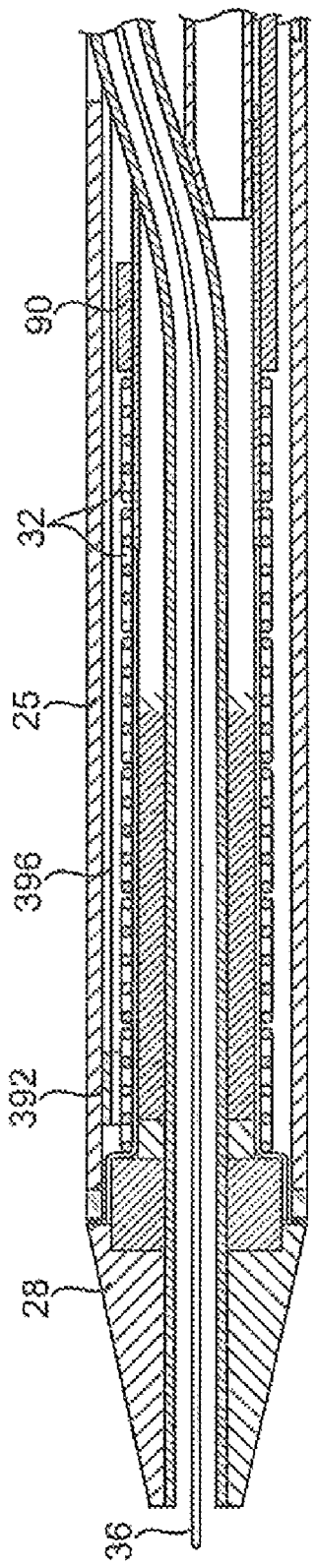
FIG. 36A
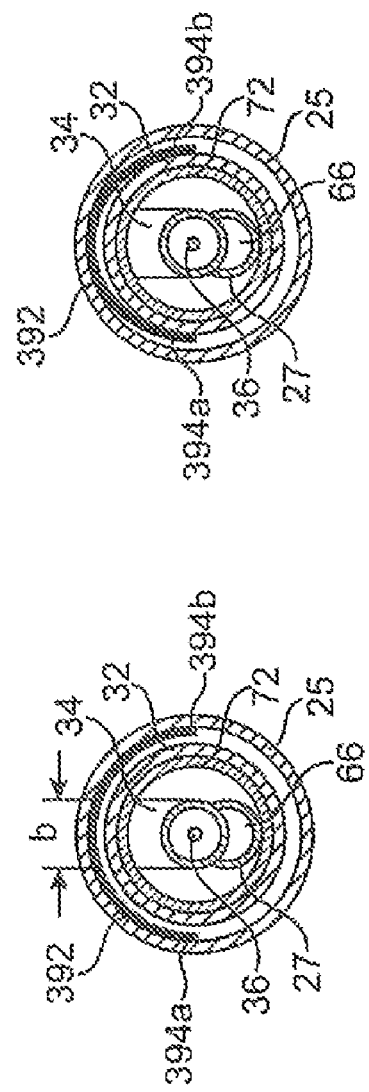
FIG. 36C
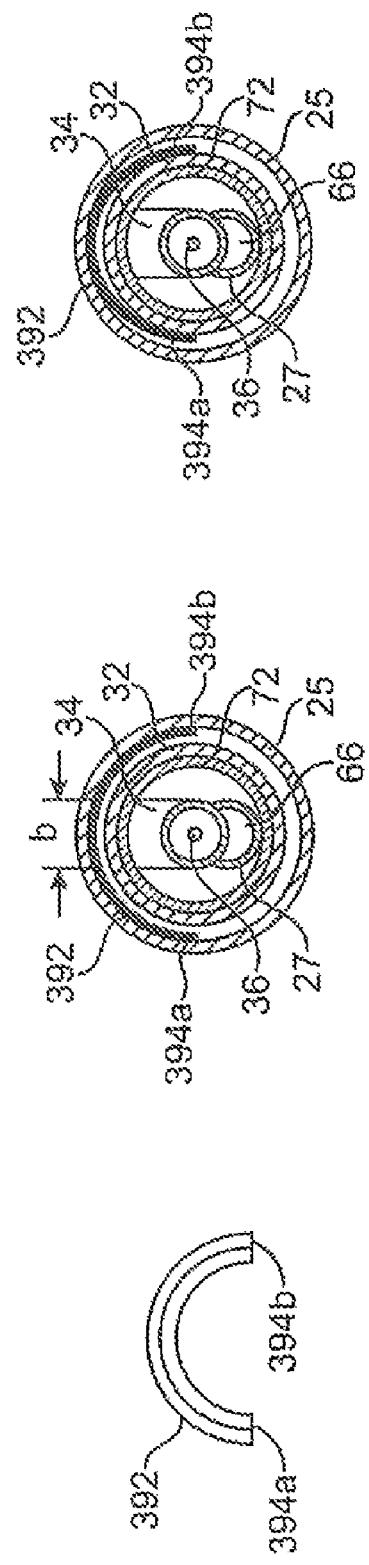
FIG. 36D
FIG. 36B

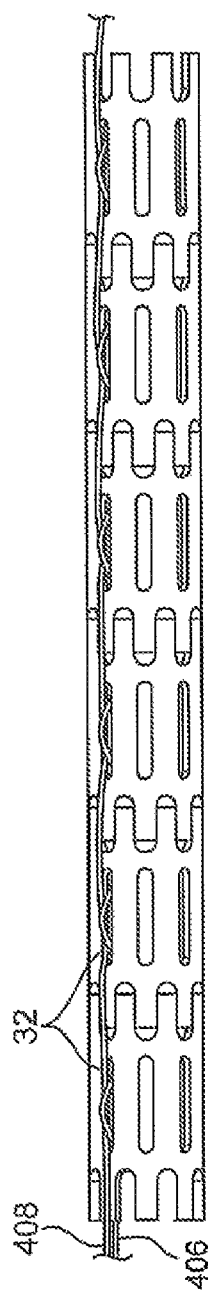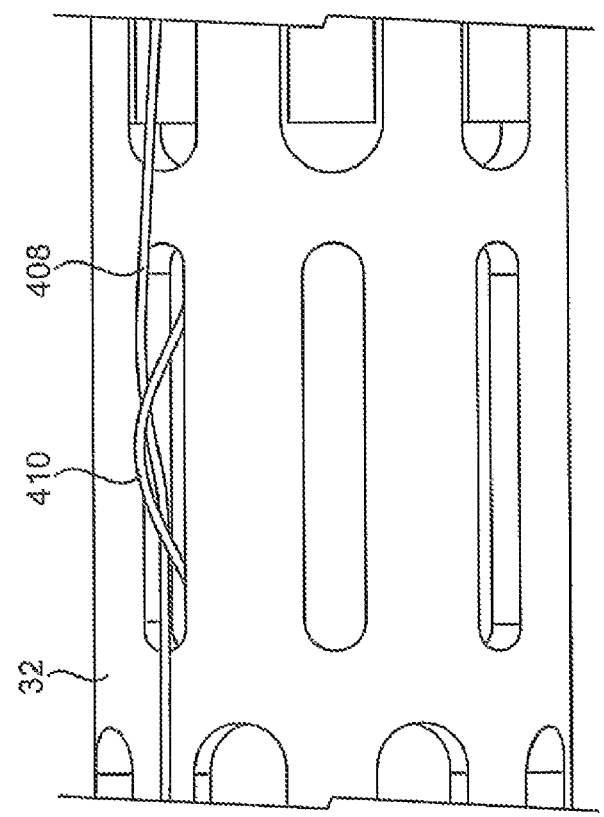
FIG. 38A
FIG. 38B

DELIVERY CATHETER HAVING ACTIVE ENGAGEMENT MECHANISM FOR PROSTHESIS

CROSS-REFERENCE TO RELATED APPLICATIONS

The present application claims the benefit of priority to U.S. Provisional Patent Application Ser. No. 60/747,774 filed May 19, 2006, and is also a continuation-in-part of co-pending U.S. patent application Ser. No. 11/538,904 filed Oct. 5, 2006, which is a divisional of U.S. patent application Ser. No. 10/412,714 filed Apr. 10, 2003, which is a continuation-in-part of U.S. patent application Ser. No. 10/306,813 filed Nov. 27, 2002, which is a non-provisional of U.S. Provisional Patent Application Ser. No. 60/336,967 filed Dec. 3, 2001, and is also a non-provisional of U.S. Provisional Patent Application Ser. No. 60/364,389 filed Mar. 13, 2002, each of which is hereby incorporated by reference in its entirety.

BACKGROUND OF THE INVENTION

The present invention relates generally to interventional catheters and prostheses, and more specifically to catheters and prostheses for treatment of vascular diseases, including coronary artery disease and peripheral vascular disease, as well as diseases of other body lumens such as the biliary tract, fallopian tubes, urinary and digestive tracts, and other structures.

Balloon angioplasty and stenting are widely used in the treatment of coronary artery disease and peripheral vascular disease. In coronary artery disease, one or more coronary blood vessels become narrowed or closed due to the buildup of stenotic plaques on the arterial wall. This blocks blood flow to the heart muscle, potentially causing myocardial infarction. Such narrowing can also occur in peripheral blood vessels such as the carotids, femorals, iliacs and other arteries, blocking the blood supply to other vital tissues and organs.

Balloon angioplasty involves the use of a long flexible catheter having a balloon at its distal tip. The catheter is inserted into a peripheral artery such as the femoral and advanced transluminally into the diseased artery. The balloon is inflated within the narrowed portion of the vessel, thereby expanding the vascular lumen and restoring normal blood flow.

In some cases, however, balloon angioplasty alone is inadequate to treat vascular disease due to restenosis, the renarrowing of the artery following angioplasty. Stents have been developed to provide an intravascular frame or scaffold to maintain patency of the vascular lumen after it has been expanded. Stents are small tubular prostheses designed to be advanced to the treatment site in a collapsed configuration using an elongated delivery catheter. The stents are then expanded at the treatment site into engagement with the vessel wall to maintain vascular patency.

Stents may be either self-expanding or balloon expandable. Self-expanding stents are made of a shape memory material such as Nitinol and can be delivered in a compressed state within the tip of the delivery catheter and allowed to resiliently expand upon release from the delivery catheter. Balloon expandable stents are made of a malleable metal and are mounted to a balloon on the delivery catheter. When positioned at the treatment site, the balloon is inflated to expand the stent into engagement with the vessel.

Stents, however, have also suffered from the problem of restenosis. Restenosis rates with conventional coronary stents have ranged from 30-40%. The causes of such restenosis are not fully understood. However, it is believed that restenosis may be caused in some cases by the excessive stiffness of current stents and their inability to conform to vascular curves, shapes, dimensional changes, and movements. This problem is particularly acute with longer lesions, which may extend over curved and tapered sections of a vessel and may be subject to non-uniform movements along their lengths.

The need has thus been demonstrated for highly flexible stents that may be used to treat long, curved, and tapered vascular regions. In co-pending U.S. patent application Ser. No. 10/637,713, filed Aug. 8, 2003, entitled "Apparatus and Methods for Delivery of Vascular Prostheses," the full disclosure of which is incorporated herein by reference, highly flexible multi-segmented stents and associated delivery devices are disclosed that enable the treatment of long, curved or tapered vascular lesions. The disclosed delivery devices enable the selective deployment of one or more stent segments at a treatment site to allow the user to customize stent length in situ. Moreover, the device can be repositioned at multiple vascular sites to deploy a plurality of stents of various lengths.

Other custom-length stents and delivery devices are described in co-pending U.S. patent application Ser. No. 10/412,714, filed Apr. 10, 2003, entitled "Apparatus and Methods for Delivery of Multiple Distributed Stents," (hereinafter referred to as "the '714 application"), which is also incorporated herein by reference. The '714 application describes devices for delivering multiple discrete prostheses, such as stents, in body lumens. An exemplary delivery catheter includes a sheath, a pusher for moving the prostheses relative to the sheath, and a valve member for selectively retaining the prostheses in the sheath. The valve member allows a selected number of prostheses to be deployed from the sheath while retaining other prostheses within the sheath.

The '714 application describes prosthesis delivery catheters and systems that include valve members that function either actively or passively. In passive configurations, the valve member prevents the prosthesis from exiting the passage under a first force and allows the prosthesis to exit the passage under a second force higher than the first force. In active embodiments, the valve member is selectively movable between a contracted configuration in which the valve member allows movement of prostheses out of the sheath, and an extended configuration in which the valve member inhibits movement of prostheses out of the sheath.

Variable length angioplasty devices have also been proposed. For example, U.S. Pat. No. 5,246,421 to Saab discloses angioplasty catheters having an elongated balloon and an external sheath that is axially slidable relative to the balloon. The sheath can be retracted to expose a selected length of the balloon for expansion at a treatment site. The catheter can then be repositioned and another length of balloon exposed to treat one or more additional sites.

While such custom-length stents and angioplasty catheters have shown great promise, there remains a need for improved ways of delivering multi-segment prostheses in body lumens. For example, whereas the '714 application describes several valve member embodiments, including embodiments that function both passively and actively, there remains a need for valve members that are able to effectively and consistently create separation between the distal-most prosthesis segment within the catheter shaft and the proximal-most prosthesis segment exposed distally of the shaft. Such valve members should also function while minimizing damage to the prosthesis segments or any coatings contained thereon.

For these and other reasons, stents and stent delivery catheters are needed which enable the customization of stent length in situ, and the treatment of multiple lesions of various sizes, without requiring removal of the delivery catheter from the patient. Such stents and stent delivery catheters should be capable of treating lesions of particularly long length and lesions in curved regions of a vessel, and should be highly flexible to conform to vessel shape and movement. Such stent delivery catheters should further be of minimal cross-sectional profile and should be highly flexible for endovascular positioning through tortuous vascular pathways.

BRIEF SUMMARY OF THE INVENTION

The present invention provides devices and methods for delivering prostheses, particularly stents, into body lumens. In several preferred embodiments, the devices and methods facilitate accurate control of the working or deployed length of a multi-segment stent or other prosthesis by providing valve members that effectively and consistently separate a first prosthesis segment or plurality of prosthesis segments from a second prosthesis segment or plurality of prosthesis segments carried by the delivery device. Preferably, the valve members function actively, by selectively moving between a contracted configuration in which the valve member allows movement of prostheses out of an outer sheath, and an extended configuration in which the valve member inhibits movement of prostheses out of the sheath.

The methods and systems described herein are suitable for use in relation to prosthesis placement, such as stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. Stents and other similar prostheses commonly comprise an open lattice structure, typically formed from a malleable or elastic metal, a polymeric material, or other similar material or combination of materials. When formed from a malleable metal, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. When formed of a polymeric material, the lattice structures will be deployed by either of the foregoing processes or possibly formed in situ. When the stent or lattice structures are covered with a fabric or polymeric membrane covering, they are commonly referred to as grafts. Grafts may be used for the treatment of aneurysms or other conditions which require placement of a non-permeable or semi-permeable barrier at the treatment site. The terms "prosthesis" and "prostheses" refer broadly to all radially expansible stents, grafts, and other scaffold-like structures which are intended for deployment within body lumens.

The stents and other prostheses described herein may have any of a variety of common constructions, including helical structures, counterwound helical structures, expandable diamond structures, serpentine structures, or the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337. Preferred structures are described, for example, in co-owned pending U.S. patent application Ser. No. 10/738,666, filed Dec. 16, 2003, and U.S. patent application Ser. No. 10/306,813, filed Nov. 27, 2002, each of which is incorporated herein by reference.

In the practice of the devices and methods described herein, the stents that are deployed may have a length of 1 mm or greater, usually 2 mm or greater, and typically of 3 mm or greater, usually being in the range from 1 mm to 100 mm, typically from 2 mm to 50 mm, more typically from 2 mm to 25 mm, and usually from 3 mm to 20 mm. The use of such short stent lengths is advantageous since multiple stents are to be employed.

The methods and apparatus described herein will provide for deployment of a plurality of stents or other prostheses, usually including at least two stents, from a common stent delivery catheter. Usually, the number of delivered stents will be in the range from 2 to 50, typically from 3 to 30, and most typically from 5 to 25. As more stents are placed on the delivery catheter, the individual stent length will often be somewhat less, although this is not necessarily the case in all instances. The multiple prostheses may be deployed individually or in groups of two or more at single or multiple spaced-apart locations in the body lumen or lumens.

In a first aspect of the present invention, a method for stenting an extended length of a body lumen comprises introducing a catheter carrying a plurality of, usually at least two, discrete stent segments to the body lumen. Usually, the introduction is percutaneous and, in the case of intravascular delivery, uses a conventional introduction technique, such as the Seldinger technique. After reaching a target location, at least a first stent segment is released from the catheter at that first location. The catheter is then repositioned to a second location, and at least a second stent segment is released from the catheter at the second location. The catheter is then repositioned to a third location, and at least a third stent segment is released from the catheter at the third location.

In addition to deploying stents and other prostheses at spaced-apart locations within a blood vessel or other body lumen, the methods and apparatus in the present invention can be used for delivering one, two, three, or more discrete stents or other prosthesis segments contiguously at a single location within the body lumen. In this way, the length of the prosthesis which is implanted can be selected and modified to accommodate the length of the vessel to be treated. It will be appreciated that with systems which carry 10, 20, 30 or more quite short prostheses or prosthesis segments, the length of the lumen being treated can be tailored very closely from very short to very long with the selectable intervals depending on the length of the prosthesis or prosthesis segment.

The deployment steps can, of course, be repeated a sufficient number of times so that all or at least more of the stents carried by the delivery catheter are delivered to and deployed within the body lumen. A particular advantage of this delivery method is that the discrete stents may be distributed along extended lengths of the body lumen, typically in the range from 1 cm to 2 cm, often in the range from 1 cm to 5 cm, and in many instances even longer. Additionally, the stents may be delivered so as to avoid side branches or other regions where placement of the stent is undesirable. Moreover, with the use of drug-coated stents, it may be possible to place the stents apart by discrete distances, typically from one-half to one millimeter (mm), while still achieving vessel patency and hyperplasia inhibition.

Releasing of the stents from the catheter may be achieved using a balloon to cause balloon expansion of the stent. Alternatively, release of the stent may be achieved by radially constraining an elastic or self-expanding stent within a lumen of the delivery catheter and selectively advancing the stent from the catheter and/or retracting the catheter from over the stent. In several embodiments, a sheath over the stents includes a valve member, or "stent valve," which allows stents to be separated so that a balloon can more accurately inflate deployed stents while other stents remain within the sheath.

In preferred embodiments, the stents are coated with at least one agent, such as an agent which inhibits hyperplasia. The agent may be biologically active or inert. Particular biologically active agents include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Biologically inert agents include polyethylene glycol (PEG), collagen, polyglycolic acids (PGA), ceramic material, titanium, gold and the like.

In another aspect, the present invention comprises catheters and apparatus for stenting extended lengths of a body lumen, particularly a blood vessel. The catheters comprise a catheter body having a proximal end and a distal end. At least two discrete stents are carried at or near a distal end of the catheter body. By "discrete," it is meant that the stents are unconnected and can be deployed from the catheter in an unattached manner. (The delivery of attached prostheses is described below.) Deployment of such discrete stents permits the individual stents to be placed at spaced-apart target locations or immediately adjacently within the blood vessel or other body lumen. The catheters further comprise deployment means for deploying the individual stents from the catheter body. For example, the deployment means may comprise one or more balloons for placement and radial expansion of the stents. Alternatively, the deployment means may comprise a pusher or other device for advancing self-expanding stents from the distal end of the catheter body and/or a sheath for selectively retracting over the stents to permit self-expansion. In exemplary embodiments, the catheters will carry at least two discrete stents, at least five discrete stents, and as many as 10 discrete stents, or in some cases, as many as 30 or more discrete stents.

In a particular embodiment, the catheter comprises a single balloon which is reciprocatively mounted within the catheter body and adapted for receiving individual stents thereover. A pusher or other device for successively and controllably loading individual or multiple stents over the balloon is also provided. In this way, the catheter may carry multiple stents and employ the single balloon for positioning and expansion of the stents.

In further embodiments, the stents of the present invention are composed at least partly of a bioabsorbable material, such as polyethylene glycol (PEG), collagen, gelatin, polyglycolic acids (PGA), polylactic acids (PLA), and the like. Optionally, one or more bioactive substances are dispersed in the bioabsorbable material such that the bioactive substance will be released over time as the bioabsorbable material degrades. In a particular embodiment, the bioabsorbable material is formed on or within a scaffold composed on a non-bioabsorbable material, typically stainless steel, NiTi alloy, or other conventional stent metal material. Other materials, such as gold (e.g., pure or nearly pure gold), platinum, or the like, may also be used.

In a further aspect of the present invention, a catheter for delivering a plurality of expansible prostheses to a body lumen comprises a catheter body, a sheath, and a plurality of radially expansible prostheses. The catheter body has a proximal end and a distal end, and the sheath is coaxially disposed over the catheter body with the prostheses positionable in an annular space between the inside of the sheath and the exterior of the catheter body. The sheath is preferably retractable relative to the catheter body so that the prostheses may be advanced beyond a distal end of the sheath. Usually, the catheter will further comprise a pusher tube disposed coaxially over the catheter body and within an interior lumen of the sheath. A distal end of the pusher tube will engage a proximal end of the proximal-most prosthesis so that the pusher tube can be distally advanced relative to the sheath to selectively push or deploy individual prostheses from the sheath. Often, such deployment is achieved by holding the pusher tube and prostheses substantially stationary relative to the body lumen while the sheath is retracted proximally to release or deploy the prostheses.

Usually, at least a distal portion of the sheath will have a greater column strength than that of a distal portion of the catheter body. Additionally or alternatively, the pusher tube may also have a greater column strength than a distal portion of a catheter body. By providing column strength in the outer most portion of the catheter, i.e., the sheath, and optionally the pusher tube, the overall column strength of the catheter can be increased with a minimum increase in its diameter or profile. It will be appreciated that low profile catheters are highly advantageous for accessing remote regions of the vasculature, particularly the small coronary and cerebral arteries. Using the preferred constructions of the present invention, catheters having diameters 2 mm or less, and in some instances as low as 1 mm or less, can be achieved. The constructions will, of course, also be suitable for larger diameter catheters for use in the peripheral and other larger blood vessels.

The catheter of the present invention will preferably carry at least two prostheses, more preferably carrying at least three prostheses, and often carrying a greater number of prostheses as set forth above in connection with other embodiments. The prostheses will typically be arranged in an end-to-end manner either with or without a physical linkage therebetween. The physical linkage may comprise a frangible component which must be mechanically broken or alternatively may comprise a pair of coupling elements which fit together and which may be separated without any material breakage. Frangible coupling elements will usually comprise a strut, bar, spring, or similar connecting link and will optionally be scored, notched, or otherwise adapted to break along a particular line when a suitable mechanical force is applied. Exemplary separable coupling elements include male and female elements, such as a rod and tube which may be axially separated, a tab and receptacle which may be radially separated, and the like.

In specific embodiments of the catheter, the catheter body may comprise an expansion element, such as an inflatable balloon, near its distal end. The expansion element will be positionable distal to the retractable sheath so that it can be used to regularly expand one or more of the prostheses. For example, the inflatable balloon may carry multiple prostheses on its outer surface so that sheath retraction can expose one, two, three, or more of the prostheses. The remaining prostheses will continue to be covered by the sheath. When inflating the balloon, however, only that portion of the balloon and those prostheses carried on the exposed portion of the balloon will be inflated. The remaining (proximal) portion of the balloon will continue to be constrained by the sheath so that neither the balloon nor the prostheses covered by the sheath will be expanded. In this way, any preselected number of the individual prostheses may be expanded at one time, while the remaining prostheses are protected and unexpanded, remaining available for subsequent expansion using the balloon.

The invention further provides prosthesis delivery catheters and systems that include valve members to enable the selective deployment of a desired number of prostheses at a treatment site while retaining other prostheses within the device for deployment at other locations. In general, these catheters and systems will include a sheath having a proximal end, a distal end, an opening at the distal end, and a passage in communication with the opening adapted to contain a plurality of prostheses. A valve member is disposed near the distal end of the sheath adapted for selectively retaining at least one prosthesis within the passage.

The valve member may function either actively or passively. In passive configurations, the valve member prevents the prosthesis from exiting the passage under a first force and allows the prosthesis to exit the passage under a second force higher than the first force. In those embodiments for delivering balloon-expandable stents, an expandable member is slidably positioned in the sheath and the prostheses are positionable on the expandable member. Typically, the expandable member is an inflatable balloon mounted to an elongated catheter shaft. A pusher is preferably slidably mounted in the sheath and is adapted to exert a force on the prostheses to advance them distally through the sheath. In preferred embodiments, the valve member will be adapted to prevent the prostheses from being advanced out of the sheath unless sufficient force is exerted on the pusher. The distal movement of the expandable member relative to the prostheses in the sheath will not itself be sufficient to advance the prostheses past the valve member unless the pusher is also pushed against the prostheses. In this way, the desired number of prostheses can be advanced out of the sheath by pushing both the expandable member and the pusher together while holding the sheath in position (or by pulling the sheath back while maintaining the expandable member and the pusher in position). The expandable member and the prostheses to be deployed can then be advanced further relative to the sheath a desired distance without causing additional prostheses to move out of the sheath.

It should be understood that the movements of the sheath, expandable member, pusher tube and prostheses are relative and in most embodiments of the invention, either retracting the sheath proximally relative to the expandable member and pusher tube, or advancing the expandable member and pusher tube distally relative to the sheath, or a combination thereof, may be practiced without departing from the principles of the invention. Therefore, when the movement of one component relative to another component is described herein, it should be interpreted to mean holding one component in position while moving the other, or vice versa, or moving both components relative to each other.

The present invention includes several embodiments of active valve members. In active embodiments, the valve member is selectively movable between a contracted configuration in which the valve member allows movement of prostheses out of the sheath, and an extended configuration in which the valve member inhibits movement of prostheses out of the sheath. In these embodiments, the valve member may comprise an inflatable member that can be selectively inflated and deflated, a mechanical member that is physically manipulated between an open position and an engaged position, or an energy-activated mechanism that changes shape or other orientation in response to energy inputs. Further, an active valve member may comprise a piezoelectric crystal member that is selectively moveable between an engaged position and an open position in response to a drive voltage.

In several embodiments, the valve member comprises an inflatable member that can be selectively inflated and deflated. When inflated, the valve member increases in size, thereby causing a portion of the valve member to engage one or more stent segments located radially inward of the location of the valve member. The inflatable member may be located on the interior surface of the outer sheath near its distal end, or it may be formed integrally within the outer sheath near its distal end. In the latter case, the inflatable member may be laminated between two or more layers forming the distal portion of the outer sheath, in which case the outer sheath delaminates when the inflatable member is inflated.

In other embodiments, the valve member also includes a spacer member that is at least as long as the combined length of the column of stent segments carried by the catheter. The spacer member is preferably generally tubular, and is formed of a material having sufficient strength to substantially isolate forces applied from the exterior of the spacer member from members located on the interior of the spacer member, and vice versa. The tubular spacer member is preferably located adjacent to and just proximal of the column of stent segments. The spacer member is also preferably disposed between the inflatable valve and the inflation balloon used to expand the stent segments for deployment. In this way, the spacer member prevents unwanted interference between the inflatable valve and the inflation balloon used to deploy the stent segments.

In several other embodiments, the valve member comprises a mechanical valve member that is physically manipulated between an open position and an engaged position. In these embodiments, the valve member preferably includes an impinger member that is selectively moved from a first state in which it does not engage any of the stent segments carried by the catheter, and a second state in which it engages at least one of the stent segments. The impinger member may constitute all or a portion of the valve. In a particularly preferred form, the impinger member is formed of or coated with a material that substantially minimizes the possibility of damaging the underlying stent segments or any coatings carried by the stent segments. For example, the impinger member may be formed of or coated by a relatively soft material, a low-friction material, a material having both properties, or a material having other properties that provide protection to the underlying stent segments.

Actuation of the impinger member may be provided by any suitable mechanism. For example, the impinger may be formed of a material or constructed so as to deflect radially inward when a force is applied to bring the longitudinal ends of the impinger closer to one another. This is achieved in several embodiments by locating the impinger between a pair of stop members, and then actuating the impinger by moving the stop members closer to one another. Suitable materials and constructions include low durometer materials such as rubbers or thermoelastomers, braided materials, or the like. Similarly, the impinger may also be formed of a material or otherwise constructed so as to deflect radially inward when the longitudinal ends of the impinger are forced apart. This is achieved in several other embodiments by locating the impinger between a pair of stop members, and then actuating the impinger by moving the stop members farther apart from one another. Suitable materials and constructions include braided materials that impinge in the manner of a "Chinese handcuff" known to those skilled in the art. In each of the foregoing embodiments, the actuation is preferably facilitated by having a pull wire attached to one or both of the stop members.

Alternatively, actuation of the impinger may be caused by application of energy, such as electrical energy. In several embodiments, electrical energy (e.g., application of a voltage) directly causes actuation of the valve member. In one such embodiment, the valve is formed of an electroactive polymer artificial muscle material known to those skilled in the art. Upon activation by applying a voltage, the artificial muscle material contracts, thereby causing an impinger member to engage one or more underlying stent segments. In another embodiment, the valve includes a piezoelectric material. Upon activation by application of a voltage, the piezoelectric material deforms, thereby causing an impinger member to engage one or more underlying stent segments. Other electrically operated valve members are also possible.

In several other preferred embodiments, electrical or other energy is converted to heat energy, which is used to actuate a valve formed of a heat-actuated shape memory material. Typical shape memory materials include shape memory metals and metal alloys (e.g., nickel titanium alloy), shape memory polymer materials, blends of these materials, and others. In several preferred embodiments, the energy actuated valve member is substantially in the form of a cylinder or tube that constricts upon actuation, thereby impinging upon one or more stent segments located radially inward of the cylinder or tube. The cylindrical or tubular portion of the valve member may comprise one of several constructions, each of which is configured so as to compress, contract, constrict, restrict, impinge, or otherwise engage one or more of the underlying stent segments.

In several embodiments, the valve includes one or more ring members interconnected by a plurality of struts, at least one of which struts is configured to deform radially inward to impinge upon an underlying stent segment. In one such embodiment, a distal ring and a proximal ring are connected to one another by a plurality of longitudinal struts. At least one strut is formed of a shape memory material that contracts upon actuation. At least one other of the struts is constructed so as to deflect radially inward when the proximal and distal rings are drawn toward one another under the influence of the contracting strut. In another embodiment, a compression ring formed of a shape memory material substantially surrounds a plurality of cantilevered struts. Constriction of the compression ring causes the struts to deflect radially inward to thereby impinge upon one or more of the underlying stent segments.

In several other embodiments, the valve member comprises one or more "C"-shaped tubular members that are formed of a shape memory material. In a first, expanded state, the C-shaped members allow passage of the stent segments therethrough. In a second, contracted state, the C-shaped members impinge upon the underlying stent segment(s). In other embodiments, the valve member is in the form of a Touhy-Borst type of valve, including a retainer, an elastic expander, and a driver that is of a size, shape, and orientation to selectively compress the expander within the retainer. This compression causes the expander to deform, a portion of the expander impinging radially inward upon one or more of the stent segments. Preferably, the driver is formed of a shape memory material that is adapted to apply a compressive force against the expander when it is actuated. In yet another embodiment, a fixed retainer is adapted to substantially surround an expansion element. The expansion element includes at least one finger that deflects radially inward when the expansion element is forced against the inner, conically-shaped surface of the retainer. In this embodiment, the expansion element is preferably formed of a shape memory material that is adapted to engage and apply a force against the retainer upon actuation.

In still further embodiments, the valve includes a pair of opposed torsion springs attached end-to-end. At least one of the torsion springs is formed of a shape memory material that is shape set such that, upon actuation, the spring rotates about its longitudinal axis to thereby constrict upon one or more of the underlying stent segments. The second spring is preferably formed of a material that is adapted to store potential energy created by the deformation of the first spring, which potential energy is released during the process of resetting the first spring when actuation is stopped. In yet another embodiment, the valve member comprises a pair of concentric tubular members, in which one of the tubular members is formed of a shape memory material adapted to contract upon actuation, and the other tubular member is formed of a superelastic material adapted to store potential energy when it is contracted under the influence of the other tubular member. The stored potential energy is then released after actuation is stopped in order to assist with resetting the first tubular member to its original shape and size.

Further aspects of the nature and advantages of the invention will become apparent from the detailed description below taken in conjunction with the drawings.

BRIEF DESCRIPTION OF THE DRAWINGS

FIG. 1 is a perspective view of a stent delivery catheter according to the invention with sheath retracted and expandable member inflated.

FIG. 2A is a side cross-section of a distal portion of the stent delivery catheter of FIG. 1 with expandable member deflated and sheath advanced distally.

FIG. 3 is a transverse cross-section through line 3-3 of FIG. 2A.

FIG. 4 is a transverse cross-section through line 4-4 of FIG. 2A.

FIGS. 5A-5E are side cut-away views of the stent delivery catheter of the invention positioned in a vessel, illustrating various steps of delivering a prosthesis according to the method of the invention.

FIG. 6 is a side view of a pusher tube.

FIG. 6A is a cross-sectional view of the pusher tube of FIG. 6 taken at line A-A.

FIG. 18 is a cross-sectional view of a stent delivery catheter having another mechanical stent valve.

FIG. 35 is a cross-sectional view of an energy actuated stent valve.

FIGS. 36A-D are cross-sectional views of a piezo crystal actuated stent valve.

FIGS. 38A-B are side views of a stent delivery catheter having another embodiment of release wires attached to stent segments.

DETAILED DESCRIPTION OF THE INVENTION

Figure 2B:
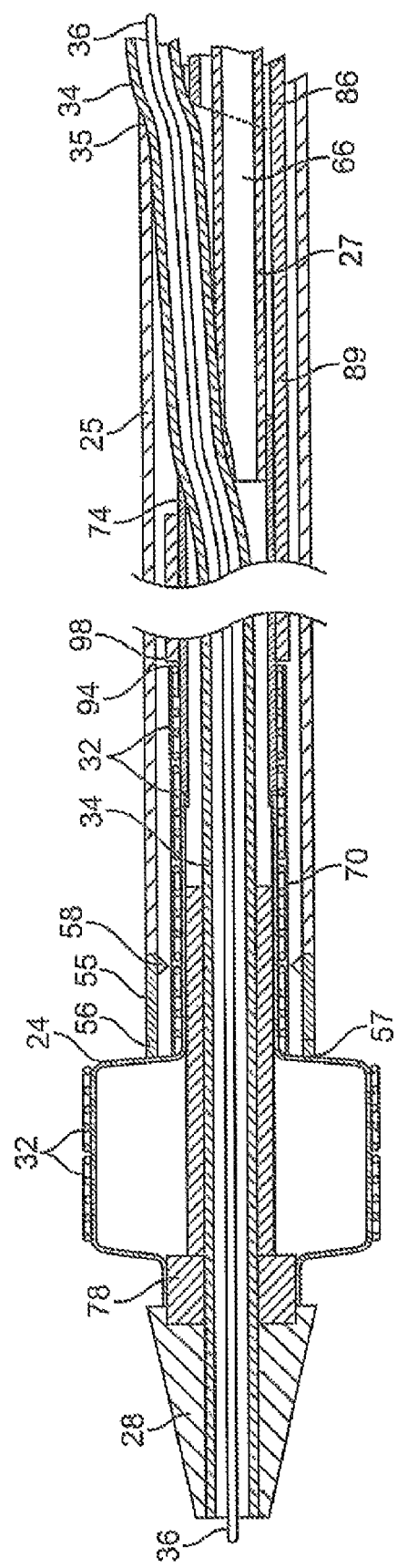
FIG. 2B is a side cross-section of a distal portion of the stent delivery catheter of FIG. 1 with expandable member inflated and sheath retracted.

The present application relates generally to co-pending U.S. patent application Ser. No. 11/538,904 filed Oct. 5, 2006 and to 10/412,714 filed Apr. 10, 2003, each of which application is hereby incorporated by reference.

A first embodiment of a stent delivery catheter according to present invention is illustrated in FIG. 1. The stent delivery catheter 20 includes a catheter body 22 comprising an outer sheath 25 slidably disposed over an inner shaft 27 (not shown in FIG. 1). An expandable member 24, preferably an inflatable balloon (shown in an inflated configuration), is mounted to the inner shaft 27 and is exposed by retracting the sheath 25 relative to the inner shaft 27. A tapered nosecone 28, composed of a soft elastomeric material to reduce trauma to the vessel during advancement of the device, is mounted distally of expandable member 24. A stent 30, which preferably comprises a plurality of separate or separable stent segments 32, is disposed on the expandable member 24 for expansion therewith. A guidewire tube 34 is slidably positioned through a guidewire tube exit port 35 in the sheath 25 proximal to the expandable member 24. A guidewire 36 is positioned slidably through the guidewire tube 34, the expandable member 24, and the nosecone 28 and extends distally thereof.

Additional details of the construction, operation, and features of several preferred stent delivery catheters are described in co-pending U.S. Patent Application Ser. No. 60/688,896, filed Jun. 8, 2005, entitled "Apparatus and Methods for Deployment of Multiple Custom-Length Prostheses (P)," which application is hereby incorporated herein by reference. Embodiments of other preferred stent delivery catheters and details concerning their structure and operation are described in co-pending U.S. application Ser. No. 10/637,713, filed Aug. 8, 2003, entitled "Apparatus and Methods for Deployment of Vascular Prostheses," which application is also hereby incorporated herein by reference.

A handle 38 is attached to a proximal end 23 of the sheath 25. The handle 38 performs several functions, including operating and controlling the catheter body 22 and the components included in the catheter body. Various embodiments of a preferred handle and additional details concerning its structure and operation are described in co-pending U.S. patent application Ser. No. 11/148,713, filed Jun. 8, 2005, entitled "Devices and Methods for Operating and Controlling Interventional Apparatus," which application is hereby incorporated herein by reference. Embodiments of other preferred handles and details concerning their structure and operation are described in co-pending U.S. application Ser. No. 10/746,466, filed Dec. 23, 2003, entitled "Devices and Methods for Controlling and Indicating the Length of an Interventional Element," which application is also hereby incorporated herein by reference.

The handle 38 includes a housing 39 that encloses the internal components of the handle. The inner shaft 27 is preferably fixed to the handle, while the outer sheath 25 is able to be retracted and advanced relative to the handle 38. An adaptor 42 is attached to the handle 38 at its proximal end, and is fluidly coupled to the inner shaft 27 in the interior of the housing of the handle 38. The adaptor 42 is configured to be fluidly coupled to an inflation device, which may be any commercially available balloon inflation device such as those sold under the trade name "Indeflator™", available from Guidant Corp. of Santa Clara, Calif. The adaptor is in fluid communication with the expandable member 24 via an inflation lumen in the inner shaft 27 to enable inflation of the expandable member 24.

The outer sheath 25 and guidewire 36 each extend through a slider assembly 50 located on the catheter body 22 at a point between its proximal and distal ends. The slider assembly 50 is adapted for insertion into and sealing within a hemostatic valve, such as on an introducer sheath or guiding catheter, while allowing relative movement of the outer sheath 25 relative to slider assembly 50. The slider assembly 50 includes a slider tube 51, a slider body 52, and a slider cap 53.

Referring now to FIGS. 2A-2B, 3 and 4, which show a distal portion of the stent delivery catheter in cross-section, it may be seen that the sheath 25 may be extended up to the nosecone 28 to fully surround the expandable member 24 and the stent segments 32. A garage 55 is attached to the outer sheath 25 at the distal end 57 of the sheath. The garage 55 is a generally cylindrical member having a relatively high circumferential strength such that it is able to prevent the expandable member 24 from inflating when the garage is extended over the inflatable member 24. The garage 55 preferably has a length at least as long as one of the stent segments 32 carried by the catheter, but preferably less than the combined length of two such stent segments. A radiopaque marker 56 is preferably formed integrally with or attached to the distal end of the garage 55 to facilitate visualization of the position of the sheath 25 using fluoroscopy. The radiopaque marker 56 may have an axial length selected to provide a visual reference for determining the appropriate distance for stent segment separation, e.g., 2-4 mm, as described below.

The outer sheath 25 illustrated in the foregoing Figures further includes a passive valve member 58 within the garage 55 preferably spaced proximally from the distal end 57 a distance equal to, slightly larger than, or slightly smaller than the length of one of the stent segments 32. For example, in a preferred embodiment, each stent segment 32 has a length of about 4 mm, and the valve member 58 is located approximately 5 mm from the distal end 57 of the sheath or the distal end of the garage member 55. In other embodiments, the valve member 58 may be spaced from the distal end 57 a distance equal to about ¼-¾ of the length of one stent segment 32, more preferably one-half the length of one stent segment 32. The passive valve member 58 may comprise a necked-down circumferential waist or inwardly extending ring-shaped flange configured to frictionally engage the stent segments 32 and thereby restrict the sliding movement of the stent segments 32 distally relative to the sheath 25. The flange may be a polymeric or metallic material integrally formed with the sheath 25 or, preferably, with the garage 55, or a separate annular member bonded or otherwise mounted to the interior of the sheath 25 or the garage 55. The geometry of the flange may be toroidal with a circular cross-section (like an O-ring) or it may have another cross-sectional shape such as triangular, trapezoidal, or pyramidal. Preferably, the flange is a polymer such as silicone or urethane that is sufficiently soft, compliant, and resilient to provide frictional engagement with the stent segments 32 without damaging the stent segment or any coating deposited thereon. The passive valve member 58 will extend radially inwardly a sufficient distance to engage the exterior of the stent segments 32 with sufficient force to allow the line of stent segments 32 remaining within the sheath 25 to be retracted proximally with the sheath 25 so as to create spacing relative to those stent segments disposed distally of the sheath 25 for deployment. At the same time, the passive valve member 58 should not exert so much force that it removes or damages the coating on the exterior surface of the stent segments 32 as the sheath 25 is retracted relative to the stent segments to expose a desired number of stent segments 32. In a preferred embodiment, the stent segments 32 have an outer diameter of about 0.030-0.050 in. (including coating) and the sheath 25 and the garage 55 have inner diameter 0.031-0.051 in. so as to provide clearance of about 0.001 in. with the stent segments 32. The passive valve member 58 has a preferred inner diameter about 0.003-0.008 in. less than that of the garage 55, or about 0.023-0.048", so as to provide an interference fit with the stent segments 32. The passive valve member 58 will preferably exert a force of about 0.2-5 lbs. on a stent segment 32 positioned within it. Various embodiments of passive valve members 58 and some active valve members are described in copending application Ser. No. 10/412,714, Filed Apr. 10, 2003, which is incorporated herein by reference.

As thus described, the sheath 25 has a distal extremity 62 configured to surround the expandable member 24 and the stent segments 32 disposed thereon when in an unexpanded configuration. The distal extremity 62 extends proximally to a junction 63, preferably aligned with the location of the guidewire tube exit port 35, where the distal extremity 62 is joined to a proximal extremity 64 that extends proximally to the handle 38 (see FIG. 1). In a preferred embodiment, the distal extremity 62 has a length of about 15-35 cm and the proximal extremity 64 as a length of about 100-125 cm. The proximal extremity 64 may be constructed of a variety of biocompatible polymers, metals, or polymer/metal composites preferably being stainless steel or Nitinol. The distal extremity 62 may be a polymer such as PTFE, FEP, polyimide, nylon, or Pebax, or combinations of any of these materials. In a preferred form, the distal extremity 62 comprises a composite of nylon, PTFE, and polyimide. The distal extremity is preferably reinforced with a metallic or polymeric braid to resist radial expansion when expandable member 24 is expanded. The sheath 25 may further have a liner surrounding its interior of low friction material such as PTFE to facilitate relative motion of the sheath 25, the stent segments 32, and the pusher tube 86.

Preferably, the proximal extremity 64 has a smaller transverse dimension than the distal extremity 62 to accommodate the added width of the guidewire tube 34 within the vessel lumen, as well as to maximize flexibility and to minimize profile. In one embodiment, shown in FIG. 3, the distal extremity 62 is a tubular member having a first outer diameter, preferably about 1.0-1.5 mm, and the proximal extremity 64 is a tubular member having a second, smaller outer diameter, preferably about 0.7-1.0 mm. At the junction of the proximal extremity 64 with the distal extremity 62, a proximally-facing crescent-shaped opening 65 is formed between the two tubular members that creates the guidewire tube exit port 35. Excess space within the crescent-shaped opening 65 may be filled with a filler material such as adhesive or a polymeric material (e.g., Pebax).

The guidewire tube 34 is slidably positioned through the guidewire tube exit port 35. The guidewire tube exit port 35 may be configured to provide a total or partial fluid seal around the periphery of the guidewire tube 34 to limit blood flow into the interior of the sheath 25 and to limit leakage of saline (or other flushing fluid) out of the sheath 25. This may be accomplished by sizing the guidewire tube exit port 35 appropriately so as to form a fairly tight frictional seal around the guidewire tube 34 while still allowing the sliding motion thereof relative to the sheath 25. Alternatively, an annular sealing ring may be mounted in the guidewire tube exit port 35 to provide the desired seal. Preferably, however, the guidewire tube exit port 35 is not totally fluid sealed, so as to provide a slight leakage or fluid flow to provide the ability to flush the distal extremity 62 of the catheter.

The guidewire tube exit port 35 will be positioned to provide optimal tracking of the stent delivery catheter 20 through the vasculature and maximizing the ease with which the catheter can be inserted onto and removed from a guidewire to facilitate catheter exchanges. Usually, the guidewire tube exit port 35 will be positioned at a location proximal to the expandable member 24 when the sheath 25 is extended fully distally up to the nosecone 28, but a distance of no more than one-half the length of the sheath 25 from the distal end 57. In preferred embodiments for coronary applications, the guidewire tube exit port 35 is spaced proximally a distance of about 20-35 cm from the distal end 57 of the sheath 25.

The guidewire tube 34 should extend proximally from the guidewire tube exit port 35 a distance at least as long as the longest possible stent that may be deployed, e.g., 30-200 mm depending upon the application, to allow for retraction of the sheath 25 that distance while retaining a portion of the guidewire tube 34 external to the sheath 25. Preferably the guidewire tube 34 extends proximally a distance of about 35 to about 70 mm from the guidewire tube exit port 35 when the sheath 25 is in a fully distal position, with the proximal end thereof disposed a distance of about 23-50 cm from the distal tip of the nosecone 28. In applications in which the stent delivery catheter 20 is to be positioned through a guiding catheter, the proximal end of the guidewire tube 34 will preferably be positioned so as to be within the guiding catheter when the expandable member 24 is positioned at the target site for stent deployment. The guidewire tube 34 is preferably a highly flexible polymer such as PTFE, FEP, polyimide, or Pebax, and may optionally have a metal or polymer braid or fiber embedded in it to increase kink-resistance and tensile strength.

The inner shaft 27 forms an inflation lumen 66 that is in communication with the interior of the expandable member 24. The inner shaft 27 may be formed of a polymer material such as PTFE, FEP, polyimide, or Pebax, or the inner shaft 27 may be a metal such as stainless steel or Nitinol.

The expandable member 24 has an expandable balloon member 70 that is joined to a non-expandable tubular leg 72. The expandable balloon member 70 is a semi-compliant polymer such as Pebax, polyurethane, or Nylon. Non-compliant, fully elastic, or other materials such as PTFE may also be used. Preferably, the compliance of the balloon member allows the expanded diameter of the balloon member 70 to be adjusted by selecting the appropriate inflation pressure delivered thereto, thereby allowing customization of the deployed diameter of stent segments 32. For example, in one embodiment, the balloon member 70 may be inflated to a pressure of between about 5 and about 12 atmospheres, allowing the deployed stent diameter to be adjusted from about 2.0 mm to 4.0 mm. Of course, larger and smaller stent diameters are also possible by utilizing appropriate stent geometry and applying suitable inflation pressures.

The tubular leg 72 is preferably a polymer such as polyimide, PTFE, FEP, polyurethane, or Pebax and may optionally be reinforced with a metal or polymer braid or metal or polymer fibers. The tubular leg 72 has an open proximal end 74 through which the guidewire tube 34 extends. The proximal end 74 of the tubular leg 72 is fixed to the distal end 68 of the inner shaft 27 and to the guidewire tube 34, forming a fluid-tight seal. The guidewire tube 34 passes through the interior of the balloon member 70 and is mounted to the nosecone 28, thereby providing a passage through the distal portion of the catheter body 22 through which the guidewire 36 may pass. The balloon member 70 has a distal end 76 that extends over an annular stop 78, which is mounted to the distal end of the guidewire tube 34 and/or the nosecone 28. The distal end 76 of the balloon member 70 may be bonded to the stop 78, the guidewire tube 34, and/or the nosecone 28. The stop 78 has a size and shape selected to engage the stent segment 32 and provide a stop against which the stent segments 32 can be located in the ideal deployment position without being pushed beyond the distal end of the balloon member 70. Additional details concerning stent stops suitable for use in the devices and methods described herein are disclosed in U.S. patent application Ser. No. 10/884,616, filed Jul. 2, 2004, which is hereby incorporated by reference herein.

Optionally, within the interior of the balloon member 70 an annular base member 80 is mounted to the guidewire tube 34 and has a diameter selected to urge the balloon member 70 against the stent segments 32 in their unexpanded configuration, thereby providing frictional engagement with the stent segments 32. This helps to limit unintended sliding movement of the stent segments 32 on the balloon member 70. The base member 80 may be made of a soft elastomer, foam, or other compressible material.

The stent segments 32 are slidably positioned over the balloon member 70. Depending upon the number of stent segments 32 loaded in the stent delivery catheter 20, the stent segments 32 may be positioned over both the balloon member 70 and the tubular leg 72. In an exemplary embodiment, each stent segment is about 2-20 mm in length, more preferably 2-8 mm in length, and 3-50 stent segments may be positioned end-to-end in a line over the balloon member 70 and the tubular leg 72. The stent segments 32 preferably are in direct contact with each other, but alternatively separate spacing elements may be disposed between adjacent stent segments, the spacing elements being movable with the stent segments along the balloon member 70.

The stent segments 32 are preferably a malleable metal so as to be plastically deformable by the expandable member 24 as they are expanded to the desired diameter in the vessel. Alternatively, the stent segments 32 may be formed of an elastic or super elastic shape memory material such as Nitinol so as to self-expand upon release into the vessel by retraction of sheath 25. The stent segments 32 may also be composed of polymers or other suitable biocompatible materials including bioabsorbable or bioerodable materials. In self-expanding embodiments, the expandable member 24 may be eliminated or may be used for predilatation of a lesion prior to stent deployment or for augmenting the expansion of the self-expanding stent segments.

In preferred embodiments, the stent segments 32 are coated with a drug that inhibits restenosis, such as Rapamycin, Paclitaxel, Biolimus A9 (available from BioSensors International), analogs, prodrugs, or derivatives of the foregoing, or other suitable agent, preferably carried in a durable or bioerodable polymeric or other suitable carrier material. Alternatively, the stent segments 32 may be coated with other types of drugs and therapeutic materials such as antibiotics, thrombolytics, antithrombotics, anti-inflammatories, cytotoxic agents, antiproliferative agents, vasodilators, gene therapy agents, radioactive agents, immunosuppressants, and chemotherapeutics. Several preferred therapeutic materials are described in U.S. Pat. No. 6,939,376, entitled "Drug-Delivery Endovascular Stent and Method of Forming the Same," issued Sep. 6, 2005, which patent is hereby incorporated by reference herein. Such materials may be coated over all or a portion of the surface of the stent segments 32, or the stent segments 32 may include apertures, holes, channels, pores, or other features in which such materials may be deposited. Methods for coating stent segments 32 are described in the foregoing published patent application. Various other coating methods known in the art may also be used, including syringe application, spraying, dipping, inkjet printing-type technology, and the like.

The stent segments 32 may have a variety of configurations, including those described in copending U.S. Patent Application Ser. No. 60/688,896, filed Jun. 8, 2005, and Ser. No. 10/738,666, filed Dec. 16, 2003, each of which is incorporated herein by reference. The stent segments 32 are preferably completely separate from one another without any interconnections, but alternatively may have couplings between two or more adjacent segments which permit flexion between the segments. As a further alternative, one or more adjacent stent segments may be connected by separable or frangible couplings that are separated prior to or upon deployment, as described in co-pending U.S. patent application Ser. No. 10/306,813, filed Nov. 27, 2002, which is also incorporated herein by reference.

A pusher tube 86 is slidably disposed over the inner shaft 27. The structure of the pusher tube 86 is illustrated in FIG. 6, and its location within the catheter body 22 is best shown in FIGS. 2A-B. The pusher tube 86 contains three primary sections, a distal extension 88, a ribbon portion 89, and a proximal portion 90. The proximal portion 90 extends from the handle 38 over the inner shaft 27 and to the ribbon portion 89. The proximal portion 90 is preferably formed of a tubular material to provide high column strength but adequate flexibility to extend through the vasculature from an access site to the coronary ostia or other target vascular region. A preferred material is stainless steel hypotube. The ribbon portion 89 of the pusher tube corresponds with the location of the guidewire exit port 35 on the outer sheath 25. The ribbon portion 89 is formed of a partial-tube, see, e.g., FIG. 6A, in order to provide an opening to allow the guidewire tube 34 to pass through to the exit port 35. The proximal portion of the ribbon portion 89 is formed out of the same tubular material, that makes up the proximal portion 90 of the pusher tube, e.g., stainless steel hypotube.

The proximal portion of the ribbon portion 89 is joined to the distal portion of the ribbon 89, such as by a weld 91 or the ribbon portion and proximal portion may be formed from the same hypotube which is laser cut in the appropriate geometry. The distal extension 88 is preferably formed of a slotted tube of rigid material, such as stainless steel or Nitinol. The slotted tube making up the distal extension 88 includes a number of cylindrical rings 92 interconnected by longitudinal connectors 93, thereby defining a plurality of transverse slots 97 arranged in pairs along the length of the distal extension. Each pair of slots is disposed opposite one another on distal extension 88, thus defining a pair of opposing, longitudinal connectors 93. The longitudinal connectors 93 are flexible so as to be capable of bending around a transverse axis. Each pair of transverse slots 97 is oriented at 90 degrees relative to the adjacent pair of slots 97, so that the pairs of longitudinal connectors 93 alternate between those oriented vertically and those oriented horizontally. This allows distal extension 88 to bend about either a horizontal and vertical transverse axes, thus providing a high degree of flexibility. Of course, the pairs of transverse slots 97 could be oriented at various angles relative to adjacent pairs to provide flexibility about more than two axes. The slots provided in the slotted tube allows the distal extension 88 to be more axially flexible than it would be without the slots, while still retaining high column strength. It is preferable to provide transverse slots 97 and cylindrical rings 92 that each have a width that is approximately the same as the length of a stent segment 32. In addition or alternatively, the transverse slots 97 and cylindrical rings 92 may be spaced apart by a known fraction or multiple of the stent segment length. In this way, a detent mechanism may be provided on the interior surface of the sheath 25, with one or more detents that releasably engage the cylindrical rings 92 formed in the distal extension 88 to provide a tactile feedback based upon the distance that the outer sheath 25 is retracted relative to pusher tube 86.

A nesting tip 94 is formed on the distal end of the distal extension 88. The nesting tip preferably includes a plurality of fingers shaped and oriented to engage and interleave with the proximal end of the most proximal stent segment 32. The stent segments 32 preferably have axial extensions or projections on each end which interleave with those on the adjacent stent segment. The tip 94 of pusher tube 86 preferably has a geometry with axial projections similar to or complementary to those of the stent segments 32 so as to interleave therewith.

Preferably, the proximal portion 90 of the pusher tube has a diameter that is smaller than the diameter of the distal extension 88. Thus, the stainless steel hypotube material making up the proximal portion 90 of the pusher tube and part of the ribbon portion 89 may have a first diameter, while the slotted tube making up the distal extension 88 and the distal portion of the ribbon 89 may have a second, larger diameter. As noted above, the slotted tube and the hypotube are preferably joined by a weld 91 formed in the ribbon portion 89.

As best shown in FIGS. 2A-B, the pusher tube 86 extends longitudinally within the outer sheath 25 and over the inner shaft 27 through most of the length of the catheter body 22. The distal extension 88 is slidable over the tubular leg 72 and engages the stent segment 32 at the proximal end of the line of stent segments 32. At its proximal end (not shown), the pusher tube 86 is coupled to an actuator associated with the handle 38 (see FIG. 1). In this way, the pusher tube 86 can be advanced distally relative to the inner shaft 27 to urge the stent segments 32 distally over the expandable member 24 (or, alternatively, the pusher tube 86 may be held in position while retracting the expandable member 24 relative to stent segments 32) until the stent segments engage the stop 78. In addition, the pusher tube 86 can be used to hold the stent segments 32 in place on the expandable member 24 while the sheath 25 is retracted to expose a desired number of stent segments 32, as shown in FIG. 2B. As noted above, the proximal portion 90, ribbon portion 89, and distal extension 88 of the pusher tube are preferably constructed of stainless steel, but they may alternatively be constructed of a variety of biocompatible polymers, metals, polymer/metal composites, alloys, or the like.

It can be seen that with the sheath 25 retracted a desired distance, the expandable member 24 is allowed to expand when inflation fluid is delivered through the inflation lumen 66, thereby expanding a desired number of stent segments 32 exposed distally of sheath 25. The remaining portion of the expandable member 24 and the remaining stent segments 32 within sheath 25 are constrained from expansion by the sheath 25.

FIG. 2B further illustrates that when the sheath 25 is retracted relative to the expandable member 24, the guidewire tube exit port 35 becomes further away from the point at which the guidewire 36 exits the proximal end 74 of the tubular leg 72, increasing the distance that the guidewire 36 must pass within the interior of the sheath 25. Advantageously, the guidewire tube 34 provides a smooth and continuous passage from the tubular leg 72 through the guidewire tube exit port 35, eliminating any problems that might result from changing the alignment of the two. This is particularly important in the present device where the stent delivery catheter may carry a large number of stent segments 32 and the sheath 25 may be retracted a substantial distance relative to the expandable member 24, resulting in substantial misalignment of the guidewire tube exit port 35 relative to the tubular leg 72.

Referring now to FIGS. 5A-5E, the use of the stent delivery catheter of the invention will be described. While the device will be described in the context of coronary artery treatment, it should be understood that the device is useful in any of a variety of blood vessels and other body lumens in which stents are deployed, including the carotid, femoral, iliac and other arteries, as well as veins and other fluid-carrying vessels. A guiding catheter (not shown) is first inserted into a peripheral artery such as the femoral and advanced to the ostium of the target coronary artery. A guidewire GW is then inserted through the guiding catheter into the coronary artery A where lesion L is to be treated. The proximal end of guidewire GW is then inserted through the nosecone 28 and the guidewire tube 34 outside the patient's body and the stent delivery catheter 20 is slidably advanced over the guidewire GW and through the guiding catheter into the coronary artery A. The slider assembly 50 is positioned within the hemostasis valve at the proximal end of the guiding catheter, which is then tightened to provide a hemostatic seal with the exterior of the slider body 52. The stent delivery catheter 20 is positioned through a lesion L to be treated such that the nosecone 28 is distal to the lesion L. During this positioning, the sheath 25 is positioned distally up to the nosecone 28 so as to surround the expandable member 24 and all of the stent segments 32 thereon.

Optionally, the lesion L may be pre-dilated prior to stent deployment. Pre-dilation may be performed prior to introduction of the stent delivery catheter 20 by inserting an angioplasty catheter over the guidewire GW and dilating the lesion L. Alternatively, the stent delivery catheter 20 may be used for pre-dilation by retracting the sheath 25 along with the stent segments 32 to expose an extremity of the expandable member 24 long enough to extend through the entire lesion. This may be done while the delivery catheter 20 is positioned proximally of the lesion L or with the expandable member 24 extending through the lesion L. Fluoroscopy enables the user to visualize the extent of the sheath retraction relative to the lesion L by observing the position of the marker 56 on the garage 55 contained at the distal end of the sheath 25 relative to markers that may be formed on or attached to the guidewire tube 34 beneath the expandable member 24. To allow the stent segments 32 to move proximally relative to the expandable member 24, force is released from the pusher tube 86 and the valve member 58 engages and draws the stent segments proximally with the sheath 25. The pusher tube 86 is retracted along with the outer sheath 25 by use of an actuator provided on the handle 38. With the appropriate length of the expandable member 24 exposed, the expandable member 24 is positioned within the lesion L and inflation fluid is introduced through the inflation lumen 66 to inflate the expandable member 24 distally of the sheath 25 and thereby dilate the lesion L. The expandable member 24 is then deflated and retracted within the sheath 25 while maintaining force on the pusher tube 86 so that the stent segments 32 are positioned up to the distal end of the expandable member 24, surrounded by the sheath 25.

Figure 5A:
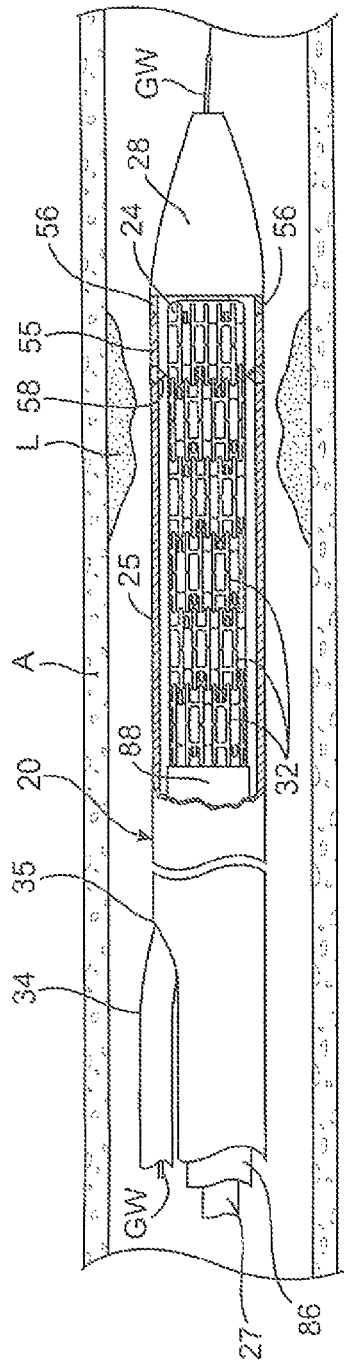

Following any predilatation, the stent delivery catheter 20 is repositioned in the artery A so that the nosecone 28 is distal to the lesion L as shown in FIG. 5A. The sheath 25 is then retracted as in FIG. 5B to expose the appropriate number of stent segments 32 to cover the lesion L. This step is referred to herein as the "paving" step. Again, fluoroscopy can be used to visualize the position of the sheath 25 by observing the marker 56 thereon relative to a marker 82 within the expandable member 24. As the sheath 25 is drawn proximally, force is maintained against the pusher tube 86 so that the stent segments 32 remain positioned up to the distal end of the expandable member 24. It should also be noted that the sheath 25 moves proximally relative to the guidewire tube 34, which slides through the guidewire tube exit port 35. Advantageously, regardless of the position of the sheath 25, the guidewire tube 34 provides a smooth and continuous passage for the guidewire GW so that the stent delivery catheter slides easily over the guidewire GW.

Figure 5B:
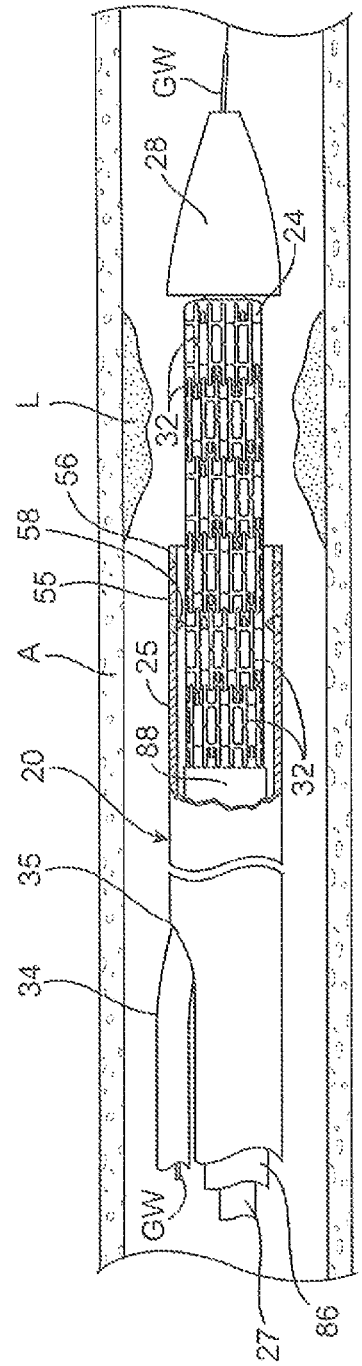
Figure 5C:
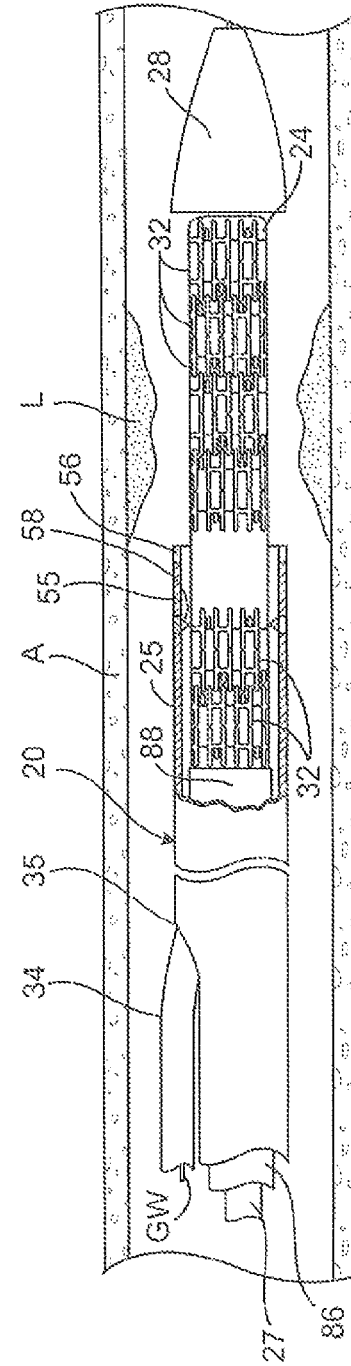

With the desired number of stent segments 32 exposed distally of the sheath 25, it is preferable to create some spacing between the stent segments to be deployed and those remaining enclosed within the sheath 25. This reduces the risk of dislodging or partially expanding the distal-most stent segment 32 within the sheath 25 when the expandable member 24 is inflated. Such spacing is created, as shown in FIG. 5C, by releasing force against the pusher tube 86 and retracting both the pusher tube 86 and the sheath 25 a short distance simultaneously. The engagement of the valve member 58 with the stent segments 32 moves those stent segments 32 within the sheath 25 away from those stent segments 32 distal to the sheath 25. This process is referred to herein as "separation." The distance of the spacing between the stents that are separated during the separation process is preferably about 1-2 mm, which distance refers to the distance between the distal end of the outer sheath 25 and the proximal end of the proximal-most exposed stent segment 32. By observing the radiopaque marker 56 on the sheath 25, the operator can adjust the spacing to be suitable in comparison to the length of the marker 56, which preferably has a length equal to the desired spacing distance.

The expandable member 24 is then inflated by delivering inflation fluid through the inflation lumen 66, as shown in FIG. 5D. The exposed distal portion of the expandable member 24 expands so as to expand the stent segments 32 thereon into engagement with the lesion L. If predilatation was not performed, the lesion L may be dilated during the deployment of the stent segments 32 by appropriate expansion of the expandable member 24. The sheath 25 constrains the expansion of the proximal portion of the expandable member 24 and those stent segments 32 within the sheath 25.

The expandable member 24 is then deflated, leaving the stent segments 32 in a plastically-deformed, expanded configuration within the lesion L, as shown in FIG. 5E. With the stent segments 32 deployed, the expandable member 24 may be retracted within the sheath 25, again maintaining force against the pusher tube 86 to slide the stent segments 32 toward the distal end of the expandable member 24. The expandable member 24 is moved proximally relative to the stent segments 32 until the distal-most stent segment engages the stop 78, (see FIGS. 2A-2B), thereby placing the stent segments 32 in position for deployment. This process is referred to herein as "resetting." After resetting, the stent delivery catheter 20 is then ready to be repositioned at a different lesion in the same or different artery, and additional stent segments may be deployed. During such repositioning, the guidewire tube 34 facilitates smooth tracking over the guidewire GW. Advantageously, multiple lesions of various lengths may be treated in this way without removing the stent delivery catheter 20 from the patient's body. Should there be a need to exchange the stent delivery catheter 20 with other catheters to be introduced over the guidewire GW, the guidewire tube 34 facilitates quick and easy exchanges.

As described herein, the valve member 58 is used prior to expansion of the expandable member 24 to create a gap or separation between adjacent stent segments 32 near the distal end of the outer sheath 25 of the delivery catheter during the separation process. The gap or separation is created between stent segments 32 that are to be deployed and those that are to remain in the catheter. During the paving step, the outer sheath 25 is retracted relative to the expandable member 24 to expose a selected number of stent segments 32 for deployment distally of the outer sheath 25. In the separation step, the valve member 58 exerts sufficient force against one or more stent segments 32 in the outer sheath 25 to allow the user to retract the segments with the outer sheath 25 proximally relative to the expandable member 24 to create a desired amount of "separation" or gap between the distal-most segment beneath the outer sheath 25 and the proximal-most segment exposed distally of the sheath 25.

Described below are several active valves or other mechanisms that are adapted to perform these functions in the delivery catheters described herein, or in other delivery catheters or other devices. By "active valve," it is generally meant that the valve or other mechanism is configured or adapted to be activated, actuated, or otherwise acted upon to selectively engage or disengage the stent segments 32. These active valves or other mechanisms thereby rely upon a change in the shape, position, orientation, size, configuration, dimension, or other property of at least a portion of the active valve to perform the function of engaging with the stent or stent segments. The above change may be performed either instead of, or in addition to, the friction-based mode of action by which the passive valve mechanisms described above function. It is contemplated that several of the active valves and active mechanisms may create separation between stent segments more effectively, more consistently, and/or while minimizing potential damage to the stent segments or to any drug or other coating thereon.

The active valves described herein may be actuated by inflation (e.g., causing a portion of the valve to be inflated by an inflation media), by mechanical operation, by application or withdrawal of energy (e.g., electricity, heat, cooling), by causing relative motion between components of the active valve structure, by direct operation of the active valve structure, or by other similar mechanisms described in reference to the embodiments below.

A. Active Valves

1. Inflatable Stent Valves

Turning to FIGS. 7A-B, 8, 9,10A-B, and 11A-B, there are shown several embodiments of inflatable stent valve members. The inflatable stent valves typically include one or more inflation members located at or near the distal end of the outer sheath 25. Each such inflation member preferably comprises an expandable balloon that is located in a position that allows it to remain out of contact with the stent segments until activated, and then to contact at least one of the stent segments upon activation. The expandable balloon is preferably formed of a material having properties allowing it to expand from a first, contracted state in which the inflation member does not contact the stent segments 32 located on the inner balloon member 70, and a second, expanded state in which the inflatable member is in contact with one or more stent segment(s) 32 located on the inner balloon member 70 beneath the outer sheath 25. The inflatable member is preferably a semi-compliant polymer such as Pebax, polyurethane, or Nylon. Non-compliant, fully elastic, or other materials such as PTFE may also be used. It is preferable that the portion of the inflatable member that contacts the stent segments 32 be formed of or have a coating of a material that produces a sufficient amount of friction when it engages the stent segments to restrain the stent segments during the separation process, but that also does not harm the stent segments or any drug or other coating thereon.

The inflatable valve preferably includes an inflation lumen that extends proximally from and that is in fluid communication with the inflatable valve. The inflation lumen may be formed integrally with the outer sheath 25, or it may be attached or otherwise affixed to the internal surface of the outer sheath 25. The inflation lumen preferably extends proximally to the handle 38 where it may be coupled to an inflation member that provides a source of inflation media for the inflatable valve. For example, an inflation port may be provided on the handle 38 in fluid communication with the inflation lumen. The inflation port may be connected to a source of inflation media, such as one of the commercially available balloon inflation devices described above. The inflation lumen preferably comprises a tube defining the sidewalls of a cylindrical, oval, or other-shaped lumen having an internal diameter (or comparable dimension) large enough to allow passage of a sufficient amount of inflation media to cause the inflatable member to expand an amount needed to perform the desired process.

The inflatable valve is activated by causing an amount of inflation media to be entered through the inflation lumen into the inflatable member to cause the inflatable member to transition from its contracted state to its expanded state. This may be done, for example, by activating a balloon inflation device (such as those sold by Guidant Corp. under the mark "Indeflator™") to cause the inflation media to be injected into the balloon. Preferably, a pressure regulator or other suitable monitor is provided to properly monitor the degree of inflation of the balloon. Once the inflatable valve is properly inflated, the delivery catheter is in condition to perform the separation process.

Figure 7A:
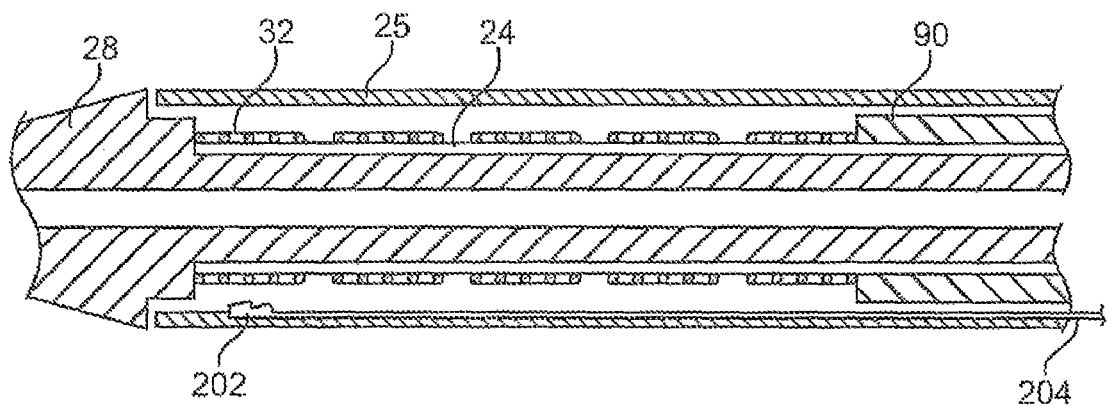
FIGS. 7A-B are cross-sectional views of a stent delivery catheter having an inflatable stent valve.
Figure 7B:
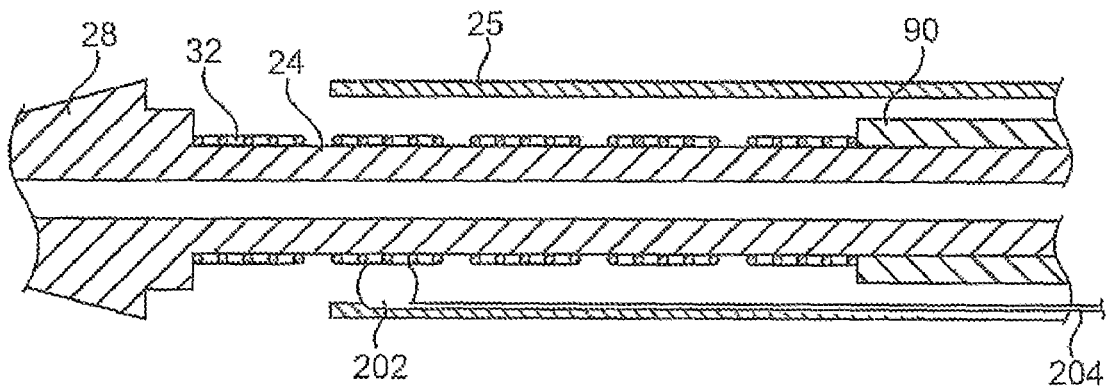

In a first embodiment, illustrated in FIGS. 7A-B, the inflatable member is a short balloon 202 that is formed integrally with and at the distal end of an inflation lumen 204. The balloon 202 essentially replaces the stent valve 58 described in the embodiments described above. The balloon 202 is located near the distal end of the outer sheath 25, and may be attached to or formed integrally with the inner surface thereof. The inflation lumen 204 is also preferably attached to or formed integrally with the inner surface of the outer sheath 25. In FIG. 7A, the balloon is shown in its contracted state, in which it does not contact the stent segment 32 located on the expandable member 24 radially inward of the balloon 202. In this position, the outer sheath 25 may be retracted proximally relative to the stent segments 32 to expose the distal-most stent segments 32 while maintaining the position of the pusher tube 90. This is the paving process described above in relation to FIG. 5A. Once the paving process is completed, the balloon 202 may be inflated, as shown in FIG. 7B. The balloon then engages the stent segment 32 located on the expandable member 24 just beneath the balloon 202. In this position, separation may be achieved by releasing the pusher tube 90, and retracting the outer sheath 25 proximally while the balloon 202 is engaged with the stent segment 32. Retraction of the outer sheath 25 should also cause retraction of the stent segment(s) 32 to which the balloon 202 is engaged, and all of those located proximally in the column of stent segments 32 beneath the outer sheath 25. Once adequate separation is obtained, the expandable member 24 is expanded in order to expand and deploy the exposed stent segments 32 in the manner described above in relation to FIGS. 5D-E.

The balloon 202 shown in the embodiment illustrated in FIGS. 7A-B may be of any of a variety of shapes and sizes. For example, the balloon 202 may be spherical, tube-shaped, or any suitable shape, provided that the shape is such that a sufficient amount of area is available to engage the stent segment(s) 32 in order to perform the separation process. Preferably, the balloon 202 is provided with a degree of contour or pre-shape to increase its available surface area. In addition, the engagement surface of the balloon 202 may be provided with surface contours, shapes, or other features that increase the amount of friction between the balloon 202 and the stent segment(s) 32, while minimizing any damage or other harm that may be caused to the stent segments 32 or their coatings, if any.

Figure 8:
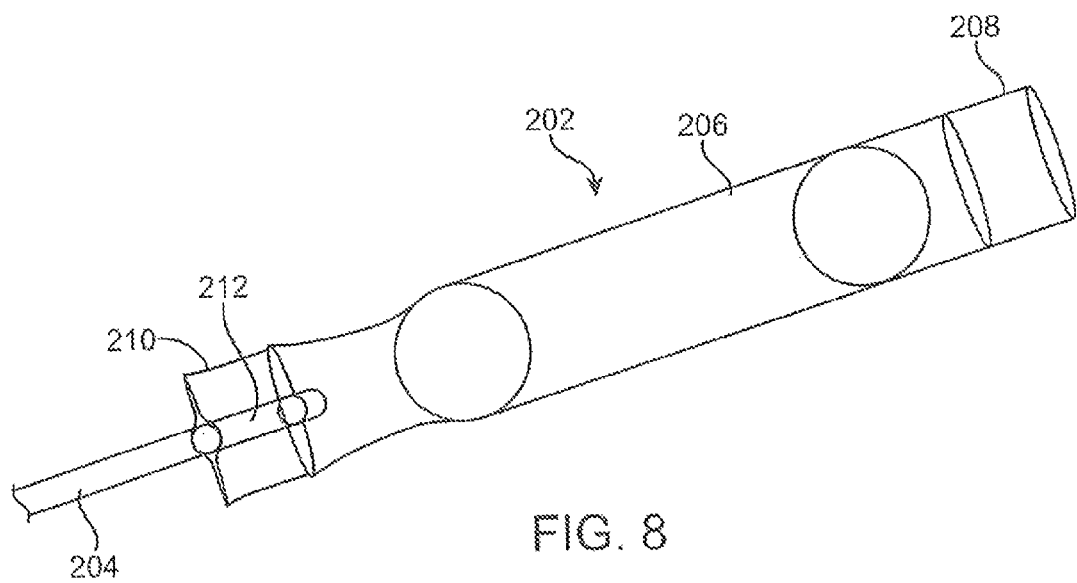
FIG. 8 is a perspective view of an inflatable stent valve.

In FIG. 8, one example of a balloon 202 is illustrated separately from the delivery catheter. The balloon 202 is shown in fluid communication with an inflation lumen 204 that extends proximally from the proximal end of the balloon 202. The balloon 202 includes an elongated tubular central portion 206, a distal sealed end 208, and a proximal sealed end 210. An entry lumen 212 is provided through the sealed proximal end 210 such that the inflation media carried by the inflation lumen 204 may be entered into the central portion 206 of the balloon when the balloon 202 is to be inflated.

The tubular central portion 206 of the balloon is the portion that physically engages the stent segment(s) 32. Accordingly, the size of the central portion 206 may be adjusted to provide the desired amount of contact area. For example, if the central portion 206 has a length that is greater than the length of a single stent segment 32, then the central portion 206 may engage two or more stent segments 32. This may be desired in order to distribute the friction force between the balloon and the stent segments more broadly. On the other hand, the contact force may be concentrated by providing a relatively shorter central portion 206. As noted above, additional surface features, shapes, or coatings may be incorporated as desired to change the friction characteristics of the balloon.

Figure 9:
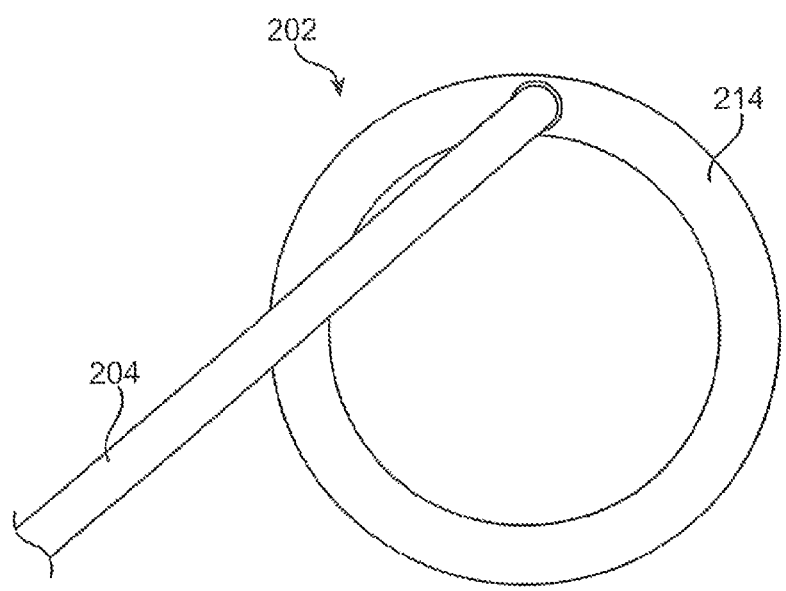
FIG. 9 is a perspective view of another inflatable stent valve.

Turning to FIG. 9, another example of a balloon 202 suitable for use as an active valve is illustrated separately from the delivery catheter. The balloon 202 includes a looped balloon 214 taking the form of a toroid. An inflation lumen 204 is in fluid communication with the looped balloon 214 and extend proximally therefrom. The looped balloon 214 is adapted to be placed within or formed integrally into the interior of the distal end of the outer sheath 25 of a delivery catheter in the location generally shown in FIGS. 7A-B, but the looped balloon 214 extends circumferentially around the internal surface of the outer sheath 25. The looped balloon thereby provides a contact area with the stent segment(s) 32 over the entire circumference of the stent segment(s) 32, when the balloon is in its expanded state. Although the looped balloon illustrated in FIG. 9—which is shown in its expanded state—shows a balloon having a generally circular cross-section, other shapes are also possible and may be desired in certain applications. For example, in alternative embodiments the cross-sectional shape of the looped balloon may be oval, or it may be generally triangular having an apex directed radially inward, or it may be generally triangular having an apex directed radially outward, or it may comprise another geometric or irregular shape. As noted above, additional surface features, shapes, or coatings may be incorporated as desired to change the friction characteristics of the balloon.

In alternative embodiments not shown in the drawings, the looped balloon 214 extends only partially around the circumference of the stent segment(s) 32. For example, the looped balloon 214 may extend over a range of approximately 45°, 90°, 180°, or any suitable range around the internal circumference of the outer sheath 25. In addition, the looped balloon 214 may be provided having a relatively flattened, elongated shape along the longitudinal axis of the delivery catheter, while still extending around all or a portion of the internal circumference of the outer sheath 25. Any or all of the foregoing variations may be suitable for a given application.

Figure 10A:
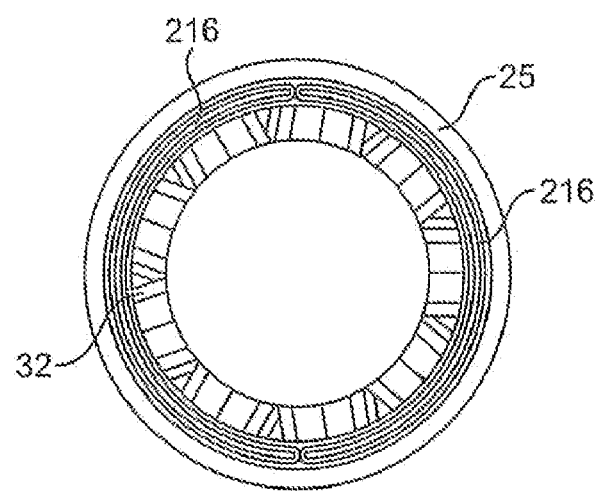
FIGS. 10A-B are a cross-sectional end view and exploded perspective view, respectively, of another inflatable stent valve.
Figure 10B:
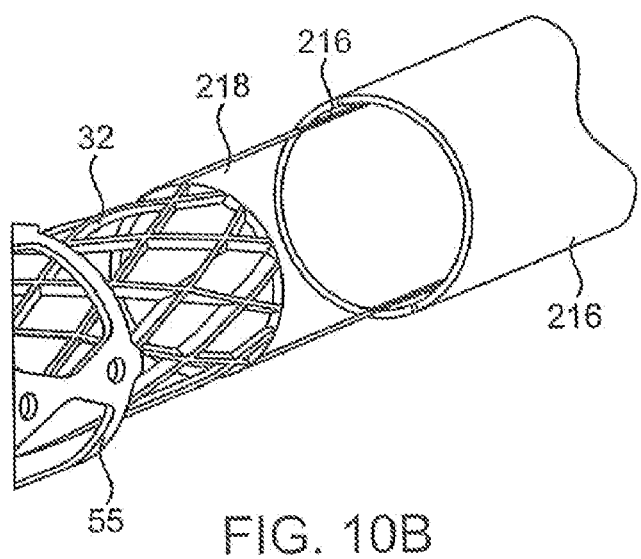

Turning next to FIGS. 10A-B, another embodiment of an inflatable valve is illustrated. The valve includes pair of thin-walled balloons 216 that are flattened and located between the stent segment(s) 32 and the outer sheath 25. The balloons 216 are each connected to inflation lumens 204 that are in fluid communication with a source of inflation media associated with the handle 38. The thin-walled balloons 216 preferably have lengths that are approximately the same as each other and the same as the combined lengths of the stent segments 32 carried by the catheter. Thus, when they are inflated, the balloons 216 will contact all of the stents in the column of stents provided on the catheter.

A tubular spacer member 218 having a slightly larger radial profile than each of the stent segments 32 is located on the proximal end of the proximal-most stent segment 32 in the column of stent segments 32. The spacer member 218 is preferably formed of a generally rigid material to provide sufficient radial and axial strength suitable to provide its needed functions. The spacer member 218 generally provides at least two functions. First, it provides a nominal holding force to the stents during the paving process. Second, it serves as a sliding element that the expansion balloon 24 rides on once it has been retracted proximally to the actual stent segments 32. This prevents the expansion balloon 24 from interfering with the thin-walled balloons 216, and vice versa.

During use, the thin-walled balloons 216 are inflated during both of the separation and the resetting processes. During paving and reset, the balloons 216 engage and retain all of the stent segments 32 and the tubular spacer member 218, thereby preventing stent segments 32 from running over one another as might occur if the stent segments 32 are held individually and pushed or pulled from one end.

Figure 11A:
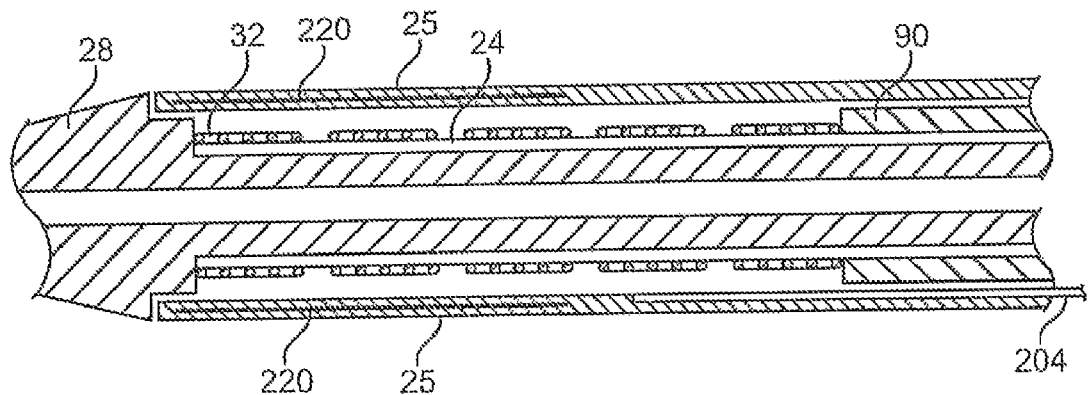
FIGS. 11A-B are cross-sectional views of a stent delivery catheter having another inflatable stent valve.
Figure 11B:
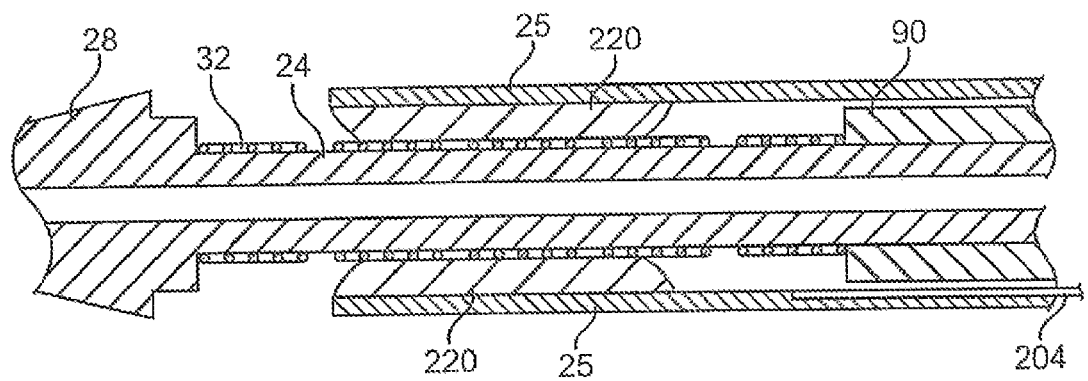

Turning next to FIGS. 11A-B, yet another embodiment of the inflatable valve member is illustrated. In the illustrated embodiment, the distal region of the outer sheath 25 includes an inflatable bladder 220 formed integrally therewith. The inflatable bladder 220 is in fluid communication with one or more inflation lumens 204 that are also formed integrally with, or attached to, the outer sheath 25. In its uninflated state, shown in FIG. 11A, the bladder 220 lies flat within the outer sheath 25, and there is no engagement with the underlying stent segments 32. Once inflated, as shown in FIG. 11B, the bladder 220 extends the outer sheath radially inward until it engages one or more of the stent segments 32 located radially inward of the outer sheath 25.

In certain of the embodiments illustrated in FIGS. 11A-B, the inflatable bladder 220 is located between laminated layers of polymeric or other materials that make up the outer sheath 25. In such embodiments, the outer sheath 25 may be constructed to delaminate as the bladder 220 is inflated, thereby providing the bladder 220 with the ability to engage with the underlying stent segment(s) 32. The delaminated layers forming the outer sheath 25 are then rejoined as the bladder 220 is deflated, thereby reforming the wall of the outer sheath 25. In other embodiments, the flatable bladder 220 is formed on the internal surface of the outer sheath 25, and therefore it does not cause delamination of the sheath as it expands to engage the underlying stent segments.

2. Mechanically Operated Stent Valves

A number of embodiments of mechanically operated stent valves are illustrated in FIGS. 12A-C, 13, 14A-B, 15, 16A-B, 17A-B, 18, and 19A-G. The mechanically operated stent valves typically include a mechanism for translating a pushing, pulling, or other force applied to an actuator member at the proximal end of the delivery catheter into a force applied by a valve member to one or more of the stent segments carried near the distal end of the catheter. The actuator is typically attached to or mounted on the handle 38, or it may pass through the handle 38. A switch, a grip, knob, or other actuator member may be provided on the handle 38 or otherwise associated with the actuator to provide the user with the ability to apply the actuation force. The actuator member is preferably mechanically coupled to the valve member in order to translate the actuation force into a force applied by the valve member to the stent segment(s), thereby facilitating the stent separation process.

Figure 12A:
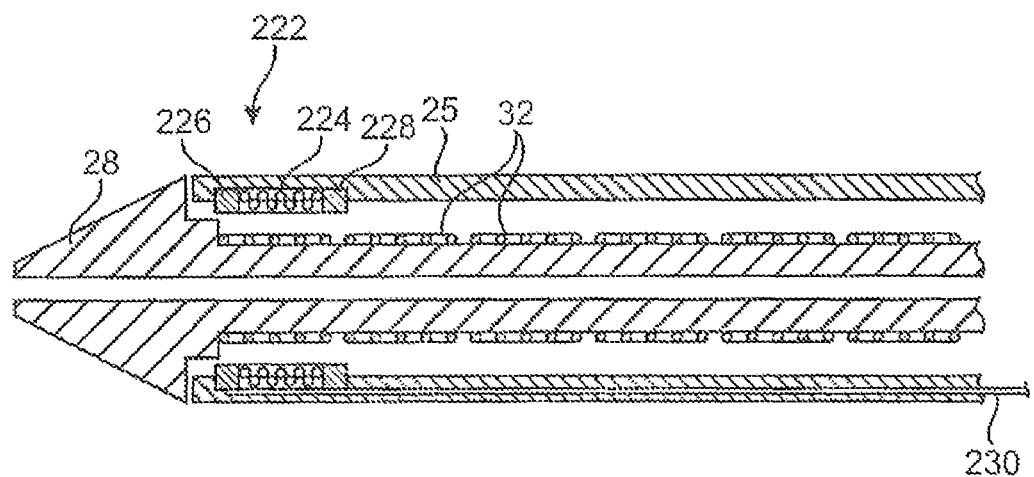
FIGS. 12A-C are cross-sectional views of a stent delivery catheter having a mechanical stent valve.
Figure 12B:
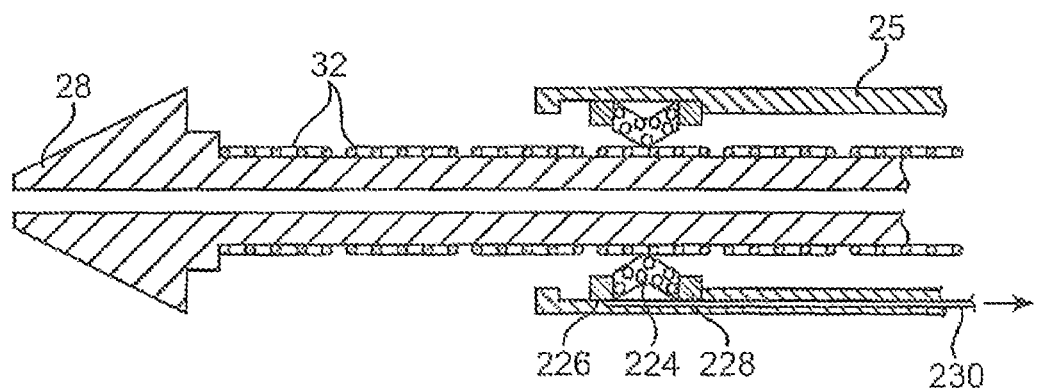
Figure 12C:
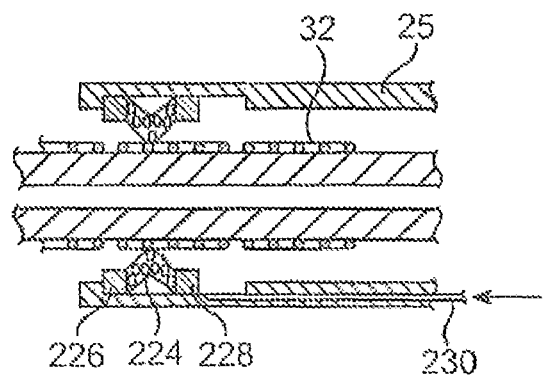

In a first embodiment, illustrated in FIGS. 12A-C, a delivery catheter includes a mechanical stent valve 222 having a formed section 224 of braided nickel-titanium alloy (NiTi—

Nitinol) wires. The NiTi braided section 224 is located between and attached to each of a distal end portion 226 and a proximal end portion 228, and is attached to the internal surface of the outer sheath 25 near its distal end. One or both of the distal end portion 226 and proximal end portion 228 is axially moveable relative to the outer sheath 25, thereby allowing one of the end portions 226, 228 to be moved closer to the other. This movement causes the NiTi braided section 224 to flex radially inward, thereby engaging the stent segment(s) 32 located radially inward beneath the braided section 224. (See, e.g., FIG. 12B or 12C). When the end portions 226, 228 are then moved apart, the NiTi braided section 224 returns to its original, contracted state. (See FIG. 12A).

The mechanical stent valve 222 is actuated by an actuator wire 230 that is installed within or attached to the interior surface of the outer sheath 25. The proximal end of the actuator wire 230 is preferably attached to or otherwise associated with the handle 38, where it is provided with a switch, a grip, a knob, or other actuator member. Alternatively, the actuator wire 230 may pass through or around the handle 38 to be operated by the user completely independently of the handle 38. In some embodiments, such as the embodiment illustrated in FIG. 12B, the actuator wire 230 is retracted proximally to actuate the mechanical stent valve 222. In this embodiment, the distal end of the actuator wire 230 is connected to the distal end portion 226 of the stent valve. Accordingly, as the actuator wire 230 is retracted proximally, it causes the distal end portion 226 to move proximally, toward the proximal end portion 228. This movement thereby causes the NiTi braided section 224 to flex inwardly, engaging the stent segment(s) 32. In other embodiments, such as the embodiment illustrated in FIG. 12C, the actuator wire 230 is advanced distally to actuate the mechanical stent valve 222. In this embodiment, the distal end of the actuator wire 230 is connected to the proximal end portion 228 of the stent valve. Accordingly, as the actuator wire 230 is advanced distally, it causes the proximal end portion 228 to move distally, toward the distal end portion 226. This movement thereby causes the NiTi braided section 224 to flex inwardly, engaging the stent segment(s) 32.

The construction of the mechanical valve makes use of the superelastic properties of the NiTi alloy that allow the braided section 224 to repeatedly flex to an expanded state (as shown, for example, in FIGS. 12B and 12C), and then return fully to its original, contracted state (as shown in FIG. 12A). Other materials, including other superelastic materials, may be substituted for the braided NiTi wires, provided the material is able to obtain the expanded and contracted states described and illustrated herein.

Figure 13B:
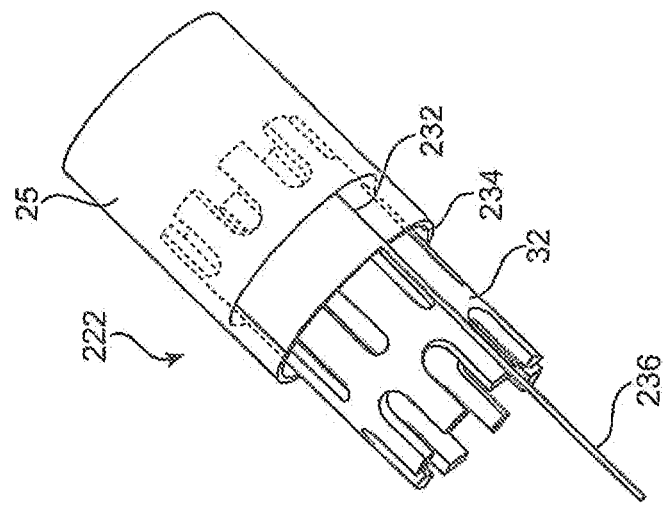
FIGS. 13A-B are perspective views of another mechanical stent valve.
Figure 13A:
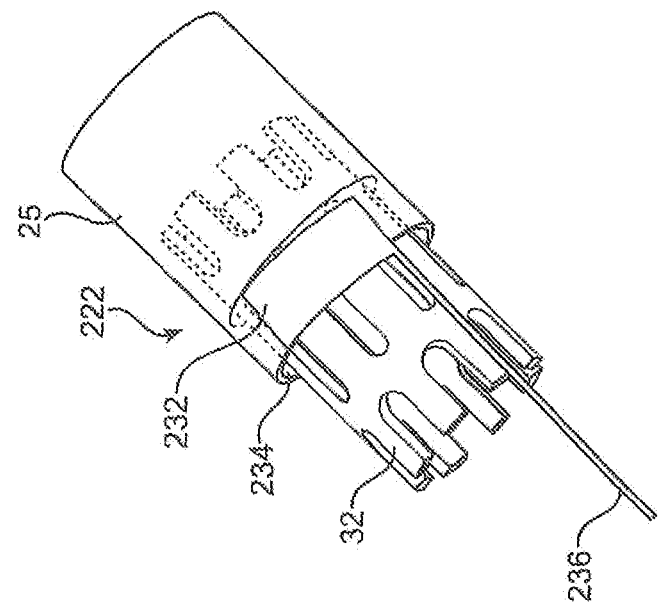

Another mechanical stent valve embodiment is illustrated in FIGS. 13A-B. The mechanical stent valve 222 includes a circumferential band 232 that is carried on the internal surface of and near the distal end of the outer sheath 25. The circumferential band 232 is a thin band of a resilient, elastic material, such as a highly elastic polymeric material, a metal or metal alloy (e.g., NiTi alloy), or other suitable material. The band 232 preferably extends completely around the internal diameter of the outer sheath 25; however, it may alternatively extend over only a portion of the internal diameter. The band 232 is a relatively thin sheet of material having a width (i.e., the dimension lying along the longitudinal axis of the catheter) that is sufficient to perform the stent valve function described below. Typically, the width of the band 232 is on the order of a fraction of the length of a typical stent segment 32, e.g., from about 5% to about 50% of the length of a stent segment.

While in its non-engaged state, as shown in FIG. 13B, the circumferential band 232 preferably rests within a circumferential slot 234 formed on the internal surface of the outer sheath 25. In this position, the circumferential band 232 does not interfere with the movement of the stent segments 32 beneath the outer sheath 25. A portion of the band 232 is preferably connected to or formed integrally with the outer sheath 25 such that the portion is not able to be easily moved relative to the outer sheath 25. Another portion of the circumferential band 232 is not attached to the outer sheath 25, and is therefore able to move relative to the outer sheath 25, at least as far as it is not constrained by the portion of the band 232 that is attached to the outer sheath 25.

An actuator wire 236 extends from the circumferential band proximally to the proximal end of the catheter. The actuator wire 236 is attached to the circumferential band 232 at a position that does not correspond to the portion of the band 232 that is attached to the outer sheath 25. As a result, when the actuator wire 236 is moved proximally or distally, it is able to cause the portion of the circumferential band 232 to which it is attached to move as well. Preferably, the proximal end of the actuator wire 236 is attached to or otherwise associated with the handle 38, although the actuator wire 236 may optionally be operated by the user independently of the handle 38. When the actuator wire 236 is retracted proximally, as shown in FIG. 13A, it causes the band 232 to slide out of the slot 234 and to impinge upon the stent segment(s) 32 located immediately beneath the circumferential band 232. This corresponds to the engaged state of the band 232, and facilitates the separation step of the stent delivery process.

Figure 14:
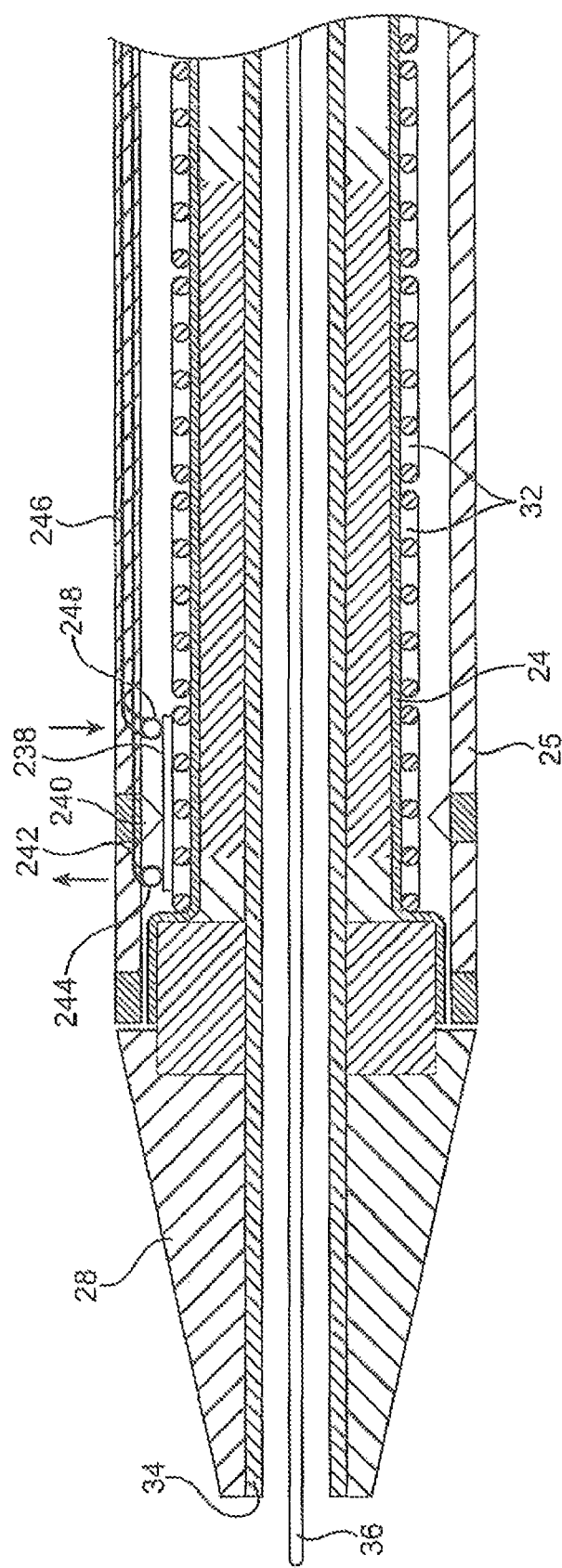
FIG. 14 is a cross-sectional view of a stent delivery catheter having another mechanical stent valve.

Still another mechanical stent valve embodiment is illustrated in FIG. 14. The mechanical stent valve 222 includes an elongated engagement member 238 that extends radially inward of and axially aligned with the outer sheath 25 near the distal end thereof. In the present embodiment, the engagement member is preferably formed of a relatively rigid material suitable for impinging upon and preventing motion of the underlying stent segment(s) 32 in the manner described below. The length of the engagement member 238 is typically on the same order as the length of a typical stent segment 32, although the engagement member may be either shorter or longer than a stent segment 32. The engagement member 238 rests against a fulcrum 240 that is attached to the internal surface of the outer sheath 25. The engagement member 238 is preferably located such that the fulcrum 240 rests against the engagement member 238 at its approximate longitudinal midpoint, similarly to the orientation of the fulcrum of a conventional children's "teeter totter." The fulcrum 240 is preferably formed of a relatively rigid material, such as a metal or hard polymeric material.

A distal actuator wire 242 and distal connector 244 are each attached to the engagement member 238 near its distal end. Similarly, a proximal actuator wire 246 and proximal connector 248 are each attached to the engagement member 238 near its proximal end. In the preferred embodiment, each of the distal and proximal connectors 244 and 248 includes a spring that is fixed to both the engagement member 238 and the internal surface of the outer sheath 25, thereby holding the engagement member in place in an orientation such that it is located between the outer sheath 25 and the underlying stent segment(s) 32 carried on the catheter shaft, but such that the engagement member 238 is not in direct contact with either the outer sheath 25 or the stent segment(s) 32. The force of each of the springs making up the distal and proximal connectors 244, 248 allows the engagement member 238 to rotate a short distance around the fulcrum 240 such that either the distal end or the proximal end of the engagement member 238 may come into contact with the underlying stent segment(s) 32. The rotation may be caused by proximal retraction or distal advancement of either of the distal actuator wire 242 or the proximal actuator wire 246. For example, proximal retraction of the distal actuator wire 242 causes the distal end of the engagement member 238 to move toward the outer sheath 25, while the proximal end of the engagement member 238 simultaneously moves toward and engages the underlying stent segment(s) 32.

In an alternative embodiment, also illustrated in FIG. 14, the engagement member 238 is actuated using resistance heating of components formed of shape memory materials. For example, in a preferred embodiment, the distal connector 244 and proximal connector 248 are formed of a shape memory material, such as NiTi alloy (e.g., Nitinol). In this embodiment, the connectors 244, 248 need not necessarily be springs, or spring-shaped; instead, the connectors 244, 248 are shaped such that they are able to contract and extend within the space between the outer sheath 25 and the engagement member 238. The connectors 244, 248 are programmed to expand and contract, respectively, when heat is applied to each of them. Accordingly, an electric current is passed through the distal actuator wire 242 and the proximal actuator wire 246 to cause heating of the distal connector 244 and proximal connector 248. The heating of these connectors causes the distal connector 244 to expand and the proximal connector 248 to contract, thereby causing the engagement member 238 to rotate slightly around the fulcrum 240 into engagement with the underlying stent segment(s) 32. This engagement of the underlying stent segment(s) 32 facilitates the separation process, as described above. When the current is removed from the actuator wires 242, 246, the connectors 244, 248 cool and the engagement member 238 is restored to its original position.

Figure 15:
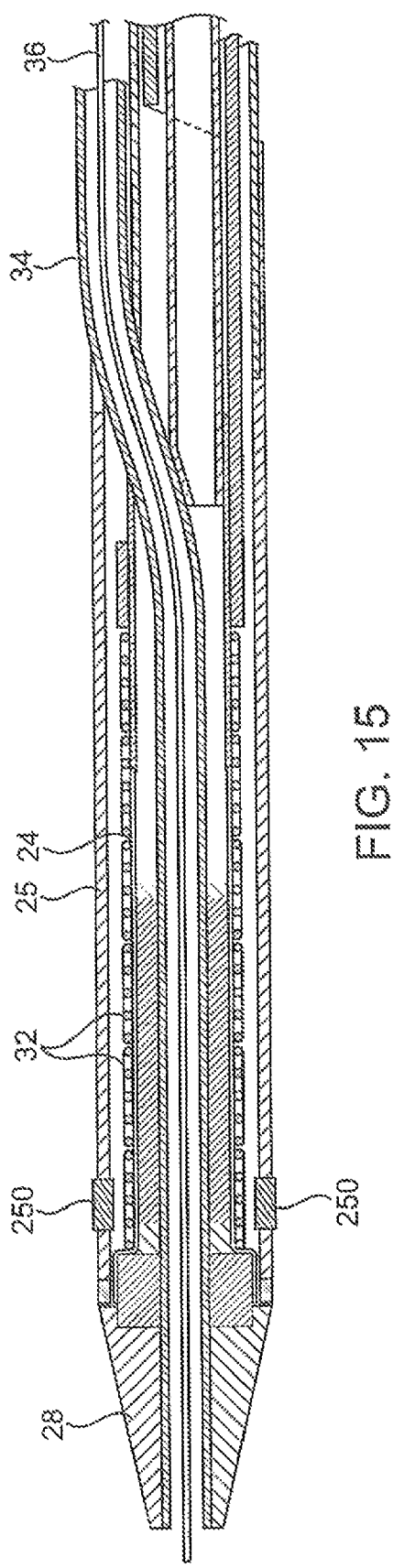
FIG. 15 is a cross-sectional view of a stent delivery catheter having another mechanical stent valve.

Turning next to FIG. 15, another mechanical stent valve embodiment includes a section of braided material 250 that is integrated with the outer shaft 25 near its distal end. The braided material 250 is preferably formed of braided wires or fibers of material making up the outer sheath 25. Alternatively, the braided material 250 comprises a braided section of fibers formed of a metal, metal alloy, or a polymeric material that is different from the outer sheath 25. The braided section 250 is constructed such that the section constricts radially inward when the outer sheath 25 is stretched longitudinally. The constriction thereby impinges on the stent segment(s) 32 carried on the inner shaft of the catheter, holding them in place in a sufficient manner to perform the separation process.

Any suitable sheath construction may be used to facilitate longitudinal stretching of the braided section 250 of the sheath. For example, in one embodiment, a pull-wire is attached to the distal portion of the outer sheath 25 located distally of the braided section 250. When the pull-wire is retracted along with the outer sheath 25, the braided section 250 does not stretch longitudinally. However, when only the outer sheath 25 is retracted, the retraction causes longitudinal stretching of the braided section 250, thereby providing the constriction function described above. In another embodiment, the outer sheath 25 is formed of a pair of telescoping shafts, i.e., an outer shaft and an inner shaft. The braided section 250 is connected at its proximal end to the distal end of the inner shaft, and at its distal end to the distal end of the outer shaft. Accordingly, as the outer shaft is extended distally relative to the inner shaft, it causes the braided section 250 to stretch longitudinally, thereby constricting upon the underlying stent segments 32. Other suitable mechanisms may also be used to facilitate the stretching function of the braided section 250, as will be appreciated by those of ordinary skill in the art.

Figure 16A:
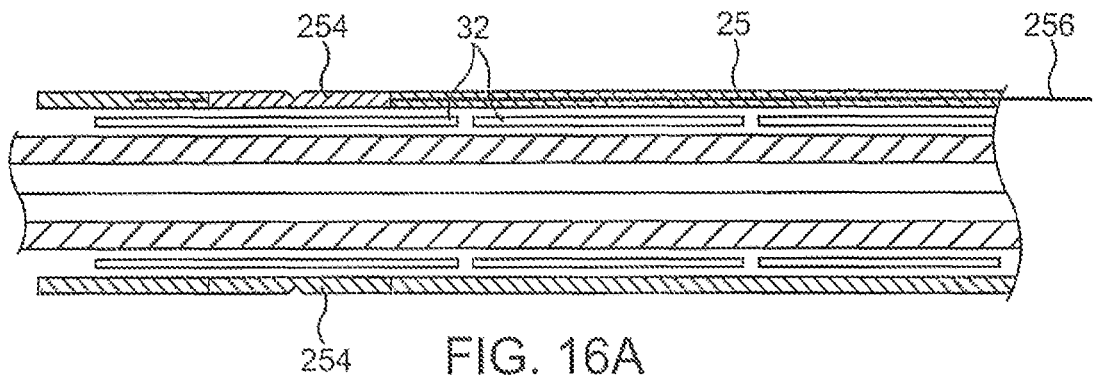
FIG. 16A-B are cross-sectional views of a stent delivery catheter having another mechanical stent valve.
Figure 16B:
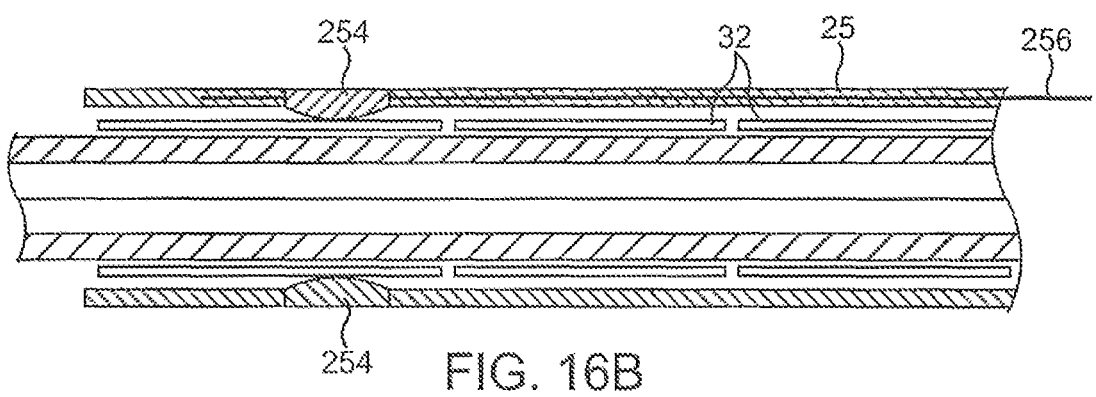

Another mechanical stent valve embodiment is illustrated in FIGS. 16A-B. The mechanical stent valve 222 includes an expansion section 254 formed in the outer sheath 25. The expansion section 254 is preferably formed of a material that is different from the remainder of the outer sheath 25. The expansion section 254 is preferably formed of a relatively soft, pliable, flexible material having a relatively low durometer. A pull wire 256 or other suitable actuator mechanism extends proximally from near the distal end of the outer sheath 25, from a point that is also distal of the expansion section 254. The pull wire 256 is of sufficient strength that the distal end of the outer sheath 25 may be retracted proximally against the column force of the expansion section 254, as described more fully below. The proximal end of the pull wire 256 is preferably attached to or associated with the handle 38, or it may be otherwise subject to manipulation by the user during operation of the catheter.

The soft, pliable expansion section 254 formed within the outer sheath 25 has a size and physical properties that allow the section to expand radially as a proximal force is applied to the distal end of the sheath 25 by the pull wire 256, as shown, for example, in FIG. 16B. Suitable materials that may be used to make up the expansion section include low durometer rubbers, thermoelastomers, and other materials having similar physical properties. As shown there, upon actuating the pull wire 256, the expansion section 254 expands radially until the expansion section engages the underlying stent segment(s) 32, thereby facilitating the separation process.

Figure 17A:
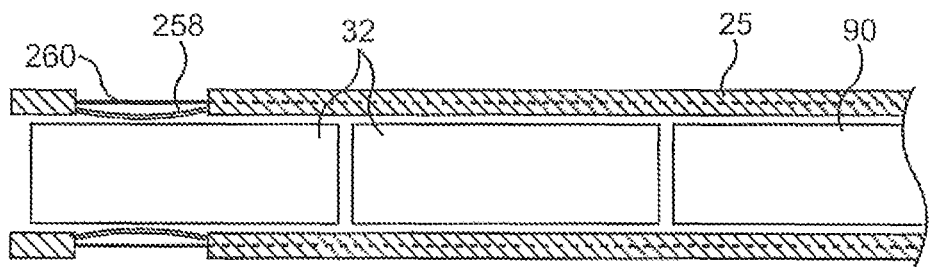
FIG. 17A-B are cross-sectional views of a stent delivery catheter having another mechanical stent valve.
Figure 17B:
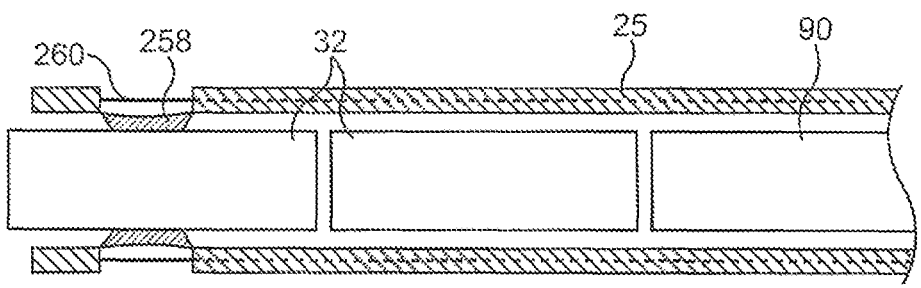

FIGS. 17A-B illustrate a mechanical stent valve embodiment similar to the embodiment illustrated in FIGS. 16A-B. In the FIG. 17A-B embodiment, a section of compliant material 258 is interposed between the distal-most section of the outer sheath 25 and the remainder of the outer sheath 25. The compliant material making up the compliant material section 258 may include a low durometer rubber, a thermoelastomer, or another material having similar physical properties A pull wire 260 is attached to the distal-most section of the outer sheath 25 and extends proximally from there to the handle 38 or to another actuator member located at or near the proximal end of the catheter. The pull wire 260 may extend through a lumen formed within the body of the outer sheath 25, as shown in FIGS. 17A-B, or it may extend along the external or internal surface of the outer sheath 25 to the proximal end of the catheter.

The compliant material section 258 has a shape and is placed at a location such that, when it is compressed axially, it will flex radially inward, as shown in FIG. 17B. The compliant section 258 is compressed axially by applying a proximally-directed force on the pull wire 260. The radially inward flexion allows the compliant section 258 to engage the stent segment(s) 32 located radially inward of the compliant section 258, thereby facilitating the separation process in the manner described above. Once stent separation is completed, the pull wire 260 is released, thereby allowing the compliant section 258 to return to its relaxed state in which it no longer actively engages any of the stent segments 32. (e.g., as shown in FIG. 17A).

Turning next to FIG. 18, another embodiment of a mechanically operated stent valve includes a thin-walled outer cylinder 262 that is preferably formed of a metal or other electrically conductive material. The outer cylinder has an outer diameter that is about equal to the inner diameter of the outer sheath near its distal end, and is adapted to be attached to the outer sheath at that location. An inner cylinder 264 is formed within and attached to the outer cylinder 262. The inner cylinder 264 is formed of an electroactive polymer artificial muscle (EPAM) material. EPAMs are materials that are physically transformable by application of small electrical potentials. When a voltage is applied across two thin film elastic electrodes separated by an elastic dielectric polymer, a Maxwell pressure is created by the electrode films on the polymer. The elastic polymer acts as an incompressible fluid, with the result that the electrode pressure causes the polymer film to become thinner (i.e., the z axis becomes smaller) as the film expands in the planar directions (i.e., the x and y axes). In this way, electric potential is converted to mechanical motion. The energy density and power density of EPAM is several times greater than that of comparable actuator technologies such as piezoelectric devices and electromagnetic devices such as motors and solenoids.

In the embodiment shown in FIG. 18, the inner cylinder 264 of EPAM material is housed within the outer cylinder 262. The inner cylinder 264 is attached to at least two electrodes 266 that extend proximally to the proximal end of the delivery catheter. The electrodes 266 may be embedded in the outer sheath 25, or they may be attached to the inner or outer surface of the outer sheath 25. The proximal ends of the electrodes 266 may be attached to or mounted on the handle 38, or otherwise accessible to the user outside of the delivery catheter. The proximal ends of the electrodes 266 are connected to a switchable source of a small electric current used to activate the EPAM at the distal end of the catheter.

The inner cylinder 264 of EPAM material includes a plurality of protruberances 268 formed on its inward-facing surface. The protruberances 268 have a sufficient shape and size to generate a changing electrical signal in the electrodes 266 as the stent segments 32 pass through the inner cylinder 264. The changing electrical signal is able to be monitored and read by a suitable ammeter, voltmeter, or other device associated with the electrodes 266. In this way, the stent valve may also be used to sense the movement of the stent segments through the distal end of the outer sheath 25 to provide additional information to the user, such as knowing the number of stent segments 32 that have been exposed during the paving process.

The stent valve is operated by providing a small current (e.g., less than 10 microamps) that causes the inner cylinder 264 to expand, allowing passage of the catheter inner shaft 27, expandable member 24, and stent segments 32 to readily pass through the inner cylinder 264. When the current is switched off, the inner cylinder 264 contracts, impinging upon the stent segment(s) 32 located radially within the inner cylinder 264, thereby holding the stent segments 32 in place within the outer sheath 25. This action facilitates the separation process as the stent segment(s) 32 located distally of the inner cylinder 264 may then be advanced out of the distal end of the outer sheath 25 (or, stated otherwise, the outer sheath 25 may be retracted to expose the stent segment(s) 32 located distally of the inner cylinder 264). Once thus exposed from within the outer sheath 25, the exposed stent segment(s) 32 are subject to expansion and deployment in the manner described above.

Turning next to FIGS. 19A-G, another embodiment of a mechanical stent valve is illustrated in a generally schematic form. The valve has a design and is constructed in a very similar manner to the valve illustrated in FIGS. 17A-B and described above. In particular, the mechanical stent valve includes a compliant material section 258 contained between the distal end of the outer sheath 25 and the remainder of the outer sheath 25. A pull wire 260 is attached to the distal portion of the outer sheath 25, and extends proximally to the proximal end of the delivery catheter, as described above. The compliant material section 258 is compressed by actuation of the pull wire 260, (see, e.g., FIG. 19C), thereby causing the compliant material section 258 to flex radially inward to impinge upon the underlying stent segment(s) 32, just as described above in relation to FIGS. 17A-B.

In the FIG. 19A-G embodiment, the mechanical stent valve is also provided with a passive valve member 58 attached to the distal end portion of the outer sheath 25, distally of the compliant material section 258. The passive valve 58 is constructed of the same materials and is oriented just as the passive valves 58 described above in relation to the embodiments illustrated in FIGS. 2A-B and 5A-E. Accordingly, the passive valve 58 is in constant engagement with the underlying stent segments 32, although the friction force between the passive valve 58 and the stent segments 32 is sufficiently small that it may be overcome by the operation of the other components of the catheter, as described below.

The mechanical stent valve illustrated in FIGS. 19A-G operates in a manner that allows it also to function as a stent segment metering device. For example, the distance that the compliant material section 258 compresses when the actuator wire 260 is pulled proximally is preferably a repeatable and known amount. This also means that the distance that the distal portion of the outer sheath 25 moves proximally relative to the remainder of the outer sheath when the actuator wire 260 is pulled proximally is a repeatable and known amount. Accordingly, by following the procedure described below, and illustrated in FIGS. 19B-G, the mechanical stent valve is able to be retracted in a series of steps, during which the distance traveled by the mechanical stent valve is known, and the number of stent segments 32 may be counted. After retraction, the stent valve is configured to provide a restraining force on the underlying stent segment(s) in order to facilitate the separation process.

Figure 19A:
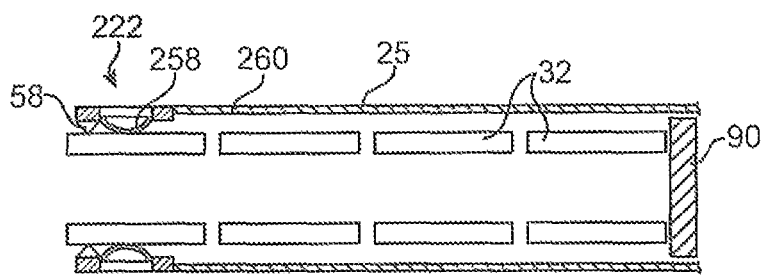
FIGS. 19A-G are schematic views of a stent delivery catheter having another mechanical stent valve.
Figure 19B:
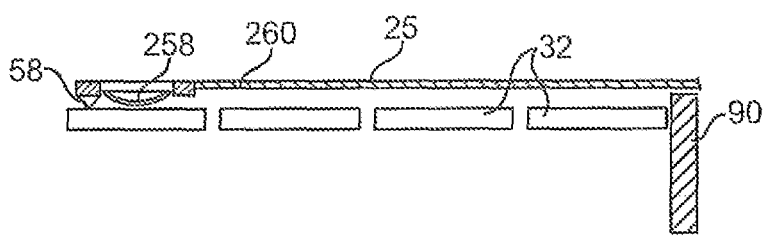
Figure 19C:
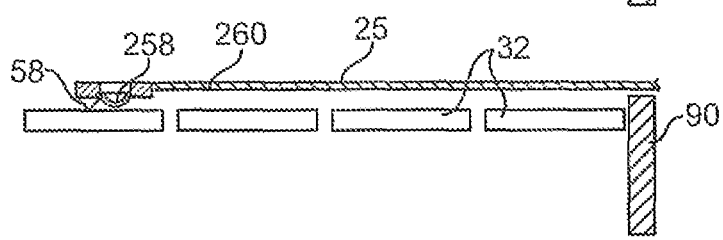

Turning first to FIG. 19B, the mechanical stent valve 222 is shown in its extended state, i.e., the compliant material section 258 is not compressed. (The reader will note that FIGS. 19B-G illustrate schematic views of only the upper half of the distal end of the delivery catheter.) The passive valve 58 is in contact with the underlying stent segment 32. The compliant material section 258 is then fully compressed by applying a proximally-directed force on the pull wire 260, as shown in FIG. 19C. A backing force is maintained by the pusher tube 90 during this step, thereby maintaining the position of the column of stent segments 32 carried by the inner shaft of the catheter, and allowing the passive valve 58 to slide proximally against the underlying stent segment(s) 32. The distal portion of the outer sheath travels a known distance proximally during this step. For example, the known distance may be one-half of the length of a stent segment, as illustrated in FIG. 19C. Other distances are possible by providing a compliant material section 258 having a selected length.

Figure 19D:
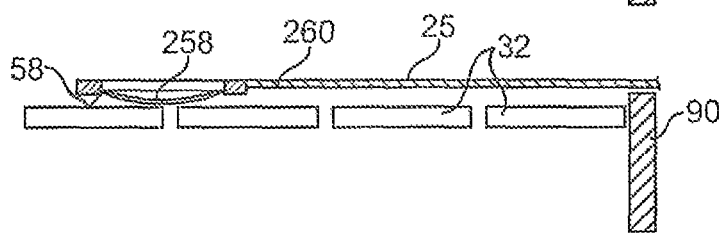
Figure 19E:
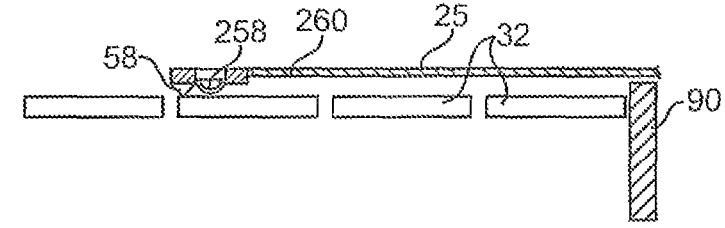
Figure 19F:
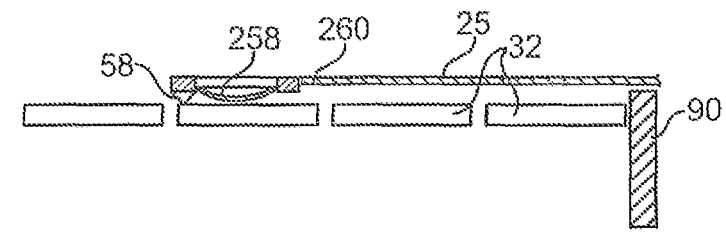

After the compliant material section 258 has been compressed, the proximal portion of the outer sheath 25 is retracted while maintaining the position of the distal portion, thereby allowing the compliant material section 258 to re-extend. This is illustrated in FIG. 19D. The retraction and extension processes are then repeated, as shown in FIGS. 19E-F, until the desired number of stent segment(s) 32 are exposed from under the outer sheath 25 (i.e., "paved out"). The number of stent segment(s) 32 paved out will be known based upon the number of times the compliant material section 258 is compressed and extended, and the known distance covered by each such process. Although only one segment 32 is shown having been paved out in the Figures, those of skill in the art will recognize that any number of the available stent segment(s) may be paved out.

Figure 19G:
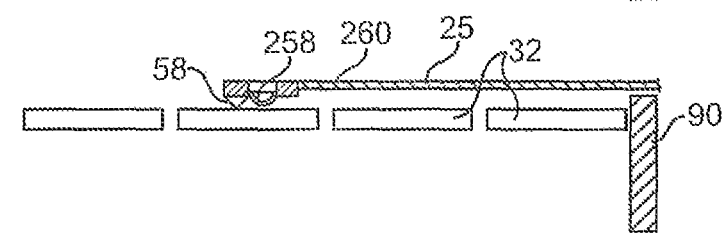

After the paving process is completed, the distal portion of the outer sheath 25 is retracted in order to compress the compliant material section 258 and cause it to flex inwardly to engage the distal-most stent segment 32 underlying the outer sheath 25, as shown in FIG. 19G. After engaging the stent segment 32, distally oriented force on the pusher tube 90 is released, and the outer sheath 25 is retracted to perform the separation process. The delivery catheter is then in condition to deploy the exposed stent segment(s) 32.

3. Energy Operated Stent Valves

A number of embodiments of stent valves actuated by application of one or more forms of energy are illustrated in FIGS. 20 through 35. The energy operated stent valves typically include a mechanism for translating an applied energy into a force applied by a valve member to one or more of the stent segments carried near the distal end of the catheter. The applied energy may be electrical, heat, or other energy having the ability to cause an active stent valve member to actuate. Accordingly, an energy source is typically associated with the delivery catheter, such as being mounted or attached to the handle 38, or adapted to pass through the handle 38. (See FIG. 1). Typical energy sources include battery or electric. A switch, a grip, knob, or other actuator member 205 may be provided on the handle 38 or otherwise associated with the source of actuator energy to provide the user with the ability to apply the actuation force. The energy source is preferably operatively coupled to the valve member in order to translate the energy into a force applied by the valve member to the stent segment(s), thereby facilitating the stent separation process.

A schematic representation of an energy actuated stent valve 380 is shown in FIG. 35. The stent valve 380 is located near the distal end of the outer sheath 25, and is attached to the inner surface thereof. In alternative embodiments, the stent valve 380 may be embedded within the wall of the outer sheath 25. A conductor 382 is attached to the stent valve 380 and extends proximally to the proximal end of the catheter. The proximal end of the conductor 380 is preferably operatively connected to the actuator member 205 on the handle 38 (see FIG. 1). Alternatively, the conductor 382 is attached directly or indirectly to the source of activation energy. The conductor is preferably attached to the inner surface of the outer sheath 25, but may alternatively be embedded within the outer sheath 25.

Typically, the stent valve 380 is a generally cylindrical member that coaxially surrounds one or more underlying stent segment(s) 32. In its unactivated state, the stent valve 380 has an inner diameter that provides a clearance gap between the stent valve 380 and the underlying stent segments 32, thereby facilitating the paving and resetting steps described above in relation to FIGS. 5A-E. The stent valve 380 shown in FIG. 35 is in its unactivated state. In its activated state, the stent valve 380 has at least a portion having a relatively smaller inner diameter or other impingement upon the underlying stent segment(s) 32, thereby restricting movement of the stent segment(s) 32 relative to the stent valve 380 and, thereby, relative to the outer sheath 35. The stent valve 380 is thereby able to facilitate the separation process described above in relation to FIGS. 5B-C.

Several embodiments of energy actuated stent valves are described below in relation to FIGS. 20 through 34A-F. For clarity, several of the Figures provide illustrations of the stent valve member 380 (or its separate components) without showing the surrounding outer sheath 25 or other components of the delivery catheter. The illustrations and descriptions are intended to be read in conjunction with the above descriptions of the stent valve 380 illustrated in FIG. 35 and the catheter structure illustrated in FIG. 1.

Figure 20:
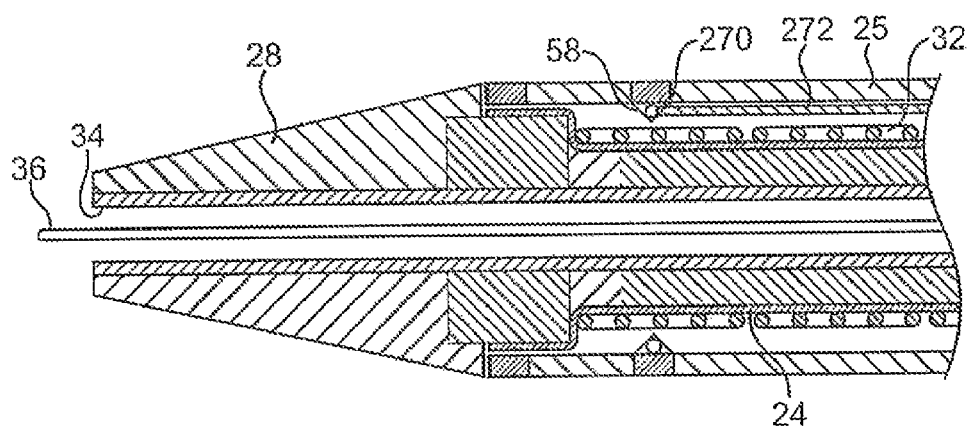
FIG. 20 is a cross-sectional view of a stent delivery catheter having an energy actuated stent valve.

In a first embodiment, illustrated in FIG. 20, a passive stent valve 58 is supplemented with a loop member 270 that is embedded within, attached to, or otherwise connected to the passive valve 58. The loop member 270 is preferably formed of a material that is responsive to an applied energy, such as heat, cooling, electricity, or other energy. The loop member 270 is formed of a material that has a shape memory or other property that allows it to change shape upon activation by an energy source. In particular, the loop member 270 is configured to contract radially inward upon actuation, thereby applying a valving force upon the underlying stent segments. The valving force is then used to perform the separation process described above and illustrated in FIGS. 5B-C.

A particular preferred material for the loop member 270 is NiTi alloy, i.e., Nitinol™. The NiTi alloy has a shape memory property such that it is able to be "trained" to change shape upon application of energy, such as heat or electrical. Other materials that may be used to construct the loop member 270 include shape memory polymers, blends of these materials, or other materials having similar properties known to those skilled in the art. In the preferred embodiment, the NiTi loop member 270 contracts radially upon application of heat or electricity applied through a conductor, such as a conductor wire 272. The conductor wire 272 may comprise any conductive metal or other material, such as copper wire, aluminum wire, or the like. Accordingly, when it is desired to provide a valve force against the stent segment(s) 32, energy is applied through the conductor to the NiTi loop member 270, thereby causing it to contract and apply a force against the underlying stent segment(s) 32.

The passive valve 58 is preferably formed of a relatively soft, compliant material in order to reduce or eliminate any damage to the stent segment(s) 32 or any coatings contained on the stent segment(s) 32. Preferably, the passive valve 58 also provides the function of restoring or helping to restore the loop member 270 to its resting state after the actuation energy is removed from the loop member 270. For example, the elastic properties of the passive valve 58 preferably create a restoring force biasing the loop member 270 to its large-diameter state, away from its engagement with the stent segment(s) 32. While the restoring force of the passive valve 58 is less than the contracting force of the loop member 270 during actuation, the restoring force 58 is sufficient to restore (or help restore) the shape of the loop member 270 when the actuation energy is removed.

Although application of heat, cooling, or electrical energy are described above as suitable actuation methods for the loop member 270 active stent valve, any other suitable actuation method may be employed. For example, a mechanical actuator may be used to actuate a suitable mechanical loop member 270 that contracts by being mechanically shortened, or other suitable method.

Figure 21A:
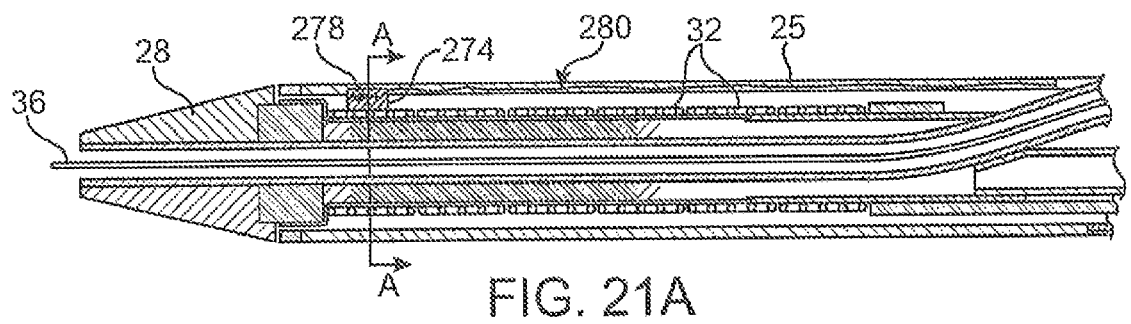
FIGS. 21A-C are cross-sectional views of a stent delivery catheter having another energy actuated stent valve.
Figure 21B:
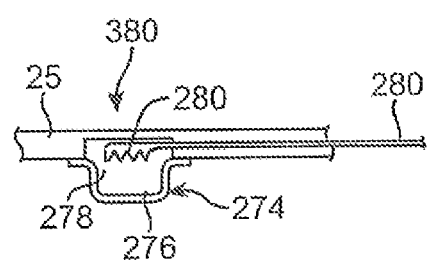
Figure 21C:
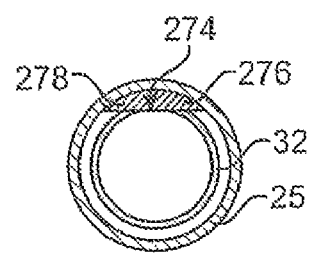

Another energy actuated active stent valve is illustrated in FIGS. 21A-C. The stent valve 380 includes a valving portion that operates in reliance upon a transformation of the phase of the material contained within the valving portion. The phase transformation of the material causes the valving portion to change its ability to engage the stent segment(s) 32 underlying the valve, from a first state in which the stent segment(s) 32 are prevented from moving relative to the active stent valve (to facilitate separation) to a second state in which the stent segment(s) 32 are allowed to move (to facilitate paving and resetting). For example, the embodiment illustrated in FIGS. 21A-C includes a membrane 274 attached to the inner surface of the outer sheath 25 near the distal end thereof. The membrane 274 defines a void space 276 between the membrane 274 and the inner surface of the outer sheath 25. The void space 276 defined by the membrane 274 may extend over a portion of the inner periphery of the outer sheath 25, or it may extend around the entire inner diameter of the outer sheath 25. In the preferred embodiment shown in FIGS. 21A-C, the void space 276 extends over only a portion of the inner diameter of the outer sheath 25, i.e., approximately 60° to about 90° of the inner diameter.

A transformation medium 278 is contained within the void space 276 formed by the membrane 274. The transformation medium 278 is a material that is able to transform from a first state having sufficient size and stiffness to effectively engage the underlying stent segment(s) 32 and restrain them from motion relative to the outer sheath 25 during the separation process as the outer sheath 25 is retracted proximally relative to the inner shaft, to a second state having a reduced size and/or stiffness that allows the stent segment(s) 32 to slide past the valve member 380 as the outer sheath 25 is retracted proximally or advanced distally relative to the inner shaft. A preferred transformation medium 278 is a wax having a melting point that is higher than the temperature encountered by the transformation medium 278 during use of the delivery catheter (e.g., the body temperature of a patient undergoing a medical treatment). Accordingly, the wax is in its solid form as the delivery catheter is inserted into the patient, and is able to be transformed to a liquid form by application of a relatively small amount of energy in the form of heat. For example, paraffin has a melting point of approximately 122° F., which is higher than the human body temperature. Other waxes and wax-like materials have similar melting points, thereby allowing phase transformation by exposure to a relatively small amount of heat (or other) energy.

A preferred actuation mechanism for heating the transformation medium 278 is an electrical resistance member, such as a resistance wire 280 that is exposed within the interior of the void space 276, in contact with the transformation medium 278. The remaining portion of the wire 280 is insulated and is embedded within or attached to the outer sheath 25 of the catheter. The proximal end of the resistance wire 280 is coupled to a battery or other source of electrical energy that is associated with the handle 38 or otherwise accessible to the user near the proximal end of the delivery catheter. When electrical energy is applied to the resistance member, the resistance member is heated, thereby causing the transformation medium to transform from its first state to its second state.

During operation, the transformation medium 278 remains in its solid stage during those processes—such as the separation process—that require the active valve to engage the stent segment(s) 32 and prevent motion of the stent segment(s) 32 relative to the outer sheath 25. During the other processes—such as paving and resetting—the transformation medium 278 is heated to cause it to melt, thereby causing the active valve to allow free passage of the stent segment(s) 32 relative to the outer sheath 25.

Figure 22A:
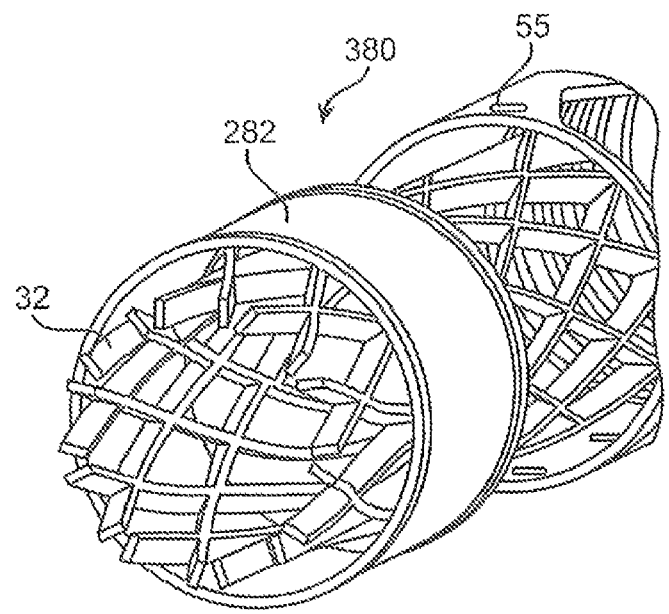
FIGS. 22A-B are perspective views of another energy actuated stent valve.
Figure 22B:
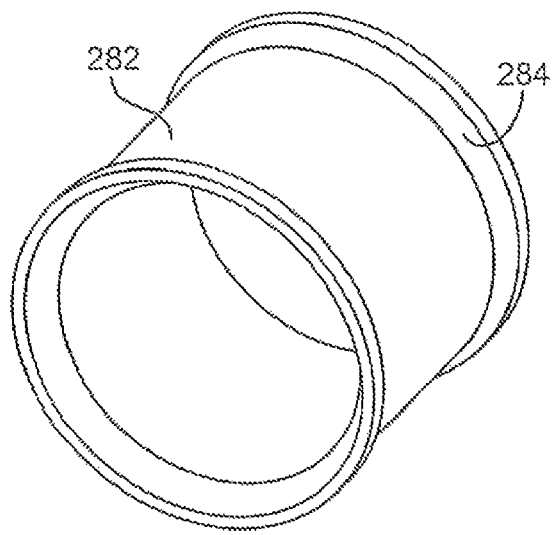

Another embodiment of an energy actuated active stent valve is shown in FIGS. 22A-B. The active stent valve 380 includes a deformable cylinder 282 having a first state in which its inner diameter is slightly larger than the outer diameter of the stent segment(s) 32, and a second state in which its inner diameter is smaller than the first diameter, and small enough to allow the deformable cylinder 282 to provide a valving force against the stent segment(s) 32 located within its interior during the separation process. The deformable cylinder 282 is preferably formed of a material having a physical property, such as shape memory, that allows the material to assume different shapes and sizes under the control of the application of an actuation energy. In the preferred embodiment, the deformable cylinder 282 is formed of NiTi alloy (i.e., Nitinol) having a shape memory imparted that allows the cylinder 282 to deform between the first state and second state identified above.

The cylinder 282 is preferably shape set straight and centerless ground to the desired shape and size to be attached to the inner surface of the outer sheath 25 of the catheter near the distal end of the outer sheath 25. The cylinder 282 is expanded manually prior to assembly into the catheter, and shape set such that application of heat from a source external of the catheter shaft causes recovery back to the smaller shape memory size when required to provide interference with the stent segment(s) 32 during the separation process. One or more electrodes are operatively attached to the cylinder 282 and extend proximally either embedded within or attached to the outer sheath 25, the proximal end(s) of the electrode(s) being coupled to a source of activation energy, such as a battery or other source of electrical or heat energy. The battery may be installed within the handle 38, attached to the handle 38, or otherwise associated with the proximal end of the catheter.

In the embodiment shown in FIG. 22B, the cylinder 282 has a lead in section 284 formed on the front and back ends of the cylinder 282. The lead in sections 284 are generally in the shape of a small tapered end, thereby allowing the cylinder 282 to more easily pass over stent segments 32 without catching or snagging on any protruding struts or other portions of the stent segments 32. The tapers formed by the lead in sections 284 also provide a capture area on the outer surface of the cylinder 282 in which to locate windings of heating wire if such windings are applied to heat the cylinder 282.

Additional features may optionally be incorporated on the cylinder 282, including longitudinal struts or other members that provide structural strength or that provide improved engagement between the cylinder 282 and the underlying stent segment(s) 32 during the separation process. For example, an additional layer of softer, elastomeric material may be provided on the internal surface of the cylinder 282 to adjust the frictional forces between the cylinder and the stent segments 32, and to protect the stent segments 32 and any coatings thereon from being damaged or removed.

Figure 23A:
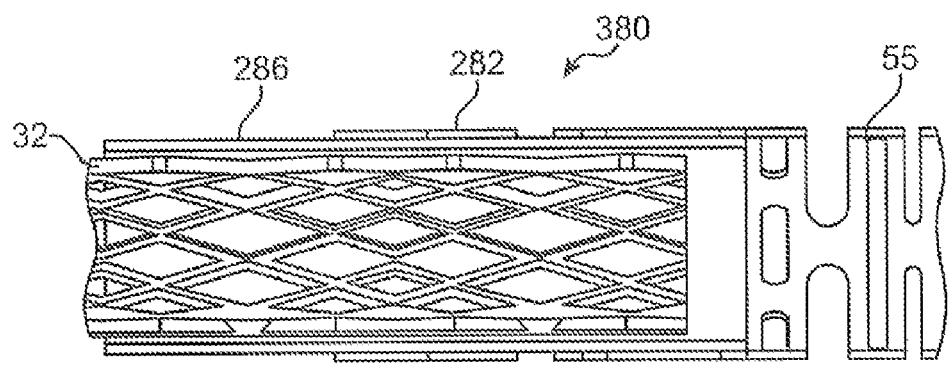
FIGS. 23A-B are cross-sectional and perspective views, respectively, of another energy actuated stent valve.
Figure 23B:
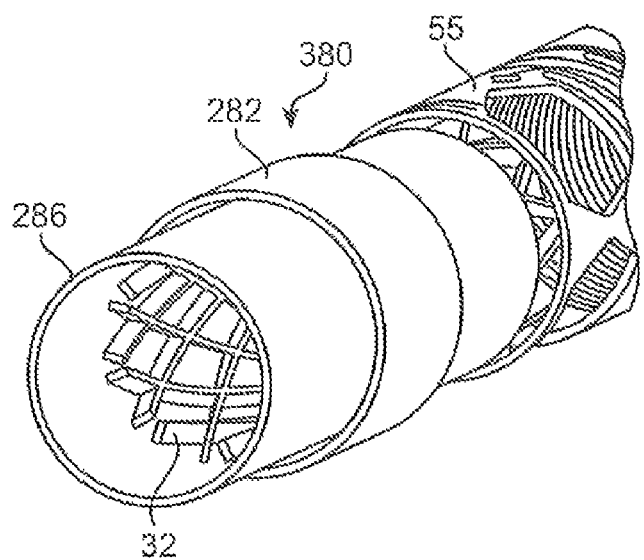

Another embodiment of an energy actuated active stent valve is shown in FIGS. 23A-B. The active stent valve 380 includes a deformable cylinder 282 similar to the cylinder 282 described above in relation to FIGS. 22A-B, but it has been modified such that the force required to deform the cylinder into the open (unengaged) configuration has been reduced. The reduction in required expansion force is accomplished by any of several alternative methods. For example, the walls of the cylinder 282 may be thinned substantially, or cuts or slots may be formed through the walls of the cylinder. The cuts or slots provide an additional advantage to the extent that they allow the cylinder to deform over a larger range of sizes.

A sleeve-shaped layer of elastomeric material 286 is located between the cylinder 282 and the stent segment(s) 32. The elastomeric sleeve 286 is attached to the inner surface of the outer sheath 25 or the garage 55 at its proximal and distal ends, outside of the cylinder 282. The elastomeric sleeve 286 preferably stores potential energy when it is contracted by the cylinder 282, thereby providing a restoring force against the cylinder 282 when the cylinder 282 is expanded. The elastomeric sleeve 286 also protects the stent segment(s) 32 and/or their coatings from being damaged by the cylinder 282 when the cylinder 282 is in its contracted state.

The cylinder 282 is configured to be re-expanded by the inflation balloon 24 carried on the inner shaft of the catheter after the separation process has taken place and prior to the resetting process taking place.

Figure 24:
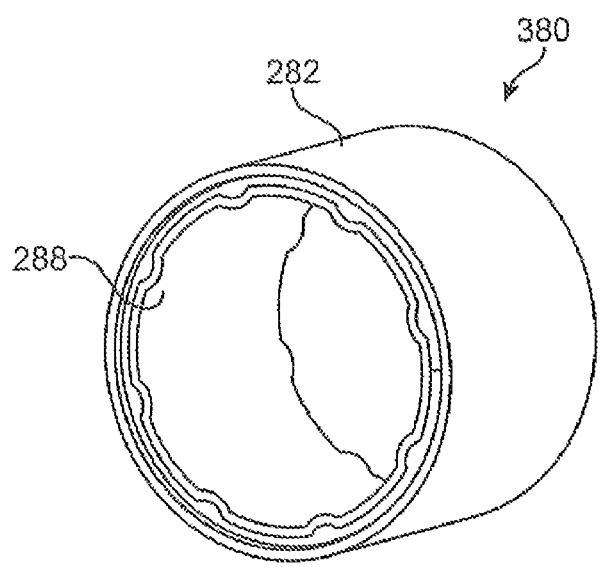
FIG. 24 is a perspective view of another energy actuated stent valve.

Another embodiment of an energy actuated active stent valve is shown in FIG. 24. The active stent valve 380 includes an outer deformable cylinder 282, similar to those described above in relation to FIGS. 22A-B and 23A-B. The outer deformable cylinder 282 is preferably formed of a material having a shape memory that allows it to assume a first, contracted state and a second, expanded state. The outer cylinder 282 is actuated by application of energy, such as electrical or heat energy, by way of at least one electrode that extends from the cylinder 282 to the proximal end of the catheter. The outer cylinder 282 is located within the outer sheath 25 near its distal end.

An inner cylinder 288 is formed within and attached to the outer cylinder 282. The inner cylinder 288 is configured to function as a return element that returns the outer cylinder 282 to its expanded state after the separation process has been completed. For example, in a preferred embodiment the inner cylinder 288 is formed of stainless steel having a thickness such that the inner cylinder 288 possesses a sufficient degree of elasticity upon being compressed by the outer cylinder 282 that the inner cylinder 288 is able to bias the outer cylinder 282 radially outward to return the outer cylinder 282 to its expanded state when the actuation energy is removed from the outer cylinder 288 after the separation process has been completed. Alternatively, the inner cylinder 288 may be formed of a NiTi alloy having superelastic properties that provide a similar outward biased force upon compression by the outer cylinder 288. Other elastic materials may be used to form the inner cylinder 288.

The inner cylinder 288 is reversibly deformable as well as capable of engaging the underlying stent segment(s) without causing damage to them. In some embodiments, the inner cylinder 288 is provided with a coating of a soft, elastic material to provide a cushion between the inner cylinder 288 and the stent segments 32. The inner cylinder 288 preferably buckles, bends, or otherwise deforms when the outer cylinder 282 is activated, thereby storing energy within the inner cylinder 288. The stored energy is then used to restore the outer cylinder 282 to its expanded state when the activation energy is removed. The materials, sizes, shapes, and other physical properties of the inner cylinder 282 and outer cylinder 288 are selected such that a balance is provided between the valving force exerted by the outer cylinder 282 under control of the actuator, and the restoring force provided by the inner cylinder 288.

Figure 25A:
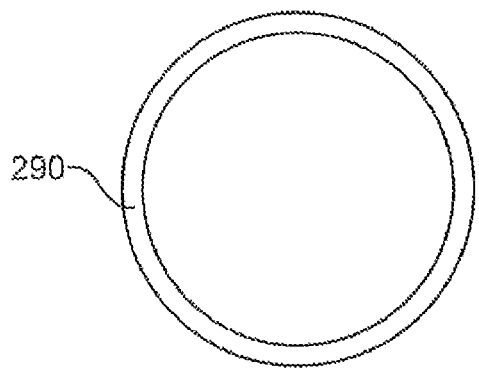
FIGS. 25A-B are schematic views illustrating alternative constriction mechanisms of energy actuated stent valves.
Figure 25B:
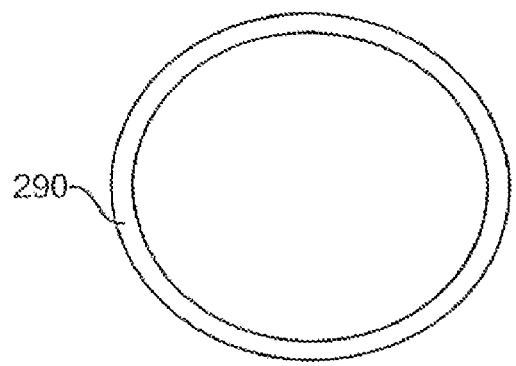

An embodiment of an active component 290 of an energy actuated active stent valve 380 is shown in FIGS. 25A-B. The active component 290 is a variation of the stent valves 380 described above in relation to FIGS. 22A-B, 23A-B, and 24. The active component 290 is illustrated in cross-section, and may represent a cylindrical band, an elongated cylinder, or other structure having a generally circular cross-section. In particular, the active component 290 may comprise the cylinder 282 included in the embodiments described above. The active component 290 is a component of the active stent valve 380 that provides the contracting force used to engage the underlying stent segment(s) 32.

The cross-sectional illustrations shown in FIGS. 25A-B show one of several modes by which the active component deforms to a contracted state in order to provide the foregoing engagement force. In FIG. 25A, the active component 290 is shown in its expanded state, comprising a circular cross-sectional shape. The active component 290 in its expanded state has a sufficient inner diameter to provide clearance for the stent segment(s) 32 to pass through the active component 290. Upon activation, the active component 290 assumes the contracted state shown in FIG. 25B, comprising an oval or elliptical shape. In the contracted state, the active component 290 includes at least one narrowed diameter (or other cross-sectional dimension) that causes the active stent valve 380 associated with the active component 290 to engage the underlying stent segment(s) 32.

As described above in relation to the embodiments illustrated in FIGS. 22A-B, 23A-B, and 24, the active component 290 preferably comprises a shape memory material such as NiTi alloy (Nitinol) that is shape set between its expanded state and its contracted state. Accordingly, the active component 290 is transformed from the expanded state shown in FIG. 25A to its contracted state shown in FIG. 25B by application of an activation energy, typically electricity or heat, by way of electrodes. The active component 290 is returned to its expanded state by removal of the activation energy, and may be assisted by use of the inflation balloon 24 on the catheter or other elastic member associated with the active component 290.

In addition, although the active component 290 shown in FIGS. 25A-B transforms from a circular cross-section in its expanded state to an elliptical or oval cross-sectional shape in its contracted state, other types of transformations are also possible. For example, the active component 290 may be provided with an expanded state and contracted state that comprise a generally triangular, square, or other geometric or irregular shape, provided that at least one diameter (or other cross-sectional dimension) of the active component 290 is reduced in the contracted state relative to the expanded state.

Figure 26A:
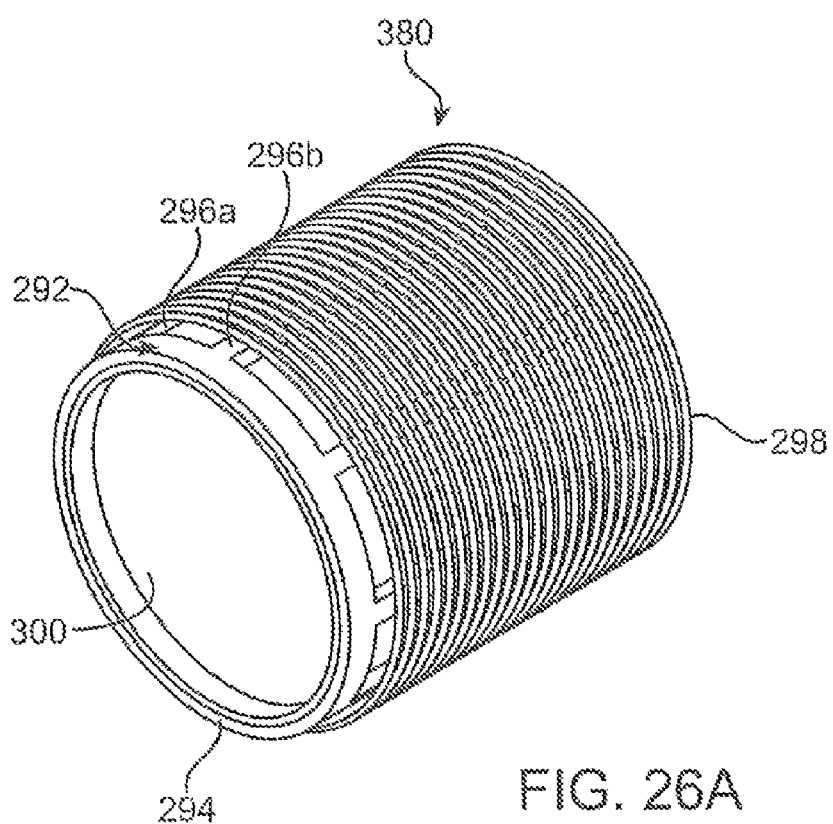
FIGS. 26A-B are perspective and cross-sectional views of another energy actuated stent valve.
Figure 26B:
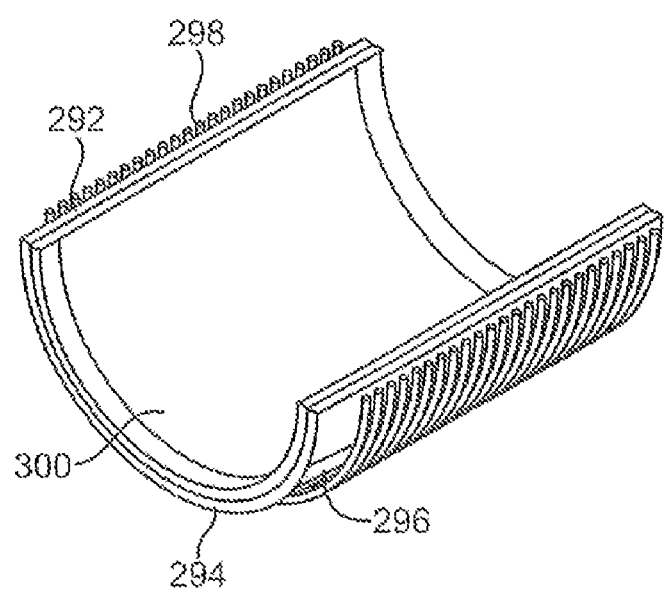

Turning next to FIGS. 26A-B, another embodiment of an active stent valve 380 is shown. The active stent valve 380 includes a tubular element 292 that includes a pair of rings 294 interconnected by a plurality of longitudinal struts 296. The longitudinal struts 296 include a first plurality of strained struts 296a, and a second plurality of deforming struts 296b. The strained struts 296a are formed from a shape memory material, such as NiTi alloy, and are shape set straight and then strained longitudinally. The strained struts 296a then contract longitudinally upon activation, e.g., upon application of heat. When the strained struts 296a contract longitudinally, they cause the pair of rings 294 to move slightly closer to one another, placing a contracting force on the deforming struts 296b. The deforming struts 296b are preferably formed of stainless steel or other material having sufficient elasticity to allow the deforming struts 296b to deform radially inward under the contracting force of the converging rings 294. This radially inward deflection of the deforming struts 296b performs the valving function of the stent valve 380 by allowing the stent valve 380 to engage the stent segment(s) 32 underlying the valve. Due to their elasticity, this deformation causes the deforming struts 296b to store energy and to apply a force against the rings 294 biasing the rings 294 apart. When the strained struts 296a are no longer activated, the energy stored in the deforming struts 296b causes the rings 294 to move apart and return to the original, expanded state.

A wire coil 298 is positioned on the exterior of the tubular element 292. The wire coil 298 is preferably formed of an electrically resistive material such that the wire coil 298 is heated when an electric current is passed through it. The wire coil 298 is connected by a suitable conductor to a source of electricity (e.g., battery) associated with the handle 38 or otherwise accessible at or near the proximal end of the catheter. For example, a conductive wire (not shown) may be embedded within the outer sheath 25 or attached to the inner or outer surface of the outer sheath 25 between the wire coil 298 and the proximal end of the catheter. Upon heating of the wire coil 298, the strained struts 296a of the tubular element 292 are activated, thereby causing the stent valve 380 to engage the underlying stent segment(s) 32 to facilitate the separation process.

An optional inner sleeve 300 is provided on the internal surface of the tubular element 292. The inner sleeve 300 may be formed of a material, such as a soft thermoelastic polymer, that protects the underlying stent segment(s) 32 (or any coatings thereon) from being damaged during the separation process. The inner sleeve 300 may also provide an additional elastic force biasing the tubular element 292 radially outward to assist with restoring the tubular element 292 to its expanded state when the activation energy is removed and the separation process is complete.

The stent valve 380 is operated to facilitate the separation process by causing an electric current to run through the wire coil 298, thereby heating the wire coil. The heat from the wire coil 298 is passed to the tubular element 292, including the strained struts 296a. As the strained struts 296a are heated, they shorten longitudinally, placing a force biasing the rings 294 together, which force is imparted as a compression force to the deforming struts 296b. The compression force causes the deforming struts 296b to buckle or deflect radially inward, thereby engaging the underlying stent segment(s) 32.

Figure 27A:
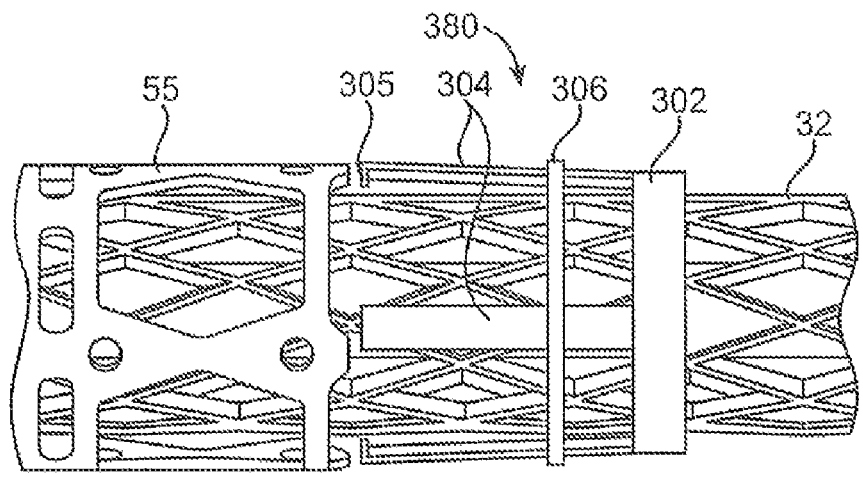
FIGS. 27A-B are side views of another energy actuated stent valve.
Figure 27B:
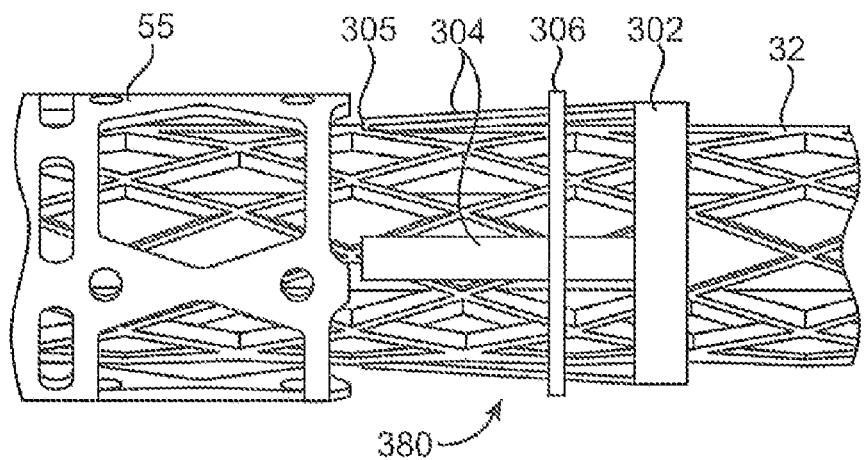

Turning next to FIGS. 27A-B, another embodiment of an active stent valve 380 is shown. The active stent valve 380 includes a tubular element 302 having an inner diameter slightly larger than the outer diameter of the stent segment(s) 32 and attached to or embedded within the inner surface of the outer sheath 25 near its distal end. The tubular element 302 is preferably located near the garage 55, as illustrated in the Figures. The tubular element 302 includes a plurality of cantilevered struts 304 that extend longitudinally from the tubular element 302. Although four cantilevered struts 304 are shown in the embodiment illustrated in FIGS. 27A-B, more or fewer struts may be provided.

A compression ring 306 is located around the periphery of the cantilevered struts 304 and is spaced apart from the tubular element 302 by a short distance. The compression ring 306 is formed of a material or is otherwise provided with the capacity for selectively contracting upon the cantilevered struts 304, thereby biasing the struts 304 radially inward. In the preferred embodiment, the compression ring 306 is formed of shape memory NiTi alloy that is shape set to have a first, expanded state in which it fits around the cantilevered struts 304 without biasing them radially inward (see FIG. 27A), and a second, contracted state (having a relatively smaller diameter than the expanded state) in which the ring 306 biases the cantilevered struts 304 radially inward (see FIG. 27B). The cantilevered struts 304 preferably include a tooth 305 or other gripping element on the end of each cantilevered strut opposite the tubular element 302.

The compression ring 306 is connected to a source of heat energy, such as a resistance wire or other member shown in the embodiments illustrated in, for example, FIGS. 21B and 26A-B. The resistance wire or other heating element is preferably connected to an electrode or other conductor that extends from the heating element to the proximal end of the catheter, where it is connected to a source of electrical or other energy. Upon activation, the heating element is heated, thereby heating the compression ring 306 to cause it to transform from its expanded state (FIG. 27A) to its contracted state (FIG. 27B). Upon contraction of the compression ring 306, the cantilevered struts 304 are biased radially inward, and the ends of the cantilevered struts 304 engage the underlying stent segment(s) 32. The teeth 305 formed on the ends of the struts 304 preferably have a shape, size, and profile configured to positively engage the underlying stent segment(s) 32, rather than relying only upon the friction force between the struts 304 and the stent segment(s) 32.

The struts 304 are preferably formed of stainless steel or other elastic material. The deflection of the struts 304 caused by the compression ring 306 creates potential energy stored in the struts 304. When the activation energy is removed from the compression ring 306, such as by stopping the heating of the heating element, the compression ring 306 cools and returns to its expanded state. The return is facilitated by the elastic force stored in the cantilevered struts 304, which bias the compression ring 306 to its expanded state.

Figure 28A:
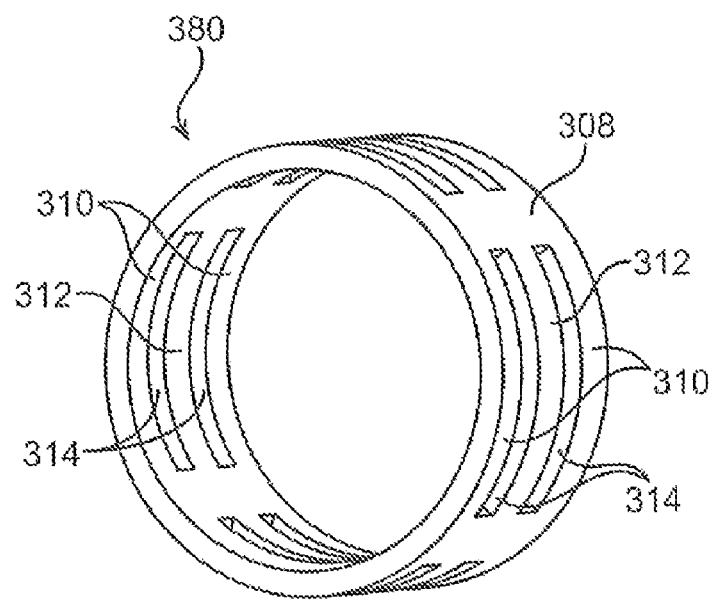
FIGS. 28A-B are perspective views of another energy actuated stent valve.
Figure 28B:
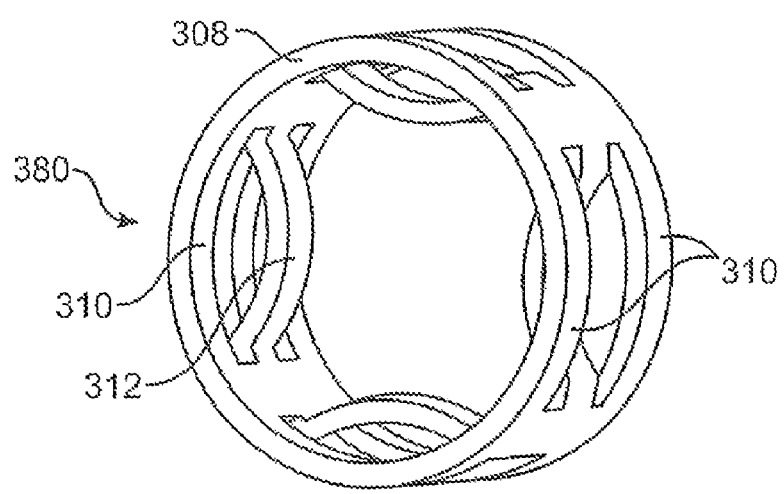

Another embodiment of an active stent valve 380 is illustrated in FIGS. 28A-B. The illustrated stent valve 380 operates in a similar manner to the embodiment described above in relation to FIGS. 26A-B. In particular, the stent valve 380 includes a generally tubular element 308 having a plurality of circumferential fixed struts 310 and at least one circumferential deforming strut 312. The deforming struts 312 are preferably separated from the fixed struts 310 by gaps 314 formed in the tubular element 308.

In the preferred embodiment, at least the deforming struts 312 are formed of a shape memory material, such as NiTi alloy, that is shape set such that the deforming struts 312 have an expanded state in which the deforming struts 312 follow the generally cylindrical curvature of the tubular element 308, and a contracted state in which the deforming struts 312 are deflected radially inward, creating at least a portion of the tubular element 308 having a narrowed diameter. The remainder of the tubular element 308, including the fixed struts 310, may also be formed of NiTi alloy, or it may be formed of stainless steel or other suitable material. The transformation of the deforming struts 312 from the expanded state to the contracted state is activated by application of heat or other suitable energy. Preferably, a heating element is attached to or otherwise brought into contact with the deforming struts 312. A suitable heating element is the wire coil 298 described above in relation to the stent valve illustrated in FIGS. 26A-B. A similar wire coil 298 may be incorporated into the stent valve 22 shown in FIGS. 28A-B. Other suitable heating elements may also be used.

The stent valve 380 operates in a similar manner to the stent valves described above. When the tubular element 308 is in its expanded state, as shown in FIG. 28A, the stent segment(s) 32 are allowed to pass through the stent valve 380 without frictionally engaging the stent valve 380, such as when the outer sheath 25 is retracted during the paving process. Upon activation of the stent valve 380 by application of heat or other energy to the deforming struts 312, the deforming struts 312 deflect radially inward, (see FIG. 28B), to frictionally engage the underlying stent segment(s) 32. This engagement facilitates the separation process by causing retraction of the outer sheath 25 to also retract the column of stent segment(s) 32 retained within the outer sheath 25. After separation, the activation energy supplied to the stent valve 380 is stopped, thereby allowing the deforming struts 312 to cool and return to their expanded state, as shown in FIG. 28A. Restoration of the deforming struts 312 to their expanded state may be further assisted by expansion of the expandable member 24.

Figure 29A:
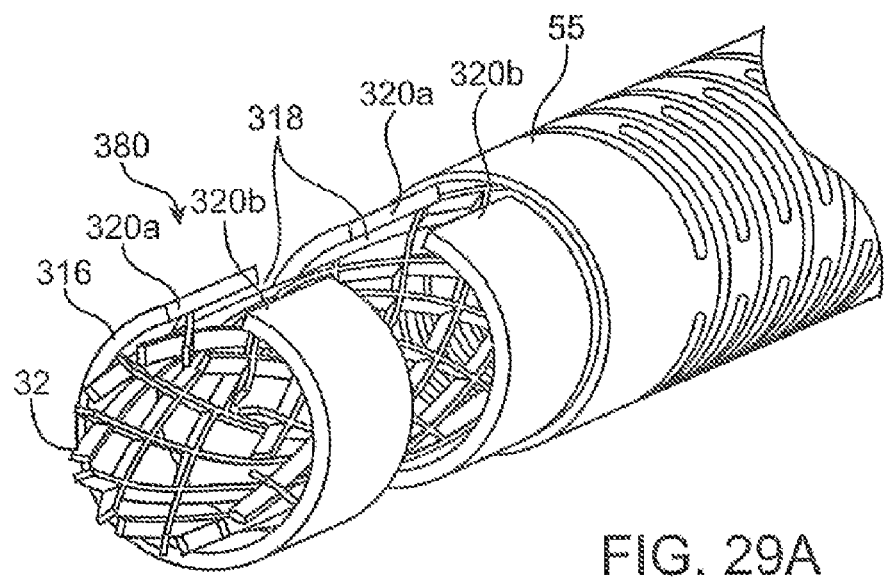
FIG. 29A-B are perspective views of another energy actuated stent valve.
Figure 29B:
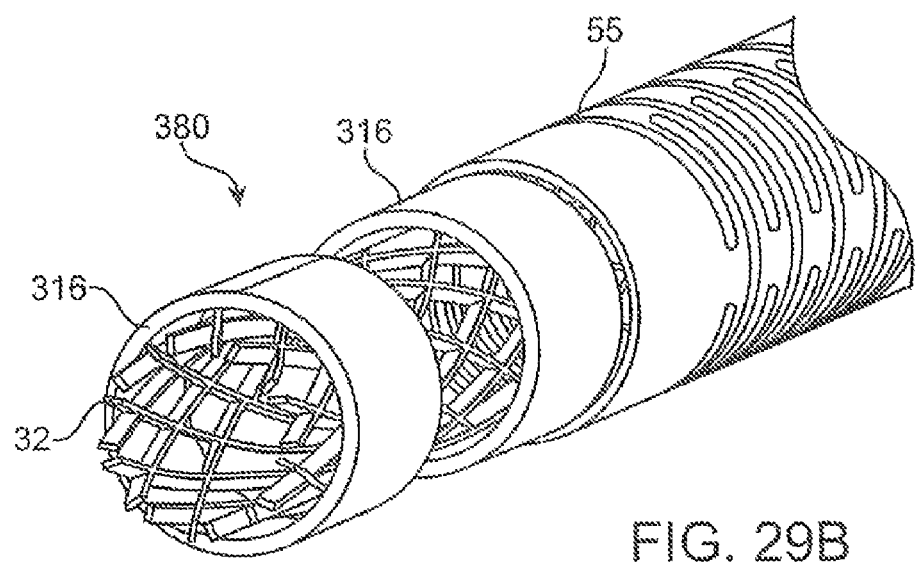
Figure 30A:
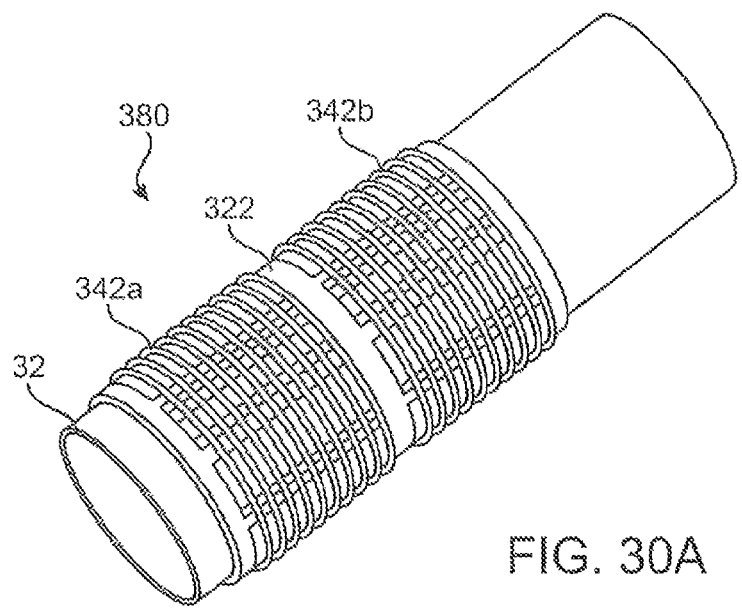
FIG. 30A-C are perspective views of another energy actuated stent valve and its components.
Figure 30B:
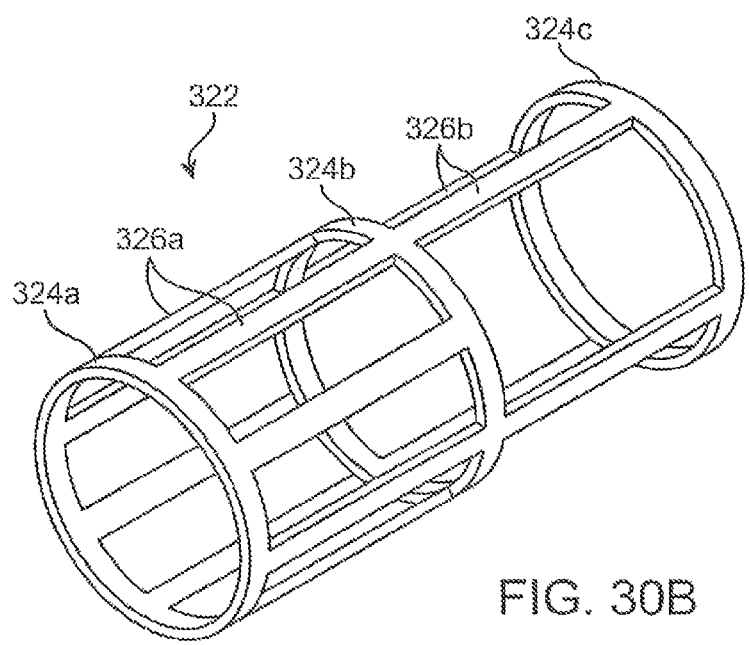
Figure 30C:
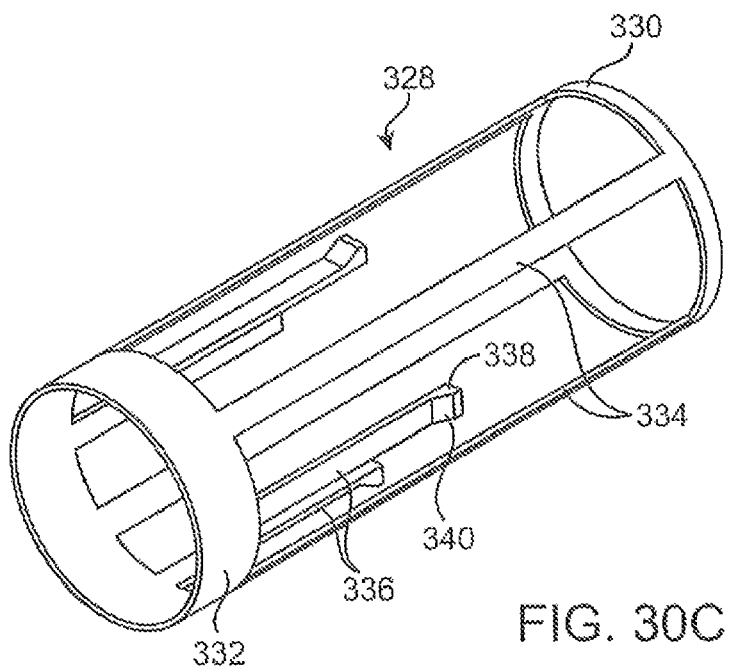
Figure 30D:
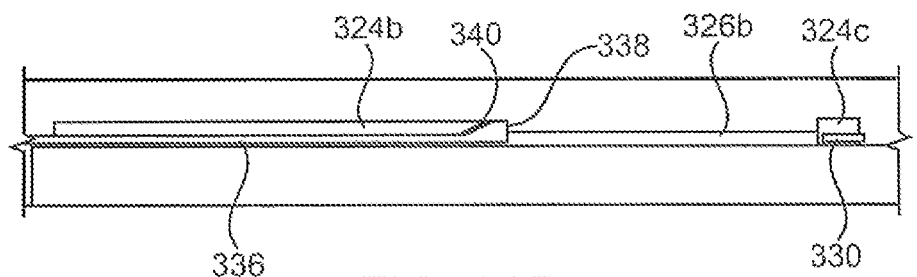
FIG. 30D-E are side views of a portion of the energy actuated stent valve shown in FIGS. 30A-C.
Figure 30E:
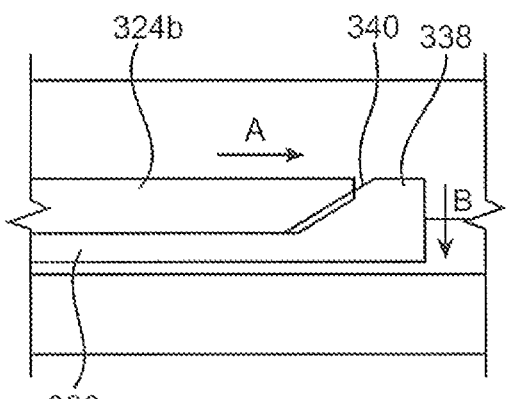

Turning next to FIGS. 29A-B, another embodiment of an active stent valve 380 is shown. The stent valve 380 includes one or more tubular elements 316, each having an expanded state that includes a generally "C"-shaped cross-sectional shape, including a continuous semi-circular portion and a gap 318 between the opposed ends 320a, 320b of the semi-circular portion. (See FIG. 29A). The tubular elements 316 also have a contracted state in which the gap is substantially closed by bringing the opposed ends 320a, 320b of the tubular element 316 into contact or near proximity to each other. (See FIG. 29B). The tubular elements 316 are preferably attached to or formed integrally within the inner surface of the outer sheath 25 at or near its distal end. In the expanded state, the tubular elements 316 have a first interior diameter that is sufficiently large to allow passage of the stent segment(s) 32 therethrough, such as during the paving process. In the contracted state, the tubular elements 316 have a second interior diameter, smaller than the first interior diameter, and that is sufficiently small that it creates a frictional engagement between the tubular elements 316 and the underlying stent segment(s) 32, thereby preventing relative motion between the engaged stent segment(s) 32 and the outer sheath 25 to which the tubular elements 316 are attached. This engagement facilitates the separation process, as described above.

The transformation of the tubular elements 316 from the expanded state (FIG. 29A) to the contracted state (FIG. 29B) is obtained by any suitable mechanism or method. In the preferred embodiment, the tubular elements 316 are formed of a shape memory material, such as NiTi alloy, that is shape set to transform between the expanded and contracted states in response to the application of heat or other energy. For example, the tubular element 316 may be laser cut from a straight shape set section of NiTi alloy. A suitable heating element, such as the wire coil 298 described above in relation to FIGS. 26A-B, is attached to, wrapped around, or otherwise placed adjacent to each of the tubular elements 316. The heating element is preferably conductively connected to a source of activation energy, such as a battery or other source of electricity, by way of a conductor extending through the catheter to its proximal end. The energy source is engaged when it is desired to heat the heating element, and disengaged in order to allow the heating element to cool.

Accordingly, the stent valve 380 is operated by selectively engaging the source of activation energy, such as by a switch provided on the handle 38. The heating element then heats each of the tubular elements 316, causing the tubular element to transform to the contracted state and engage the underlying stent segment(s) 32. Upon this transformation, retraction of the outer sheath 25 causes the column of stent segment(s) 32 located within the outer sheath 25 to separate from the exposed stent segment(s) 32, in the manner illustrated in FIG. 5B-C. Once the separation process is completed, the activation energy is removed, thereby allowing the tubular elements 316 to transform back to the expanded state. The transformation may be aided by using the expandable member 24 to reset the tubular elements 316 to the expanded state. Alternatively, the transformation may be aided by provision of a deformable structural element, such as a spring, in the gap 318. The deformable structural element would store energy when compressed during the transformation of the tubular elements 316 to the contracted state, which stored energy would then be used to expand the tubular elements 316 when the separation process is completed.

Although two tubular elements 316 are shown in the embodiment illustrated in FIGS. 29A-B, fewer (e.g., one) or more tubular elements may be used in the stent valve 380. One advantage of using multiple tubular elements 316 is that the force required to engage each individual stent segment 32 may be lessened when multiple tubular elements 316 are provided, as the forces required to facilitate the separation process are spread across more stent segment(s) 32 and more tubular elements 316.

Turning next to FIGS. 30A-E, another embodiment of an active stent valve 380 includes a pair of nested tubular elements configured to provide a valving force for restraining movement of a column of stent segment(s) 32 located internally of the tubular elements. A first tubular element 322, shown in detail in FIGS. 30A-B, includes a plurality of rings 324 interconnected by a plurality of longitudinal struts 326. The first tubular element 322 is configured to provide selective longitudinal movement of at least one of its components, as explained more fully below. The stent valve 380 also includes a second tubular element 328 having at least a proximal ring 330 and a distal ring 332, and having a plurality of longitudinal struts 334. (See FIGS. 30B-E). The second tubular element 328 also includes a plurality of clamping elements 336 that extend from one of the rings 330, 332. Each of the clamping elements 336 includes a tab 338 having a ramped section 340 on its outward facing surface.

The first tubular element 322 is preferably constructed of NiTi alloy, or other shape memory material that is reactive to the application of energy, such as heat or electricity. In the illustrated embodiment, the first tubular element 322 includes a distal ring 324a, a center ring 324b, and a proximal ring 324c. The distal ring 324a and center ring 324b are connected by a plurality of distal struts 326a. The proximal ring 324c and the center ring 324b are connected by a plurality of proximal struts 326b. The distal struts 326a and proximal struts 326b are shape set in such a manner that, upon exposure to a source of activation energy, the contraction and expansion of these members cause the center ring 324b to move toward the proximal ring 324c and back. Alternatively, the location and number and relative location and number of distal struts 326a and proximal struts 326b provide the movement of the center ring 324b.

The active stent valve 380 illustrated in the Figures includes two heating elements 342a, 342b. The first heating element 342a is in the form of a wire coil that is wrapped around the distal struts 326a of the first tubular element 322. The second heating element 342b is also a wire coil that is wrapped around the proximal struts 326b of the first tubular element 322. Each of the heating elements 342a, 342b is able to be operated independently, thereby providing the user with the ability to separately and selectively heat the distal struts 326a and proximal struts 326b. Each of the heating elements 342a, 342b is connected to a source of heat or electrical energy by a conductor, such as a wire attached to or embedded within the outer sheath 25 of the catheter. The energy source may be a battery contained within the handle 38, or other suitable energy source.

The second tubular element 328 is nested within the first tubular element 322 such that the tabs 338 contained on the ends of the clamping elements 336 are adjacent to but just proximal of the center ring 324b of the first tubular element 322. (See FIGS. 30D-E). Accordingly, as the center ring 324b moves proximally (see arrow "A" in FIG. 30E), it engages the ramped section 340 of each of the clamping elements 336, thereby biasing the tab 338 of each of the clamping elements 336 radially inward (see arrow "B" in FIG. 30E). This movement causes each of the tabs 338 to engage any stent segment 32 that is underlying the stent valve 380, thereby facilitating the separation process in the manner described above.

Movement of the center ring 324b of the first tubular element 322 relative to the clamping elements 336 of the second tubular element 328 is provided by proper selection of the materials and construction of the first tubular element 322. A particularly preferred mechanism is to form the first tubular element of a shape memory material, such as NiTi alloy, that is shape set to provide the desired movement. For example, the distal struts 326*a* and proximal struts 326*b* of the first tubular element 322 are preferably formed having approximately the same length. The proximal struts 326*b* are shape set to cause them to contract when activated by the second heating element 342*b*. The distal struts 326*a* are shape set to cause them to contract when activated by the first heating element 342*a*. Each of the sets of struts, upon activation, will attempt to shorten, and in doing so will strain the inactive opposing section of the first tubular element 322. For example, activation of the proximal struts 326*b* will create strain in the distal struts 326*a*, thereby moving the center ring 324*b* proximally and causing the tabs 338 of each of the clamping elements 336 to bias radially inward, engaging the underlying stent segment(s) 32.

After the separation process is complete, the stent valve may be reset by deactivating the second heating element 342*b* and activating the first heating element 342*a*. This will cause the distal struts 326*a* to attempt to shorten, and creates strain in the proximal struts 326*b*, thereby moving the center ring 324*b* distally back to its original position. In this manner, the center ring 324*b* is moved in a longitudinal manner by proper control of activation of the heating elements 342*a*, 342*b*.

In the foregoing embodiment, displacement of the tabs 338 of the clamping elements 336 is adjusted by selection of the angle of the ramped surfaces 340 of the tabs 338, by the overall length of the tubular elements 322, 328, by the number and thicknesses of the distal struts 326*a* and proximal struts 326*b* of the first tubular element 322, and by other similar structural modifications recognized by a person of ordinary skill in the art.

Figure 31A:
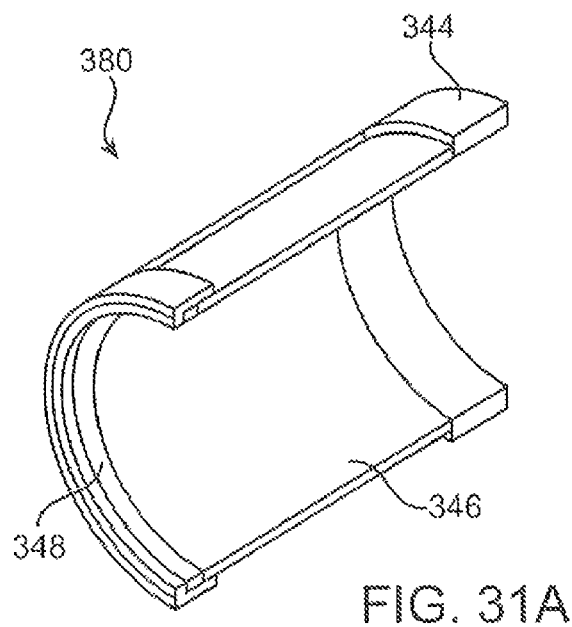
FIGS. 31A-B are cross-sectional views of two embodiments of another energy actuated stent valve.
Figure 31B:
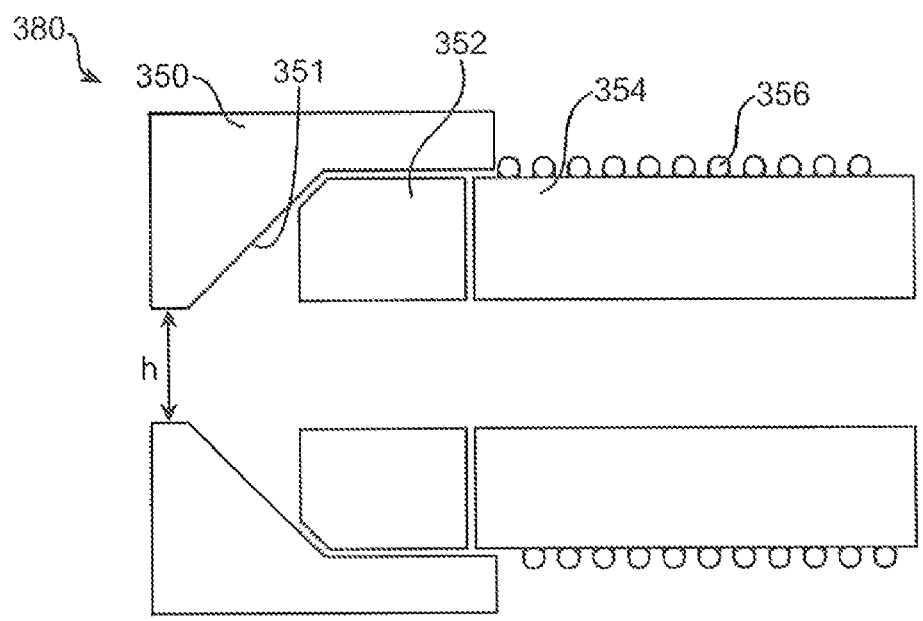

Turning next to FIGS. 31A-B, other embodiments of an active stent valve 380 is illustrated. The stent valve 380 embodiments shown in the Figures include a Touhy-Borst style fitting that is adapted to engage a stent segment(s) 32 located within the stent valve 380 when the stent valve is activated. Two such embodiments are illustrated. As with the other active stent valve 380 embodiments, the stent valve 380 is adapted to be received and retained on the inner surface of the outer sheath 25 near its distal end.

In the first embodiment, shown in FIG. 31A, a rigid cylindrical retainer 344 is provided with an inner surface adapted to receive and retain a cylindrical expansion element 346 and a cylindrical elastomeric member 348. The retainer 344 is preferably formed of stainless steel or other rigid, resilient material having sufficient strength to retain the expansion element 346 and elastomeric member 348 in place. The expansion element 346 is preferably formed of a shape memory material, such as NiTi alloy, such that the expansion element is capable of expanding longitudinally within the space provided for it on the inner surface of the retainer 344. The elastomeric member 348 is preferably formed of an elastomeric polymer material, such as rubber, polyurethane, or similar material, such that the elastomeric member is capable of being expanded elastically deformed and deflected under force applied by the expansion element 346. In the preferred embodiment, the elastomeric member 348 has a relatively short cylindrical shape and it is provided adjacent to the expansion element 346 on the inner surface of the retainer 344.

The expansion element 346 is contacted by a heating element that is conductively connected to a source of heat or electricity located on or near the handle 38. For example, a heating element such as those described above in relation to FIG. 30A or 26A-B may be provided in contact with or surrounding the expansion element 346. The expansion element 346 is preferably shape set such that it expands longitudinally upon activation. Accordingly, when the activation energy is applied, such as by heating a heating element, the expansion element 346 expands longitudinally and engages the elastomeric member 348. As the expansion element 346 expands further, it causes the elastomeric member to deflect radially inward. The radial inward deflection is the only possible movement available to the elastomeric member 348 because of the presence of the retainer 344 on all other sides of the elastomeric member 348. This inward radial movement causes the elastomeric member 348 to engage a stent segment (s) 32 underlying the elastomeric member 348, thereby preventing relative movement between the stent segment(s) 32 and the stent valve 380 attached to the outer sheath 25. This engagement thereby facilitates the separation process described above in relation to FIGS. 5B-C.

In the second embodiment, illustrated in FIG. 31B, a rigid retainer 350 surrounds an elastomeric member 352. The retainer is generally cylindrical, and is provided with a conical inner surface 351. The conical inner surface 351 terminates at the distal end of the retainer where a gap "h" is provided. The gap "h" is preferably of a size large enough to allow passage of the stent segment(s) 32 with adequate clearance to prevent hang-ups or inadvertent engagements. The elastomeric member 352 has a relatively short cylindrical shape, and is in contact with the inner surface of the retainer 350. A generally cylindrical expansion element 354 is adjacent to the elastomeric member 352. As shown in FIG. 31B, a portion of the expansion element 354 may extend outside of the retainer 350. Alternatively, the expansion element 354 may be fully contained within the retainer 350. In either case, the expansion element 354 is fixed in position relative to the retainer 350, as both components are attached to or formed integrally within the inner surface of the outer sheath 25 of the catheter. As with the embodiment shown in FIG. 31A, the expansion element 354 preferably comprises a shape memory material, such as NiTi alloy.

A heating element 356 is attached to or placed adjacent to the expansion element 354. The preferred heating element is a wire coil that is wrapped around the expansion element 354, as shown in FIG. 31B. The expansion element 354 is shape set such that it expands longitudinally upon activation. Accordingly, when the heating element 356 is heated, the expansion element 354 expands longitudinally to cause the elastomeric member 352 to be deflected into the conical side wall 351 of the retainer 350. As the expansion element 354 expands further, the elastomeric member 352 is deflected radially inward until it engages a stent segment(s) 32 located radially inward of the elastomeric member 352. This prevents movement of the stent segment(s) 32 relative to the stent valve 380, which is attached to or formed integrally with the inner surface of the outer sheath 25 of the catheter. Accordingly, the stent valve 380 facilitates the separation process in the manner described above in relation to FIGS. 5B-C. Removal of the activation energy (e.g., heat or electricity) causes the expansion element 354 to return to its normal state, thereby allowing the elastomeric member 352 also to return to its normal state, releasing the stent segment(s) 32.

Figure 32:
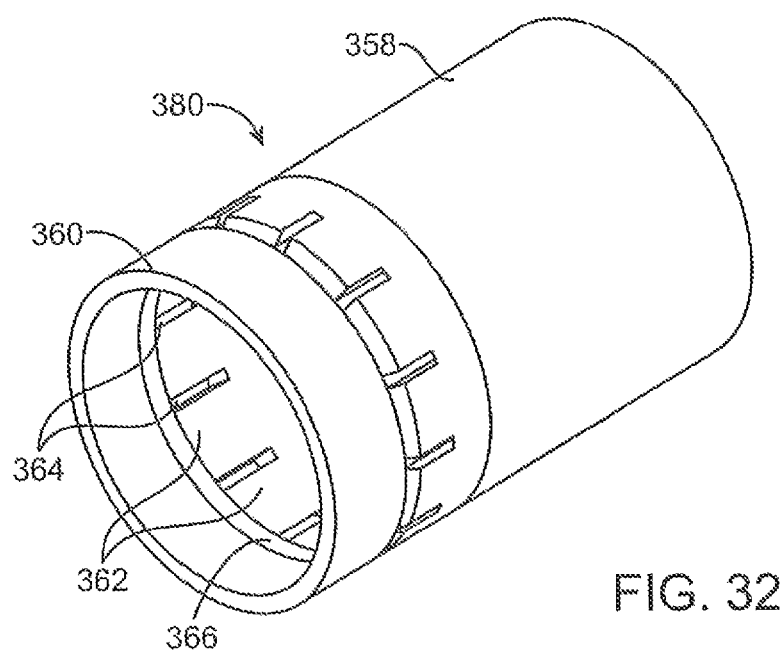
FIG. 32 is a perspective view of another energy actuated stent valve.

Turning next to FIG. 32, another embodiment of an active stent valve 380 is shown. The embodiment includes a collet structure that includes an expanding member that is preferably formed of a shape memory material, such as NiTi alloy, and that operates in a manner similar to the Touhy-Borst style stent valves described above. Turning to the Figure, the stent valve 380 includes an expansion element 358 and a retainer 360. Each of the expansion element 358 and the retainer 360 are preferably generally cylindrical, although other shapes for these components are possible. The expansion element 358 is formed of a material that is longitudinally expandable, such as a shape memory material. NiTi alloy is preferred. The retainer 360 is preferably formed of a rigid material such as stainless steel or other suitable metallic material.

The expansion element 358 includes a plurality of deformable fingers 362 on one end thereof. The fingers 362 preferably comprise thinned portions of the expansion element 358 that are separated by a plurality of longitudinal gaps 364 formed in the expansion element 358. The fingers 362 are adapted to deform radially inward as the fingers 362 engage the inner surface of the retainer 360. The expansion element 358 is shape set to expand longitudinally upon activation.

The retainer 360 is preferably ring-shaped, and preferably has a conical engagement surface 366 on the inner surface that engages the deformable fingers 362 of the expansion element 358. Accordingly, when the expansion element 358 is activated, such as by application of heat or electricity from a heating element, the expansion element 358 expands longitudinally, causing the deformable fingers 362 to engage the inner conical surface 366 of the retainer 360. This causes the fingers 362 to deflect radially inward to engage the underlying stent segment(s) 32. This action facilitates the separation process, as described above in relation to FIGS. 5B-C. Removal of the activation energy allows the expansion element 358 to return to its normal state, thereby allowing passage of stent segment(s) 32 through the stent valve 380.

Figure 33:
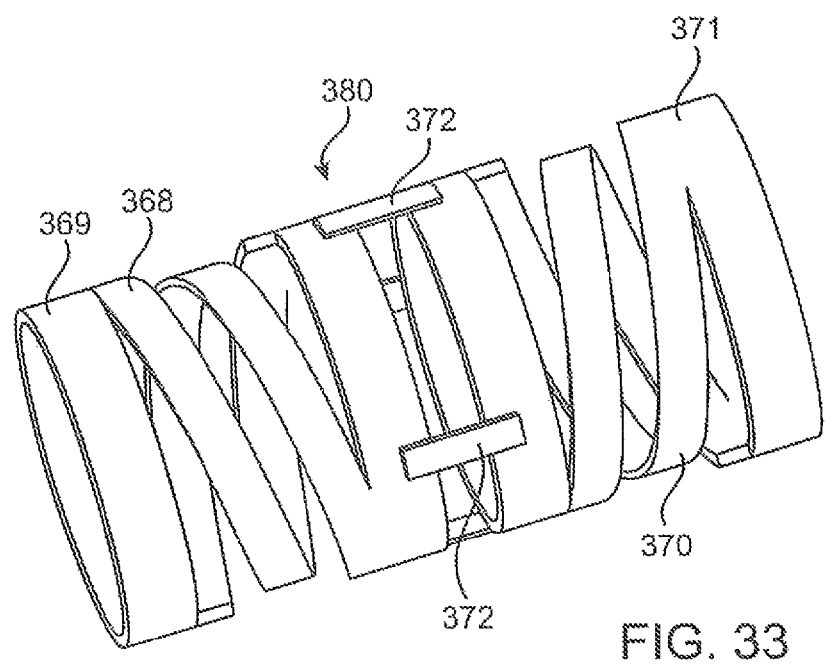
FIG. 33 is a perspective view of another energy actuated stent valve.

Turning next to FIG. 33, another embodiment of an active stent valve 380 is shown. The stent valve 380 includes a first torsion spring 368 attached to a second torsion spring 370, each of which is operatively attached to the inner surface of the outer sheath 25 near its distal end. The stent valve 380 is attached to the catheter such that the opposed ends 369, 371 of each of the first spring 368 and second spring 370 are rotationally fixed relative to one another, while the intermediate section of the stent valve 380 is able to rotate in the manner described below. The torsion springs 368, 370 are attached end-to-end, with each spring opposing the other. In the preferred embodiment, one of the springs is formed of a shape memory material, such as NiTi alloy, that is shape set to constrict when activated, as described more fully below. The other spring is preferably formed of stainless steel or other resilient material suitable for storing energy created by the constriction of the first spring, as described more fully below. The two springs are attached to each other by any suitable means, such as by a plurality of connectors 372.

In the embodiment shown in FIG. 33, the first spring 368 is formed of NiTi alloy that is shape set by constraining one end of the spring while the other end is subjected to a moment about the longitudinal axis. This moment is applied such that the spring reduces in internal diameter. The spring 368 is shape set in this configuration and an opposite moment is applied to return the inner diameter to the original size. Upon activation, the spring 368 rotates back to the shape memory configuration having a relatively smaller inner diameter, thereby engaging the stent segment(s) 32 located radially inward of the first spring 368. This engagement facilitates the separation process, as described above in relation to FIGS. 5B-C. A heating element may be used to activate the spring. A preferred heating element is a wire coil such as those described above in relation to FIGS. 26A-B, 30A, and 31B. The heating element may be wrapped around the first spring 368 or otherwise placed adjacent to or near the first spring 368, and is conductively connected to a source of electrical or heat energy located on the handle 38 or otherwise accessible to the proximal end of the catheter.

Upon activation, the rotation of the first spring 368 causes the opposed second spring 370 to rotate in the same direction, thereby storing energy in the second spring 370. The energy stored in the second spring 370 creates a force biased against the rotation of the first spring 368, thereby providing a restoring force to the first spring 368. When activation of the first spring 368 is ceased, the energy stored in the second spring 370 causes the second spring 370 to rotate back to its original state, and also causes the first spring 368 to return to its original state.

Another active stent valve embodiment is illustrated in FIGS. 34A-F. The stent valve 380 includes a pair of concentric cylinders including an outer cylinder 374 and an inner cylinder 376. A schematic representation of a stent segment 32 carried by the catheter inner shaft is shown extending through the pair of cylinders. Each of the cylinders is preferably formed of NiTi alloy, although only the outer cylinder 374 is shape set. The inner cylinder 376 is formed of NiTi alloy in order to take advantage of the superelastic properties of the material, as described below.

Figure 34A:
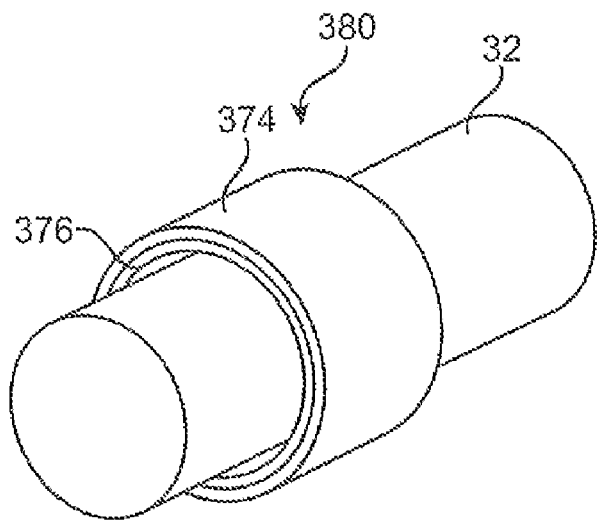
FIGS. 34A-B are perspective views of another energy actuated stent valve.
Figure 34B:
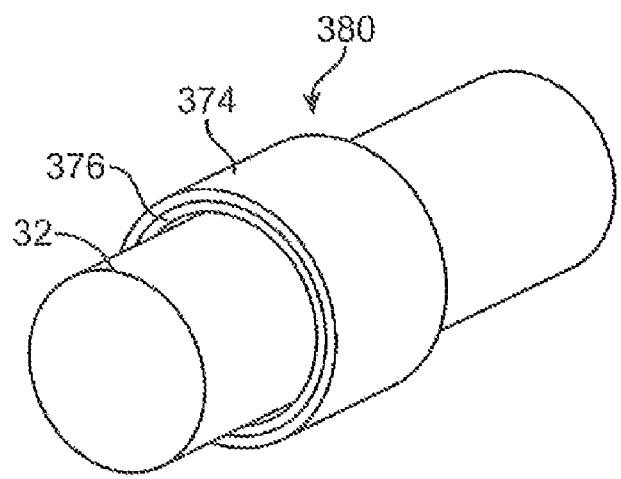

The outer cylinder 374 is shape set such that, when activated, the outer cylinder 374 transforms from a first state having an inner diameter sufficient to allow the stent segment 32 to freely pass through the pair of cylinders (see FIG. 34A), to a second state having a smaller inner diameter such that the inner cylinder 376 is forced into engagement with the underlying stent segment 32, as shown in FIG. 34B. The outer cylinder 374 is maintained in the first, expanded state during the paving and reset operations of the catheter, and is activated to the second, contracted state in order to perform the separation process. A heating element—such as a wire coil described above in relation to FIGS. 26A-B, 30A, and 31B— is wrapped around or otherwise placed in contact with the outer cylinder 374 in order to provide a controllable source of heat to activate the outer cylinder.

Figure 34C:
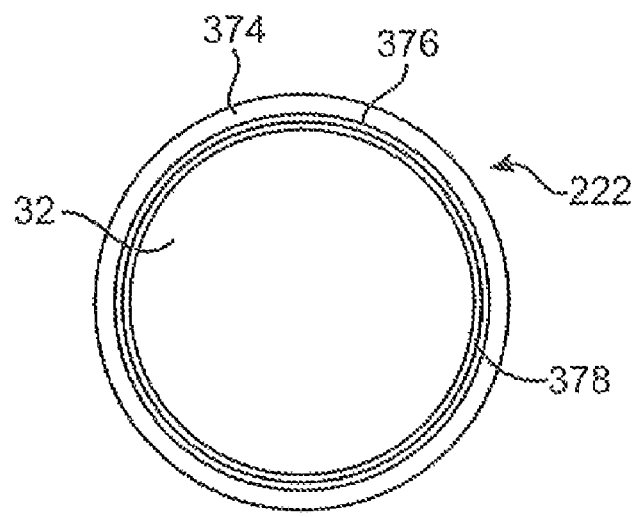
FIGS. 34C-F are cross-sectional views of the energy actuated stent valve shown in FIGS. 34A-B.
Figure 34D:
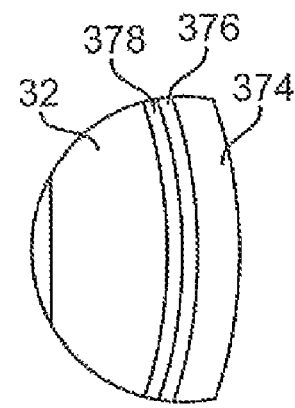
Figure 34E:
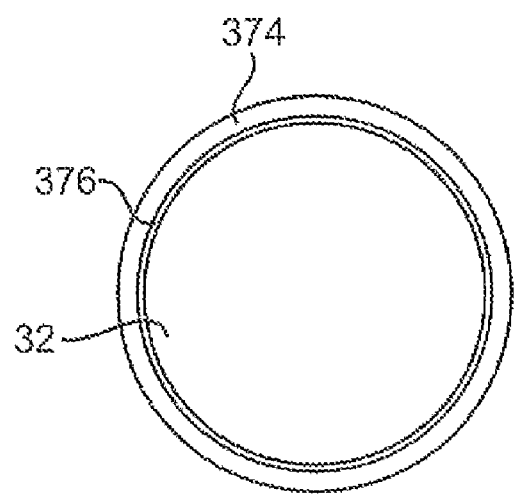
Figure 34F:
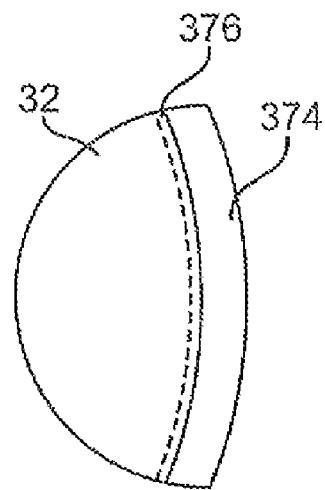

FIGS. 34C-F provide additional detail concerning the operation of the stent valve 380. In FIGS. 34C-D, the stent valve 380 is shown in its normal state, in which a small gap 378 is provided between the inner cylinder 376 and the stent segment 32. Upon activation, shown in FIGS. 34E-F, the outer cylinder 374 contracts and causes the inner cylinder 376 to engage the stent segment 32, eliminating the gap 378 between the two components.

When the outer cylinder 374 is activated, it contracts with sufficient force also to contract the inner cylinder 376. Due to its superelastic properties, the inner cylinder 376 stores energy when it is contracted, which energy creates a force biasing the inner cylinder 374 radially outward. As long as the outer cylinder 374 is activated, the restoring force of the inner cylinder 376 is insufficient to cause the cylinders to return to the normal state. However, upon removal of the activation energy from the outer cylinder 374, the restoring force of the inner cylinder 376 causes both of the cylinders 374, 376 to return to the normal state, thereby allowing passage of stent segments 32 through the stent valve 380.

The stent valve 380 is operated in order to facilitate the separation process. When an activation energy is applied, the outer cylinder 374 contracts, causing the inner cylinder 376 to engage the underlying stent segment 32. This engagement prevents movement of the stent segment 32 and all stent segments 32 in the column beneath the outer sheath 25 from moving relative to the outer sheath 25. As the outer sheath 25 is withdrawn, the stent segments 32 are separated from those stent segments 32 that are exposed outside of the outer sheath 25, as shown in FIGS. 5B-C. After the separation process is complete, the activation energy is ceased, and the inner cylinder 374 causes the outer cylinder 374 to restore to its normal state.

4. Piezo Crystal Stent Valve

Another alternative embodiment of a stent valve that includes a restraining mechanism formed of piezoelectric crystal members is illustrated in FIGS. 36A-D. Piezoelectric crystals, when subjected to an externally applied voltage, can change shape by a small amount. Although a detailed description of piezoelectricity and the composition and mode of operation of piezo crystals is beyond the scope of the present application, these materials are well known to persons of ordinary skill in the art.

The stent valve 390 includes a piezo crystal laminate 392 that is preferably in the form of a semi-cylinder, such as that illustrated in FIG. 36B. In the preferred embodiment, the piezo crystal laminate 392 is a multi-layer laminate structure having a plurality of piezoceramic layers, a plurality of electrode layers, a plurality of adhesive layers, and an optional center shim for mechanical strength and stiffness. The piezo crystal laminate 392 is constructed such that, upon activation of a drive voltage, the piezo crystal laminate 392 is able to deflect or bend inwardly at its outer edges 394a, 394b.

The piezo crystal laminate 392 is attached to the inner surface of the outer sheath 25 of the delivery catheter near its distal end. (See FIG. 36A). More particularly, the center portion of the laminate 392 is attached to the inner surface of the outer sheath 25, leaving the outer edges 394a, 394b free to move within the gap between the outer sheath 25 and the underlying stent segments 32. (See FIGS. 36C-D). As shown in FIG. 36C, the portion of the laminate that is bonded or otherwise attached to the outer sheath 25 is identified by the designation "b".

An electrical conductor 396, such as an insulated wire, is attached to the piezo crystal laminate 392 and extends proximally to the proximal end of the delivery catheter. The conductor 396 may be attached to the inner surface of the outer sheath 25, or, alternatively, the conductor 396 may be embedded within the outer sheath 25. The proximal end of the conductor 396 is operatively connected to a source of electrical energy, such as a battery or the like. In the preferred embodiment, a switch 205 is provided on the handle 38 (see FIG. 1) to allow the user to operate the stent valve by selectively closing the switch to provide a drive voltage to the piezo crystal laminate 392 by way of the conductor 396.

Turning to FIGS. 36C-D, when the drive voltage is not provided to the crystal laminate 392, the outer edges 394a, 394b of the laminate are located against the inner surface of the outer sheath 25, and do not engage the underlying stent segment(s) 32. (See FIG. 36C). This position of the piezo crystal laminate 392 corresponds with the paving and resetting processes of the delivery catheter, described above in relation to FIGS. 5A-E. During these processes, the stent segments 32 carried by the inner shaft of the catheter are allowed to pass freely through the outer sheath 25. Upon application of the drive voltage, the outer edges 394a, 394b of the laminate are biased radially inward, toward the underlying stent segment 32. (See FIG. 36D). The biasing force is sufficient to cause the piezo crystal laminate 392 to engage the stent segment(s) 32 and prevent movement of those segment(s) 32 relative to the stent valve, and relative to the outer sheath 25. This engagement thereby facilitates the separation process, described above in relation to FIGS. 5B-C.

An optional protective coating or other layer may be provided on the piezo crystal laminate 392 in order to protect the underlying stent segment(s) 32 or any coatings that may be contained thereon.

B. Non-Valve Restraining, Separation, and Deployment Mechanisms

In addition to the active stent valves described above, the present invention includes several non-valve restraining, separation, and stent deployment mechanisms that operate in connection with the delivery catheters described herein to restrain movement of the stent segments relative to the outer sheath or otherwise facilitate the separation and/or deployment processes. Several embodiments of these non-valve restraining, separation, and deployment mechanisms are described below.

1. Release Wires

Figure 37:
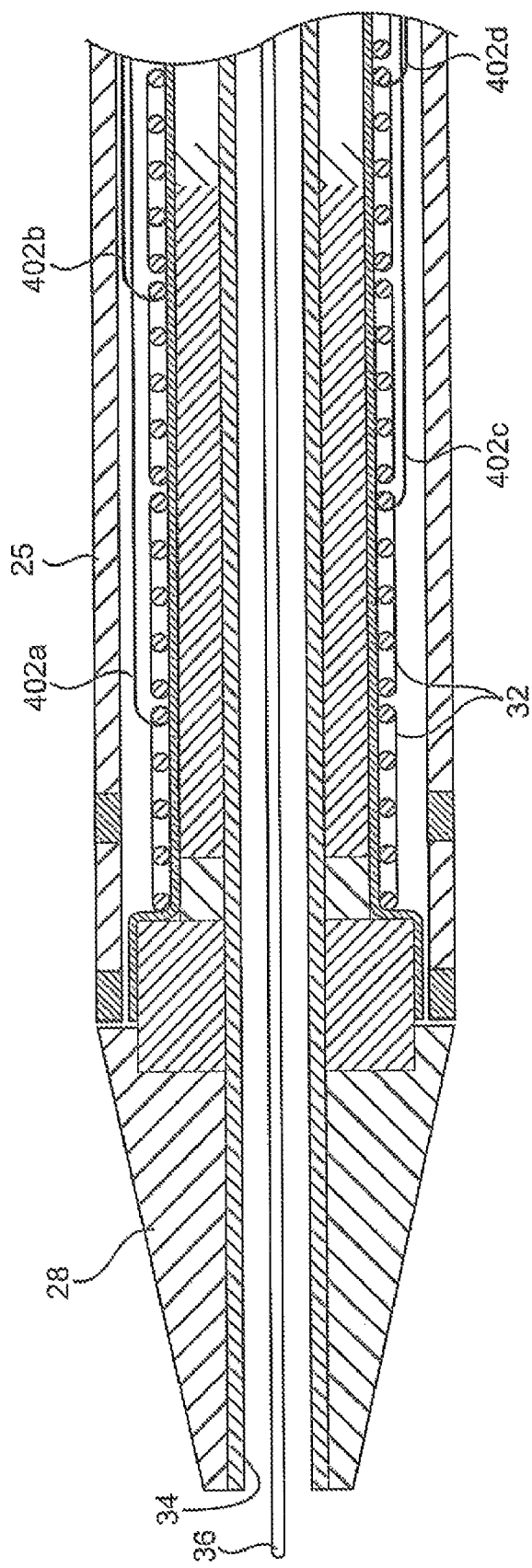
FIG. 37 is a cross-sectional view of a stent delivery catheter having release wires attached to stent segments.

Two embodiments of restraining mechanisms that include release wires are shown in FIGS. 37 and 38A-B. In these embodiments, one or more release wires are attached at their distal end(s) to one or more of the stent segment(s) carried by the delivery catheter. The wires extend through the length of the catheter such that their proximal end(s) extend out of the proximal end of the catheter and are attached to an actuator on the handle 38 or are otherwise accessible to the user at the proximal end of the catheter. While the wires remain attached to the stent segments, they allow the user to restrain movement of the associated stent segments as the outer sheath 25 or other components of the delivery catheter are moved relative to one another. The wires are preferably provided with a release mechanism such that the stent segment(s) may be selectively released from the wires, such as when it is desired to deploy the stent segment(s).

Turning first to FIG. 37, the delivery catheter includes a plurality of individual release wires 402a-d. Each release wire 402a-d is attached to an unique stent segment 32, thereby providing a mechanism for restraining and releasing each stent segment 32 individually. The release wires 402a-d are generally maintained in a taut condition in order to restrain the stent segments 32 against the backing force provided by the pusher tube 90.

The release wires 402a-d are identified by any method or mechanism suitable for indicating to the user the relationship between the release wire 402 and its respective stent segment 32. For example, the release wires 402a-d may be provided in individual carrier lumens, with each lumen being associated with a particular stent segment 32. Alternatively, the proximal ends of each release wire may be provided with an indicator, such as a color or other indicia, to indicate the relationship between the release wire 402 and its respective stent segment 32. Other and further identification methods may also be used.

As noted above, each release wire 402a-d is selectively detachable from its respective stent segment 32. Any of several detachment mechanisms may be used. For example, in one embodiment, each release wire 402a-d is looped around its stent segment 32 such that release of one end of the loop allows the release wire 402 to be pulled completely through the stent segment 32 and out of the delivery catheter. In other embodiments, each release wire 402a-d includes a weakened segment near its distal end that facilitates breakage of the release wire at the weakened segment, thereby releasing the stent segment 32. Other and further detachment mechanisms and methods may also be used.

The release wires 402a-d described herein include the additional advantage of providing a mechanism for verifying the count of individual stent segments 32 during a given interventional procedure. The release wires 402a-d also provide a positive mechanism for release of individual stent segments 32.

Another embodiment of a stent segment restraining mechanism using release wires is shown in FIGS. 38A-B. The restraining mechanism includes at least two wires, including a restraining wire 406 that extends generally along the inner surfaces of the column of stent segments 32, and a release wire 408 that extends generally along the outer surfaces of the column of stent segments 32. The proximal ends of each of the restraining wire 406 and release wire are located proximally of the proximal end of the catheter, and are accessible to the user in a similar manner to that described above in relation to the embodiment shown in FIG. 37. The restraining wire 406 is positioned such that a loop 410 of the restraining wire 406 extends through at least one gap formed in each of the stent segments 32. (See detailed illustration in FIG. 38B). The release wire 408 is routed through each of the loops 410 formed by the restraining wire 406, thereby securing the restraining wire 406 and release wire 408 to each of the individual stent segments 32. The stent segments 32 are thereby able to be restrained by the user by jointly maintaining the restraining wire 406 and release wire 408 in the configuration described above and illustrated in FIGS. 38A-B.

The stent segments are released by withdrawing the release wire 408 proximally. As the release wire 408 is withdrawn, it disengages each of the loops 410 extending through the gaps in the stent segments 32, thereby releasing each stent segment 32 from being restrained by the pair of wires. The release wire 408 may be withdrawn proximally in a single movement, releasing all of the stent segments 32 simultaneously. Alternatively, the release wire 408 may be withdrawn in stages, thereby releasing one or more stent segments 32 at each stage.

2. Spacing Mechanism

A spacing mechanism is shown in FIGS. 39A-D. The spacing mechanism is configured to cause stent segments to be deployed from the distal end of the delivery catheter described herein while creating a space between exposed stent segments and those stent segments that remain within and beneath the outer sheath of the catheter.

The spacing mechanism includes a pusher ribbon 420 that is adapted to be inserted between the outer sheath 25 and the column of stent segments 32 carried by the inner shaft of the catheter. The pusher ribbon 420 has a semi-cylindrical shape, and includes a radiopaque marker 422 at its distal end. An inward-facing tab 424 is also located near the distal end of the pusher ribbon 420. A plurality of slots 426 are provided along the length of the pusher ribbon. The slots 426 are preferably spaced apart by lengths that are approximately equal to the lengths of the shortest stent segments 32 carried by the catheter.

Figure 39A:
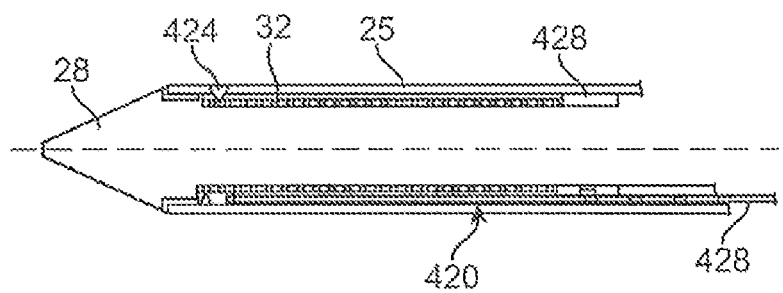
FIGS. 39A-D are cross-sectional and side views of a stent separation mechanism.
Figure 39B:
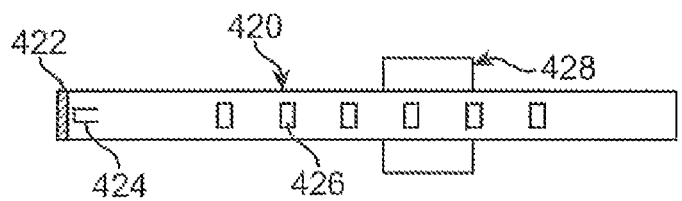
Figure 39C:
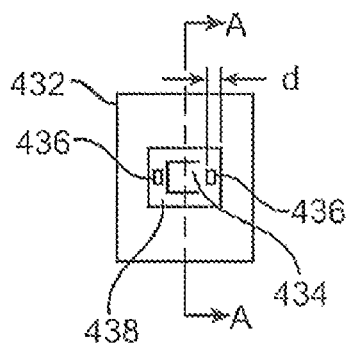
Figure 39D:
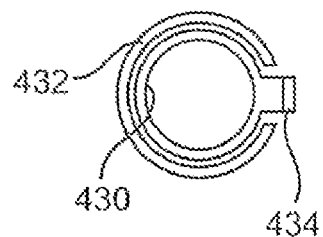

A pusher ring 428 is provided proximal to and adjacent to the proximal-most stent segment 32 of the column of stent segments 32. The pusher ring 428 includes an inner ring 430 and an outer ring 432. The inner ring includes an outward-facing tab 434 and a pair of pins 436 on either side of the tab 434. The outer ring includes a slot 438 adapted to allow the inner ring tab 434 and pins 436 to pass therethrough, as shown in FIGS. 39C-D. The length of the slot 438 is larger than the distance between the pins 436 of the inner ring 430 by a distance "d", as explained more fully below.

To operate the spacing mechanism, the catheter is placed in its deployment location at a treatment site. The radiopaque marker 56 on the outer sheath 25 is placed at the distal-most point of the treatment location, and the pusher ribbon 420 is retracted such that the radiopaque marker 422 at the distal end of the pusher ribbon 420 is located at the proximal-most point of the treatment location. At this point, the pusher tube 86 (to which the pusher ribbon 420 is attached) is maintained in position as the outer sheath 25 is retracted proximally. The tab 424 on the pusher ribbon engages the proximal-most of the stent segments 32 that are to be deployed, thereby maintaining that stent segment 43 and those located distally of that stent segment 32 in place relative to the inner shaft of the catheter. As the outer sheath 25 is retracted, the stent segments 32 to be deployed are exposed, similarly to the manner described above in relation to the paving process.

As the outer sheath 25 is retracted proximally, the outer sheath 25 frictionally engages the remaining stent segments 32 located internally of the sheath. This causes the column of remaining stent segments 32 to apply a proximally directed force against the pusher ring 428. More specifically, the column of stent segments 32 back up against the inner ring 430 of the pusher ring 428, thereby causing the inner ring 430 to slide proximally relative to the outer ring 432 by the separation distance "d" shown in FIG. 39C. This movement creates a separation between the column of stent segments 32 located beneath the outer sheath 25, and the proximal-most of the stent segment(s) 32 that are to be deployed. By proper sizing of the separation distance "d", the separation distance between the stent segments 32 needed to ensure proper stent segment deployment is created.

3. Screw Mechanism

Figure 40:
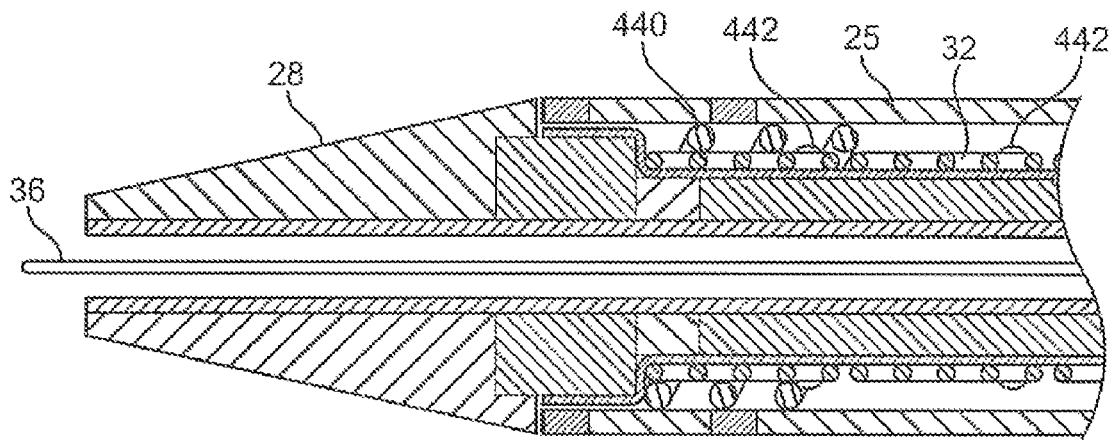
FIG. 40 is a cross-sectional view of a screw drive deployment mechanism.

A stent deployment mechanism is shown in FIG. 40. The stent deployment mechanism includes a screw drive that is configured to engage the stent segments carried by the catheter. By providing relative rotation between the stent segments and the screw drive, stent segments are caused to move relative to the outer sheath of the catheter, thereby facilitating the paving process. Relative rotation between the stent segments and the screw drive may be provided either by rotation of the outer sheath (to which the screw drive is attached), or by rotating the stent segments carried on the catheter inner shaft.

Turning to FIG. 40, the delivery catheter includes a spring screw member 440 that is preferably attached to or embedded within the inner surface of the outer sheath 25 near its distal end. The spring screw member 440 is generally in the form of a coiled spring having spaced inclined coils, thereby defining pitched threads. Alternatively, conical or otherwise shaped threads may be formed on the inner surface of the outer sheath.

At least one thread engagement member 442 is formed on the external surface of each of the stent segments 32. The thread engagement members 442 are preferably formed as partial circumferential humps of a coating or other material having sufficient strength and rigidity to engage the coils of the spring screw member 440 as the two members are rotated relative to one another.

To operate the stent deployment mechanism, the spring screw member 440 must be rotated relative to the stent segments 32. As noted above, this relative rotation may be achieved either by rotation of the outer sheath 25, or by rotation of the stent segments 32. The stent segments 32 may be rotated either by rotation of the inner shaft upon which they are carried. Alternatively, the stent segments 32 are rotated by rotation of the pusher tube 86 that engages the proximal-most stent segment 32, provided that there is a positive engagement between the distal end of the pusher tube 86 and the proximal-most stent segment 32, and that the stent segments 32 are interlocked or otherwise prevented from rotating relative to one another. Upon relative rotation of the spring screw member 440 and the stent segments 32, the outer sheath 25 is causes to retract proximally relative to the stent segments 32, thereby deploying the stent segments from the distal end of the catheter.

4. Wire Wrap Stent Shuttle

Figure 41:
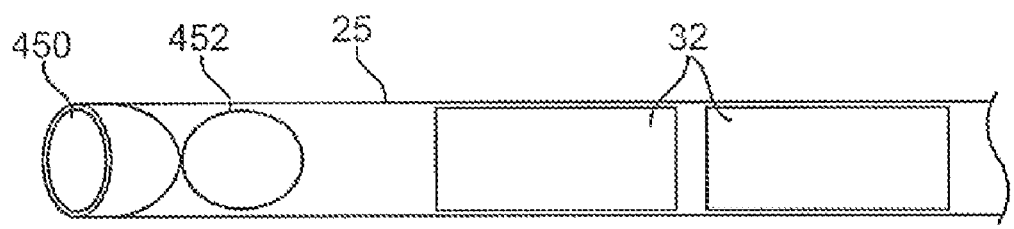
FIG. 41 is a schematic representation of a wire loop shuttle mechanism.

Another stent deployment mechanism is shown schematically in FIG. 41. The deployment mechanism includes an end stop 450 that is attached to or embedded within the outer sheath 25 near its distal end. The end stop 450 is preferably formed of stainless steel or other metallic material, or its may be formed of a resilient, rigid plastic or polymeric material. A wire loop 452 is attached to the end stop 450. More specifically, each end of a length of wire is attached to the end stop 450, the remainder of the wire extending proximally within the outer sheath 25 to define a loop 452.

Although not shown in the FIG. 41 drawing, the stent segments 32 are carried by the inner shaft of the catheter, just as the device is otherwise described above in relation to FIGS. 1-6. The outer sheath 25 is able to be retracted proximally relative to the stent segments 32 as pressure is maintained on the pusher tube 86, as is also described above.

To operate the stent deployment mechanism, the outer sheath 25 is retracted an amount sufficient to allow the wire loop 452 to engage the distal-most stent segment 32. The wire loop 452 expands radially during retraction of the outer sheath 25, thereby allowing the wire loop 452 to engage the outer surface of the stent segment 32. As the outer sheath 25 is then advanced distally, the wire loop 452 tightens around the stent segment 32, thereby allowing the distal movement of the outer sheath 25 to move the stent segment 32 distally along the catheter inner shaft. The wire loop 452 thereby functions as a shuttle mechanism, allowing the user to move stent segments 32 distally along the inner shaft of the catheter.

The deployment mechanism will typically function best when transporting only one stent segment 32 at a time Although the device may also be used to transport two or more stent segments 32 simultaneously, the addition of more stent segments 32 increases the likelihood that the segments will become jammed within the catheter.

5. Sliding Sheath Deployment Mechanism

Figure 42:
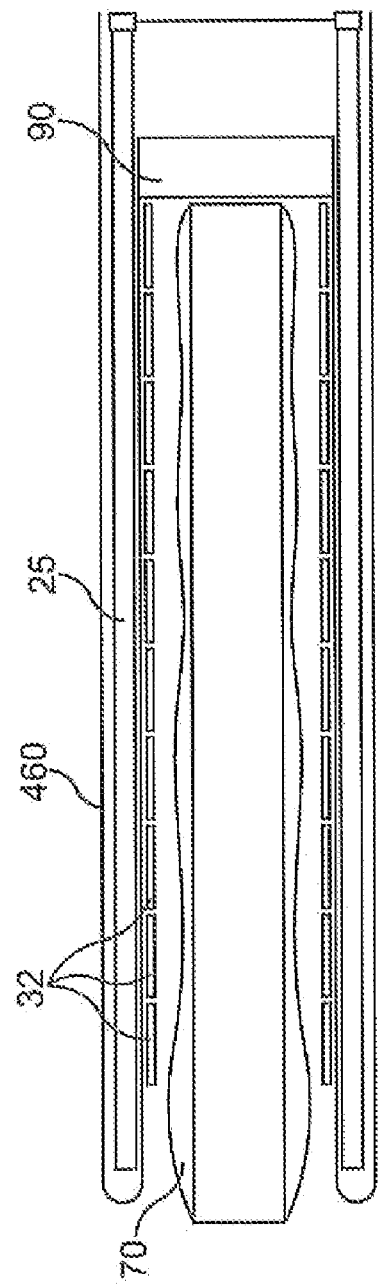
FIG. 42 is a cross-sectional view of a stent deployment mechanism including a sliding sheath.

Turning to FIG. 42, another stent deployment mechanism is shown. The stent deployment mechanism is a modified version of the delivery catheter generally described above. The deployment mechanism includes an outer sheath 25, a balloon member 70 attached to an inner shaft located internally of the outer sheath 25, a plurality of stent segments 32, and a pusher ring 90 located adjacent to and proximal to the proximal-most stent segment 32. The foregoing components are generally configured in the same manner as the delivery devices described above.

In addition, the deployment mechanism includes a mounting sleeve 460 to which the stent segments 32 are attached. In other words, the stent segments 32 are not carried by the balloon member 70 on the catheter inner shaft, they are instead held on and carried by the mounting sleeve 460. The mounting sleeve 460 extends along the inner surface of the outer sheath 25 but is not attached thereto. Instead, the mounting sleeve 460 is inverted over the distal end of the outer sheath 25, and then extends proximally along the outer surface of the outer sheath 25 to the proximal end of the delivery catheter. Each of the mounting sleeve 460, the outer sheath 25, and the pusher ring 90 is able to be separately controlled by the user.

To operate the deployment mechanism, the outer sheath 25 and mounting sleeve 460 are withdrawn proximally with the pusher 90 held in place in order to expose the number of stent segments 32 required to be deployed. Index markers may optionally be provided on the mounting sleeve 460 to indicate the number of stent segments 32 that have been exposed during the paving process. Separation is achieved by retracting proximally the pusher 90, outer sheath 25, and the mounting sleeve 460 together, thereby separating the stent segments still retained within the outer sheath 25 from those exposed during the paving process. The balloon 70 is then expanded to deploy the exposed stent segments.

The foregoing descriptions of the preferred embodiments are intended to serve as non-limiting examples of the devices and methods of the present invention. Variations of the devices and methods described herein have also been contemplated. For example, it should be understood that when the movement of the pusher tube, sheath, or stent segments is described in relation to other components of the delivery catheter, such movement is relative and will encompass both moving the sheath, pusher tube, or stent segments while keeping the other component(s) stationary, keeping the sheath, pusher tube or stent segments stationary while moving the other component(s), or moving multiple components simultaneously relative to each other. In addition, in any of the above embodiments that include electrical conductors, light energy conductors, or the like, these conductors may be incorporated into the device by embedding in the body of a component of the delivery catheter, attachment to the internal or external surface of such a component, or by other suitable means. Still further, electrical conduction may be obtained through use of copper wire or other suitable conductor (with insulation if appropriate) that may be incorporated into the reinforcing braid embedded in the wall of the outer sheath in the preferred embodiments (i.e., all or some of the strands of the reinforcing braid may be made of a suitably conductive material and used as an electrical conductor). Still other variations are possible.

While the foregoing description of the invention is directed to a stent delivery catheter for deploying stents into vascular lumens to maintain patency, it should be understood that various other types of wire-guided catheters also may embody the principles of the invention. For example, balloon catheters for angioplasty and other purposes, particularly those having a slidable external sheath surrounding the balloon, may be constructed in accordance with the invention. Other types of catheters for deployment of prosthetic devices such as embolic coils, stent grafts, aneurism repair devices, annuloplasty rings, heart valves, anastomosis devices, staples or clips, as well as ultrasound and angiography catheters, electrophysiological mapping and ablation catheters, and other devices may also utilize the principles of the invention.

Although the above is complete description of the preferred embodiments of the invention, various alternatives, additions, modifications and improvements may be made without departing from the scope thereof, which is defined by the claims.

What is claimed is:

1. A delivery system for delivering a plurality of prostheses to a treatment site, comprising:
    a sheath having a proximal end, a distal end, an opening at the distal end, and a passage in communication with the opening, the plurality of prostheses being movably disposed in the passage, and
    a valve at or near the distal end of the sheath adapted for selectively retaining at least one prosthesis within the passage, wherein the valve comprises an impinger that is selectively moved from a first state in which it does not engage the at least one prosthesis to a second state in which it engages the at least one prosthesis and prevents its relative movement,
    wherein the impinger is formed of a deformable cylinder having a first diameter in the first state which is larger than an outer diameter of the at least one prosthesis and a second diameter in the second state which is smaller than the first diameter when the impinger is electrically actuated such that the cylinder contacts and engages the at least one prosthesis.

2. The delivery system of claim 1, wherein said valve is configured to engage only a single prosthesis.

3. The delivery system of claim 1, wherein said valve is configured to engage a plurality of prostheses.

4. The delivery system of claim 1, wherein said valve is configured to engage each one of the plurality of prostheses retained within the passage.

5. A delivery system for delivering a plurality of prostheses to a treatment site, comprising:
- a sheath having a proximal end, a distal end, an opening at the distal end, and a passage in communication with the opening, the plurality of prostheses being movably disposed in the passage, and
- an energy actuable valve at or near the distal end of the sheath adapted for selectively retaining at least one prosthesis within the passage, wherein the energy actuable valve is selectively movable from a first state in which it does not engage at least one prosthesis to a second state in which it engages at least one prosthesis when energy is applied to the valve,
- wherein the energy actuable valve is formed of a deformable cylinder having a first diameter in the first state which is larger than an outer diameter of the at least one prosthesis and a second diameter in the second state which is smaller than the first diameter when the energy actuable valve is electrically actuated such that the cylinder contacts and engages the at least one prosthesis.

6. The delivery system of claim 5, wherein said valve is actuable by application of electricity further comprising a power source electrically coupled to the energy actuable valve.

7. The delivery system of claim 5, wherein said valve is formed of a shape memory material.

8. The delivery system of claim 7, wherein said valve is formed of nickel titanium alloy.

9. The delivery system of claim 5, wherein said valve comprises a generally cylindrical member attached to the inner surface of the sheath at or near the distal end thereof.

10. The delivery system of claim 6, further comprising a heating element that is heated by the application of electricity, and wherein said valve is actuated by said heating element.

11. The delivery system of claim 9, further comprising a shape memory tube arranged concentrically with said generally cylindrical member and adapted to apply a radial force thereto.

12. The delivery system of claim 1, wherein the valve comprises a loop member which is configured to contract radially inward upon actuation such that a valving force is applied upon the at least one prosthesis.

13. The delivery system of claim 12, wherein the loop member comprises a shape memory alloy.

14. The delivery system of claim 12, wherein the valve comprises a compliant material upon which the loop member is attached.

15. The delivery system of claim 5, wherein the valve comprises a loop member which is configured to contract radially inward upon actuation such that a valving force is applied upon the at least one prosthesis.

16. The delivery system of claim 15, wherein the loop member comprises a shape memory alloy.

17. The delivery system of claim 15, wherein the valve comprises a compliant material upon which the loop member is attached.

* * * * *